(12) United States Patent
Lysecky et al.

(10) Patent No.: US 11,868,479 B2
(45) Date of Patent: Jan. 9, 2024

(54) RUNTIME ADAPTIVE RISK ASSESSMENT AND AUTOMATED MITIGATION

(71) Applicant: Arizona Board of Regents on Behalf of the University of Arizona, Tucson, AZ (US)

(72) Inventors: Roman Lysecky, Tucson, AZ (US); Jerzy Rozenblit, Tucson, AZ (US); Johannes Sametinger, Linz (AT); Aakarsh Rao, Tucson, AZ (US); Nadir Carreon, Tucson, AZ (US)

(73) Assignees: ARIZONA BOARD OF REGENTS ON BEHALF OF THE UNIVERSITY OF ARIZONA, Tucson, AZ (US); JOHANNES KEPLER UNIVERSITY LINZ, Linz (AT)

( * ) Notice: Subject to any disclaimer, the term of this patent is extended or adjusted under 35 U.S.C. 154(b) by 294 days.

(21) Appl. No.: 17/290,627

(22) PCT Filed: Nov. 1, 2019

(86) PCT No.: PCT/US2019/059551
§ 371 (c)(1),
(2) Date: Apr. 30, 2021

(87) PCT Pub. No.: WO2020/093020
PCT Pub. Date: May 7, 2020

(65) Prior Publication Data
US 2022/0035927 A1 Feb. 3, 2022

Related U.S. Application Data

(60) Provisional application No. 62/755,110, filed on Nov. 2, 2018.

(51) Int. Cl.
*G06F 21/57* (2013.01)
*G16H 20/17* (2018.01)
(Continued)

(52) U.S. Cl.
CPC .......... *G06F 21/577* (2013.01); *A61B 5/0022* (2013.01); *A61B 5/0031* (2013.01);
(Continued)

(58) Field of Classification Search
CPC ................. G06F 21/577; G06F 21/566; G06F 2221/034; G16H 20/17; A61B 5/0022;
(Continued)

(56) References Cited

U.S. PATENT DOCUMENTS 7,188,513 B2  3/2007  Wilson
7,260,844 B1  8/2007  Tidwell et al.
(Continued)

FOREIGN PATENT DOCUMENTS

WO  WO 2010/104929 A1  9/2010

OTHER PUBLICATIONS

Almohri et al. (Jul. 2017) On Threat Modeling and Mitigation of Medical Cyber-Physical Systems, IEEE/ACM International Conference on Connected Health: Applications, Systems and Engineering Technologies (CHASE), Jul. 17-19, 2017, pp. 114-119.
(Continued)

*Primary Examiner* — Stephen T Gundry
(74) *Attorney, Agent, or Firm* — Leydig, Voit & Mayer, Ltd.

(57) ABSTRACT

A security framework for life-critical and safety-critical devices, specifically medical devices, using: a) runtime, adaptive methods that dynamically assess the risk of newly discovered vulnerabilities and threats, and b) automatic mitigation methods that reduce system risk by seamlessly reconfiguring the device to operate within different execution modes. This technology automatically isolates threats by disabling affected system components. A multi-modal software design uses adaptive software in which operational modes have monotonically decreasing cumulative risk. For-
(Continued)

mal risk models are used to model the individual risk of accessing or controlling system components and to automatically calculate the cumulative risk of software modes. The automated detection of potential threats by the system or reporting of known vulnerabilities will dynamically change the system risk. To support an accurate and fine grained adaptive risk model, novel statistical methods non-intrusively detect potential threats, isolate the threat to a specific component, and estimate the threat probability.

24 Claims, 29 Drawing Sheets

(51) Int. Cl.
  *A61B 5/00*    (2006.01)
  *A61N 1/362*   (2006.01)
  *A61N 1/372*   (2006.01)
  *G06F 21/56*   (2013.01)
  *A61M 5/142*   (2006.01)

(52) U.S. Cl.
  CPC ......... *A61N 1/362* (2013.01); *A61N 1/37223* (2013.01); *G06F 21/566* (2013.01); *G16H 20/17* (2018.01); *A61M 5/14276* (2013.01); *G06F 2221/034* (2013.01)

(58) Field of Classification Search
  CPC .. A61B 5/0031; A61N 1/362; A61N 1/37223; A61M 5/14276
  See application file for complete search history.

(56) References Cited

U.S. PATENT DOCUMENTS

| | | | |
|---|---|---|---|
| 7,937,761 B1 | 5/2011 | Bennett | |
| 8,779,921 B1 | 7/2014 | Curtiss | |
| 11,645,388 B1* | 5/2023 | Kimball | G06N 20/20 726/23 |
| 2007/0240207 A1 | 10/2007 | Belakhdar et al. | |
| 2009/0276011 A1* | 11/2009 | Hyde | A61N 1/37247 607/60 |
| 2015/0172300 A1* | 6/2015 | Cochenour | G06F 21/6218 726/23 |
| 2017/0124327 A1* | 5/2017 | Kumbhar | G06F 21/566 |
| 2017/0348536 A1* | 12/2017 | Hyde | G16H 40/63 |
| 2018/0025157 A1 | 1/2018 | Titonis et al. | |
| 2021/0224282 A1* | 7/2021 | Poirel | G06F 21/554 |
| 2022/0263856 A1* | 8/2022 | King-Wilson | G06Q 40/08 |
| 2022/0329616 A1* | 10/2022 | O'Hearn | H04L 63/10 |
| 2022/0353282 A1* | 11/2022 | Paine | H04L 63/1416 |
| 2022/0368682 A1* | 11/2022 | Verzun | H04L 9/50 |
| 2022/0377093 A1* | 11/2022 | Crabtree | H04L 43/045 |
| 2023/0008173 A1* | 1/2023 | Crabtree | H04L 63/1441 |
| 2023/0042552 A1* | 2/2023 | Stockdale | H04L 41/069 |

OTHER PUBLICATIONS

Ammann et al. (2002) Scalable, graph-based network vulnerability analysis, Conference on Computer and communications security (CCS '02), Nov. 18-22, 2002, pp. 217-224.
ARM (2011) Embedded Trace Macrocell ETMv1.0 to ETMv3.5 Architecture Specification.
ARM Security Technology (2005-2009) Building a Secure System using TrustZone® Technology, ARM Limited.
Arnes et al. (2006) Using Hidden Markov Models to Evaluate the Risks of Intrusions: System Architecture and Model Validation, Recent Advances in Intrusion Detection, LNCS 4219, pp. 145-164.
Arora et al. (2005) Secure embedded processing through hardware-assisted run time monitoring. design. In Automation and Test in Europe Conference, Mar. 7-11, 2005, 178-183.
Arora et al. (2006) Architectural Support for Safe Software Execution on Embedded Processors, Conference on Hardware Software Co-design and System Synthesis, Oct. 22-25, 2006, pp. 106-111.
Babar et al. (2011) Proposed Embedded Security Framework for Internet of Things (IoT), Proc. 2011 2nd Int'l Conf. Wireless Communication, Vehicular Technology, Information Theory and Aerospace ElectronicSystems Technology (Wireless VITAE 11), pp. 1-5.
Baluja et al. (1995) Removing the Genetics from the Standard Genetic Algorithm, Technical Report. Carnegie Mellon Univ., Pittsburgh, PA, USA, pp. 38-46.
Bandyopadhyay et al. (2011) Internet of things: Applications and challenges in technology and standardization, Wireless Personal Communications 58.1, 49-69.
Bergstra et al. (2011) Algorithms for Hyper-Parameter Optimization. In Proc. Of NIPS'11.
Bhatkar et al. (2006) Dataflow anomaly detection, In Symposium on Security and Privacy, pp. 15 pp. -62.
Biro et al. (Jan./Feb. 2018) Software safety and security risk mitigation in cyber-physical systems, IEEE Softw., 35(1), 24-29.
Blyth et al. (2006) Performing real-time threat assessment of security incidents using data fusion of IDS logs, J. Computer Security, vol. 14, pp. 513-534.
Boehm et al. (1991) Software risk management: principles and practices, IEEE Software, vol. 8, No. 1, pp. 32-41.
Bond et al. (2010) Efficient, context-sensitive detection of real-world semantic attacks, Programming Languages and Analysis for Security, pp. 1-10.
Bonderud (Apr. 2018) Supply Chain and IT Risks Pose Healthcare Cybersecurity Challenges, Report Reveals, Security Intelligence.
Botev et al. (2010) Kernel density estimation via diffusion. Annals of Statistics. 38, 5, 2916-2957.
Burleson et al. (2012) Design challenges for secure implantable medical devices, Design Automation Conference(DAC), Jun. 3-7, 2012, pp. 12-17.
Cai et al. (2014) A survey of small-scale unmanned aerial vehicles: Recent advances and future development trends, *Unmanned Systems*, vol. 2, No. 2, 175-199.
Carreon et al. (Apr. 29-May 2, 2019) Window-based Statistical Analysis of Timing Subcomponents for Efficient Detection of Malware in Life-Critical Systems, Spring Simulation Conference (SpringSim), 2019, pp. 1-12, doi: 10.23919/SpringSim.2019.8732899.
Carreon et al. (Mar. 9-13, 2020) Statistical Time-based Intrusion Detection in Embedded Systems, 2020 Design, Automation & Test in Europe Conference & Exhibition (DATE), 2020, pp. 562-567, doi: 10.23919/DATE48585.2020.9116369.
Carreon et al. (Mar. 2021) Probabilistic Estimation of Threat Intrusion in Embedded Systems for Runtime Detection. ACM Trans. Embed. Comput. Syst. 20, 2, Article 14, 23 pages. https://doi.org/10.1145/3432590.
Carreon et al. (Oct. 7-10, 2018) Hardware-Based Probabilistic Threat Detection and Estimation for Embedded Systems, IEEE 36th International Conference on Computer Design (ICCD), pp. 522-529.
Carruthers (2016) Internet of Things and Beyond: Cyber-physical Systems, IEEE Internet of Things Newsletter.
Chakravarti et al. (1967) Handbook of Methods of Applied Statistics, vol. I, John Wiley and Sons, pp. 392-394.
Chandola et al. (2009) Anomaly Detection: A Survey, ACM Computing Survey, 41(3).
Cheboli (2010) Anomaly detection of time series. PhD dissertation, University of Minnesota.
Chen et al. (2005) Non-control-data attacks are realistic threats, *USENIX Security Symp.*, pp. 177-192.
Chen et al. (2014) A Study on Advanced Persistent Threats, IFIP International Conference on Communications and Multimedia Security, vol. 8735, pp. 63-72.
Cheng et al. (2009) Software engineering for self-adaptive systems: A research roadmap, Software engineering for self-adaptive systems, pp. 1-26.

(56) References Cited

OTHER PUBLICATIONS

Cherdantseva et al. (2016) A review of cyber security risk assessment methods for scada systems, Computers and Security, vol. 56, pp. 1-27.
Chiu et al. (2001) Analysis of the increase and decrease algorithms for congestion avoidance in computer networks, Computer Networks and ISDN systems 17, No. 1, pp. 1-14.
Coley et al. (Sep. 2019) Rubric for Applying CVSS to Medical Devices, The MITRE Corporation, Version: 0.12.04.
Cristian-Valentin et al. (2013) Data compression and panoramic images formation in UAV military TV-monitoring system. Eur Sci J 9(33): 436-449.
Deng et al. (2010) Flexible and efficient instruction-grained runtime monitoring using on-chip reconfigurable fabric. In Proceedings of the 43rd Annual IEEE/ACMInternational Symposium on Microarchitecture. 137-148.
Dimitrov (2016) Medical Internet of Things and Big Data in Healthcare, Healthcare Informatics Research 22.3, 156-163.
Ellson et al. (2002) Graphviz—Open source graph drawing tools. In Graph Drawing. Springer, 2002, 483-484.
European Search report dated Jun. 3, 2022, for corresponding EP Patent Application No. 19880176.3.
Evans (2011) The Internet of Things: How the Next Evolution of the Internet Is Changing Everything, Cisco White Paper.
Fawcett (2006) An Introduction to ROC Analysis, Pattern Recognition Letters, vol. 27, No. 8, pp. 861-874.
Federal Financial Institutions Examination Council (2014) Cyberattacks on Financial Institutions' ATM and Card Authorization Systems. https://www.ffiec.gov.
Food and Drug Administration (2005) Guidance for Industry and Food and Drug Administration Staff, Guidance for the Content of Premarket Submissions for Software Contained in Medical Devices, U.S. Food and Drug Administration.
Food and Drug Administration (2014) Content of Premarket Submissions for Management of Cybersecurity in Medical Devices, Guidance for Industry and Food and Drug Administration Staff.
Food and Drug Administration (2016) Postmarket Management of Cybersecurity in Medical Devices, Guidance for Industry and Food and Drug Administration Staff, URL: www.fda.gov/downloads/medicaldevices/deviceregulationandguidance/guidancedocuments/ucm482022.pdf.
Frossi et al. (2009) Selecting and improving system call models for anomaly detection, Conf. on Detection of Intrusions and Malware, and Vulnerability, pp. 206-223.
Frost and Sullivan (2007) Study Analysing the Current Activities in the Field of UAV. Tech. Rep., European Commission Enterprise and Industry Directorate-General.
Fuhr et al.(2013) The Business Case for Medical Device Quality, Mckinsey Center for Government.
Gao et al. (2003) Gray-box extraction of execution graphs for anomaly detection. In ACM Conference on Computer and Communications Security, Oct. 25-29, 2004, 318-329.
Goldstein et al. (2012) Histogram-based outlier score (hbos): A fast unsupervised anomaly detection algorithm. Poster and Demo Track, pp. 59-63.
GrandViewResearch (Feb. 2018) Cyber Security Market Size, Share & Trends Report Cyber Security Market Size, Share & Trends Analysis Report by Component, by Security Type, by Solution, by Services, by Deployment, by Organization Size, by Applications, by Region, and Segment Forecasts, 2022-2030, GrandViewResearch.
Gusmão et al. (2016) Information security risk analysis model using fuzzy decision theory, International Journal of Information Management, vol. 36, No. 1, pp. 25-34.
Halperin et al. (2008) Pacemakers and Implantable Cardiac Defibrillators: Software Radio Attacks and Zero-Power Defenses, Proc. 2008 IEEE Symp. Security and Privacy (SP 08), pp. 129-142.
Hanna et al. (2011) Take two software updates and see me in the morning: The case for software security evaluations of medical devices, USENIX Conference on Health Security and Privacy.

Hartmann et al. (2013) The vulnerability of UAVs to cyber attacks—An approach to the risk assessment, 2013 5th International Conference on Cyber Conflict (CYCON 2013), Tallinn, Estonia, Jun. 4-7, 2013, pp. 1-23.
Heller et al. (2003) One class support vector machines for detecting anomalous windows registry accesses. In Proceedings of the Workshop on Data Mining for Computer Security.
Holm (2014) Signature Based Intrusion Detection for Zero-Day Attacks: (Not) a Closed Chapter?, Hawaii International Conf. on System Sciences, pp. 4895-4904.
Hossain et al. (2015) Towards an Analysis of Security Issues, Challenges, and Open Problems in the Internet of Things, IEEE World Congress on Services, pp. 21-28.
Idika al. (2007) A Survey of Malware Detection Techniques. Technical Report, Purdue University.
International Search Report and Written Opinion, Corresponding to International Application No. PCT/US2019/059551, dated Jan. 16, 2020.
Irick et al. (2008) A hardware efficient support vector machine architecture for FPGA, Proc. Annu. IEEE Symp. Field-Programm. Custom Comput. Mach., pp. 304-305.
Islam et al. (2016) A Risk Assessment Framework for Automotive Embedded Systems, Proceedings of the 2nd ACM International Workshop on Cyber-Physical System Security (CPSS), pp. 3-14.
Jiang et al. (2012) Modeling and Verification of a Dual Chamber Implantable Pacemaker, Conf. on Tools and Algorithms for the Construction and Analysis of Systems, pp. 188-203.
Jiang et al. (2015) High-Confidence Medical Device Software Development, Found. Trends Electron. Des. Autom. 9, pp. 309-391.
Joung (2013) Development of Implantable Medical Devices: From an Engineering Perspective, International Neurourology Journal 17.3, 98-106.
Khakpour et al. (2012) Formal modeling of evolving selfadaptive systems, Science of Computer Programming, vol. 78 (1), pp. 3-26.
Khan et al. (2005) Hardware-based support vector machine classification in logarithmic number systems, Int. Symp. Circuits Syst., vol. 5, pp. 5154-5157.
Kim et al. (2012) Cyber attack vulnerabilities analysis for unmanned aerial vehicles, The American Institute of Aeronautics and Astronautics: Reston, VA, USA.
Koo et. al. (2001) Hierarchical approach for design of multi-vehicle multi-modal embedded software, International Workshop on Embedded Software, pp. 344-360.
Kramer et al. (2012) Security and Privacy Qualities of Medical Devices: An Analysis of FDA Postmarket Surveillance, PLoS One, vol. 7, No. 7.
Krishnamurthy et al. (2016) How the internet of things is transforming medical devices, Cognizant 20-20 Insights, Cognizant.
Kruegel et al. (2005) Automating Mimicry Attacks using Static Binary Analysis, USENIX Security Symposium, pp. 161-176.
Kulkarni et al. (2016) Real-time anomaly detection framework for many-core router through machine learning techniques, Journal on Emerging Technologies in Computing Systems, vol. 13, No. 1, Article 10.
Kure et al. (May 2018) An integrated cyber security risk management approach for a cyber-physical system, Applied Sciences, 8(6), pp. 898.
Lee (2008) Cyber physical systems: Design challenges, IEEE Object Oriented Real-Time Distributed Computing, Orlando, FL, USA, 2008, pp. 363-369.
Lee et al. (2016) Integration of ROP/JOP monitoring IPs in an ARM-based SoC, Conference on Design, Automation & Test in Europe, Mar. 14-18, 2016, pp. 331-336.
Li et al. (2004) Selecting a fuzzy aggregation operator for multicriteria fault location problem, IEEE PES Power Systems Conference and Exposition, Oct. 10-13, 2004, pp. 1476-1482, vol. 3.
Li et al. (2011) Hijacking an insulin pump: Security attacks and defenses for a diabetes therapy system, IEEE International Conference on e-Health Networking, Applications and Services, Jun. 13-15, 2011, pp. 150-156.
Li et al. (2013) Improving the trustworthiness of medical device software with formal verification methods. IEEE Embed. Syst. Lett. 5, 50-53.

(56) References Cited

OTHER PUBLICATIONS

Liu (2014) Some Hamacher Aggregation Operators Based on the Interval-Valued Intuitionistic Fuzzy Numbers and Their Application to Group Decision Making, IEEE Transactions on Fuzzy Systems, vol. 22, No. 1, pp. 83-97.
Lu et al. (Apr. 2019) Data-driven Anomaly Detection with Timing Features for Embedded Systems. ACM Trans. Des. Autom. Electron. Syst. 24, 3, Article 33, 27 pages.
Lu et al. (Mar. 2018) Time and Sequence Integrated Runtime Anomaly Detection for Embedded Systems, ACM Transactions on Embedded Computing Systems (TECS), vol. 17(2), Article 38, pp. 1-27.
Lu et al. (Jan. 2015) Timing-based anomaly detection in embedded systems, In Proceedings of the 20th Asia and South Pacific Design Automation Conference, Jan. 19-22, 2015, pp. 809-814.
Lu et al. (Nov. 5-8, 2017) Subcomponent Timing-Based Detection of Malware in Embedded Systems. IEEE International Conference on Computer Design (ICCD), pp. 17-24.
Lu et al. (Oct. 2015) Analysis of Control Flow Events for Timing-based Runtime Anomaly Detection, Proceedings of the WESS'15: Workshop on Embedded Systems Security. Association for Computing Machinery, New York, NY, USA, Article 3, 1-8.
Mao et al. (2010) Hardware support for secure processing in embedded systems. IEEE Transactions on Computers, 59, 6, 847-854.
Marin et al. (2016) On the feasibility of cryptography for a wireless insulin pump system. In ACM Conference on Data and Application Security and Privacy, Mar. 9-11, 2016, 113-120.
Martin et al. (2008) Medical Device Development: The Challenge for Ergonomics, Applied Ergonomics, vol. 39, No. 3, 271-283.
Maxion et al. (2002) Anomaly detection in embedded systems. IEEE Transactions on Computers. 51, 2, 108-120.
McCarthy et al. (2014) Characterization of Potential Security Threats in Modern Automobiles: A Composite Modeling Approach. National Highway Traffic Safety Administration, Washington Tech. Rep.
McKinley et al. (2004) Composing Adaptive Software, Computer, vol. 37 (7), pp. 56-64.
Medtronic Inc (accessed Sep. 2019) MiniMed 670G Insulin Pump, Available: www. medtronicdiabetes. com/products/minimed-670g-insulin-pump-system.
Mell et al. (2007) A complete guide to the common vulnerability scoring system version 2.0, Forum of Incident Response and Security Teams (FIRST).
Microblaze (2009) Microblaze processor reference guide embedded development kit EDK 11.4. 102-104.
Miorandi et al. (2012) Internet of things: Vision, Applications and Research Challenges, Ad Hoc Networks, vol. 10, Issue 7, 1497-1516.
Mohan et al. (2013) Secure system simplex architecture for enhanced security and robustness of cyber-physical systems. ACM Conference on High Confidence Networked Systems (HiCoNS '13), Apr. 9-11, 2013, Association for Computing Machinery, New York, NY, USA, 62-71.
Monti (1995) Folded Empirical Distribution Function Curves-Mountain Plots, The American Statistician, vol. 49, No. 4, pp. 342-345.
Moreno et al. (Sep. 2017) Non-Intrusive Runtime Monitoring Through Power Consumption to Enforce Safety and Security Properties in Embedded, Formal Methods in Software Design (FMSD).
Morris (Aug. 2017) 465,000 Pacemakers Recalled on Hacking Fears, URL: fortune. com/2017/08/31/ pacemaker-recall-fda/, Fortune.
National Institute of Standards and Technology (2012) Guide for Conducting Risk Assessments, NIST Special Publication 800-30 Revision 1.
Oh et al. (2002) Hardware-software cosynthesis of multi-mode multi-task embedded systems with real-time constraints, Proceedings of the Tenth International Symposium on Hardware/Software Codesign (CODES), pp. 133-138.
Omar et al. (2013) Machine learning techniques for anomaly detection: An overview. International Journal of Computer Applications, vol. 79, No. 2, pp. 33-41.
Palani et al. (2016) Invisible and forgotten: Zero-day blooms in the IoT, IEEE International Conference Pervasive Computing and Communication Workshops (PerCom Workshops), Mar. 14-18, 2016.
Parzen (1962) On Estimation of a Probability Density Function and Mode. Ann. Math. Statist. 33, No. 3, 1065-1076. doi:10.1214/aoms/1177704472.
Patel et al. (2008) Shield: A Software Hardware Design Methodology for Security and Reliability of MPSOCs. Design Automation Conference, Jun. 8-13, 2008, pp. 858-861.
Patel et al. (2011) Architectural Frameworks for Security and Reliability of MPSoCs, IEEE Transactions on Very Large Scale Integration Systems, No. 9, pp. 1641-1654.
Paunicka et al. (2001) The OCP—an open middleware solution for embedded systems, Proceedings of the 2001 American Control Conference, Jun. 25-27, 2001, vol. 5, pp. 3445-3450.
Phan et al. (2009) Timing analysis of mixed time/eventtriggered multi-mode systems, IEEE Real-Time Systems Symposium (RTSS), pp. 271-280.
Phan et al. (2010) Compositional analysis of multi-mode systems, IEEE Euromicro Conference on Real-Time Systems (ECRTS), Jul. 6-9, 2010, pp. 197-206.
Phan et al. (2011) Towards a compositional multi-modal framework for adaptive cyber-physical systems, IEEE International Conference on Embedded and Real-Time Computing Systems and Applications, Aug. 28-31, 2011, pp. 67-73.
Poolsappasit et al. (2012) Dynamic Security Risk Management Using Bayesian Attack Graphs, IEEE Transactions on Dependable and Secure Computing, vol. 9, No. 1, pp. 61-74.
Prates et al. (2011) mixsmsn: Fitting finite mixture of scale mixture of skew normal distributions. Journal of Statistical Software, 54(12), 1-20.
Pycroft et al. (2016) Brainjacking: implant security issues in invasive neuromodulation, *World neurosurgery* 92, pp. 454-462.
Radcliffe (2011) Hacking Medical Devices for Fun and Insulin: Breaking the Human SCADA System, presentation at 2011 Black Hat Conf.
Rahmatian et al. (2012) Hardware-assisted detection of malicious software in embedded systems. IEEE Embedded Systems Letters (ESL), 4, 4, 94-97.
Ramilli et al. (2012) Always the same, never the same. IEEE Security & Privacy, 8, 2, 73-75.
Rao (2021) A Software Framework for Security Risk Assessment and Management in Life-critical Embedded Systems, PhD dissertation, University of Arizona.
Rao et al. (Apr. 2018) Trustworthy multi-modal framework for life-critical systems security, Annual Simulation Symposium, article No. 17, pp. 1-9.
Rao et al. (Apr. 2017) Composite risk modeling for automated threat mitigation in medical devices, In Proceedings of the Modeling and Simulation in Medicine Symposium, Virginia Beach, VA, USA, pp. 899-908.
Rao et al. (Aug. 2019) Resilient Security of Medical Cyber-Physical Systems, Database and Expert Systems Applications. DEXA 2019. Communications in Computer and Information Science, vol. 1062. Springer, Cham. https://doi.org/10.1007/978-3-030-27684-3_13.
Rao et al. (Jan. 2017) Probabilistic Threat Detection fo Risk Management in Cyber-physical Medical Systems, IEEE Software, IEEE, USA, vol. 35, No. 1, pp. 38-45, xp011674975, ISSN: 0740-7459, DOI: 10.1109/MS.2017.4541031.
Rao et al. (Oct. 2022) FIRE: A Finely Integrated Risk Evaluation Methodology for Life-Critical Embedded Systems. Information. 2022; 13(10):487. https://doi.org/10.3390/info13100487.
Reif et al. (2008) Anomaly detection by combining decision trees and parametric densities. Int. Conf. on Pattern Recognition, Tampa, FL, USA, pp. 1-4.
Roberts (2015) Intel: New Approach Needed to Secure Connected Health Devices, The Security Ledger.
Rose et al. (2015) The Internet of Things (IoT): An Overview, The internet society (ISOC), 80, 1-50.

(56) References Cited

OTHER PUBLICATIONS

Rostami et al. (2013) Heart-to-Heart (H2H): authentication for implanted medical devices, ACM SIGSAC conference on Computer & Communications Security, Nov. 4-8, 2013, pp. 1099-1112.
Sadeghi et al. (2015) Security and privacy challenges in industrial Internet of Things, 52nd ACM/EDAC/IEEE Design Automation Conference (DAC), Jun. 8-12, 2015, pp. 1-6.
Sametinger et al. (2015) Security Challenges for Medical Devices, Communication of ACM, 58(4), pp. 74-82.
Sametinger et al. (2016) Security scores for medical devices, Proceedings of the 9th International Joint Conference on Biomedical Engineering Systems and Technologies (BIOSTEC 2016), vol. 5: Healthinf, pp. 533-541.
Sametinger et al. (Dec. 2017) Resilient context-aware medical device security, International Conference on Computational Science and Computational Intelligence, Symposium on Health Informatics and Medical Systems (CSCI-ISHI), Las Vegas, NV, USA, Dec. 14-16, 2017, pp. 1775-1778.
Schölkopf et al. (1999) Support Vector Method for Novelty Detection, Advances in Neural Information Processing Systems , 12, pp. 582-588.
Sharif et al. (2007) Understanding precision in host based intrusion detection. In International Symposium on Research in Attacks, Intrusions and Defenses. 4637, 21-41.
Shim et al. (2000) Control system design for rotorcraft-based unmanned aerial vehicles using timedomain system identification, Proc. IEEE Int. Conf. Control Appl., pp. 808-813.
Singh et al. (2012) The Cardiac Pacemaker Case Study and its Implementation in Safety-Critical Java and Ravenscar Ada, Workshop on Java Technologies for Real-time and Embedded Systems (JTRES '12). Association for Computing Machinery, New York, NY, USA, 62-71.
Snell (Aug. 2017) Medical Device Cybersecurity Top Challenge to IoT Ecosystem, Health IT Security xtelligent Healthcare Media.
Song (2014) FPGA Implementation of a Support Vector Machine Based Classification System and Its Potential Application in Smart Grid, Int. Conf. Information Technology: New Generations (ITNG), pp. 397-402.
Sorber et al. (2012) An Amulet for trustworthy wearable mHealth, Proceedings of the Workshop on Mobile Computing Systems and Applications.
Sun et al. (2007) Digital Watermarking Based on Stochastic Resonance Signal Processor, *8th Pacific Rim Conference on Multimedia*, Hong Kong, China, Proceedings, pp. 367-375.
Symantec (2016) Medical Device Cybersecurity, Symantec Industry Focus: Medical Device Security, URL: www. symantec. com/content/dam/symantec/docs/data-sheets/symc-med-device-security-en.pdf.
Symantec (Apr. 2016) Internet Security Threat Report (ISTR), vol. 21.
Tax et al. (2004) Support vector data description. Machine Learning, 54(1): 45-66.
U.S. Department of Health and Human Service (Sep. 2017) Design Considerations and Premarket Submission Recommendations for Interoperable Medical Devices, Guidance for Industry and Food and Drug Administration Staff, U.S. Food and Drug Administration (FDA).
U.S. Department of Health and Human Services (Aug. 2017) Firmware Update to Address Cybersecurity Vulnerabilities Identified in Abbott's (formerly St. Jude Medical's) Implantable Cardiac Pacemakers: FDA Safety Communication, U.S. Food and Drug Administration (FDA).
U.S. Department of Health and Human Services (Oct. 2017) St. Jude Medical Recalls Implantable Cardioverter Defibrillators (ICD) and Cardiac Resynchronization Therapy Defibrillators (CRT-D) Due to Premature Battery Depletion—Update, U.S. Food and Drug Administration (FDA).
Verissimo et al. (2006) Intrusion-tolerant middleware: the road to automatic security, IEEE Security Privacy, vol. 4 (4), pp. 54-62.
Verizon (2016) State of the Market: Internet of Things. https://www.verizon.com/about/sites/default/files/state-of-the-internetof-things-market-report-2016.pdf.
Vert et al. (2004) A primer on kernel methods. Kernel methods in computational biology. Cambridge, MA: MIT press. p 35-70.
Vigliarolo (Mar. 2018) Bad user practices caused 41% of medical IoT security issues in 2017, Tech Republic.
Wagner et al. (2002) Mimicry Attacks on Host based Intrusion Detection Systems. Conf. on Computer and Communications Security, pp. 255-264.
Wasicek et al. (2014) Aspect-oriented Modeling of Attacks in Automotive Cyber-Physical Systems, Design Automation Conference, Jun. 1-5, 2014, pp. 1-6.
Weber (2010) Internet of Things—New security and privacy challenges, *Computer Law & Security Review*, vol. 26(1), pp. 23-30.
Weston et al. (2000) Feature selection for SVMs. Advances in neural information processing systems, 13.
Wilhelm et al. (2008) The Worst-Case Execution-Time Problem—Overview of Methods and Survey of Tools. ACM Transactions on Embedded Computing Systems, 7(36), pp. 1-47.
Williams et al. (2015) Cybersecurity vulnerabilities in medical devices: A complex environment and multifaceted problem, Medical devices (Auckland, NZ) vol. 8, pp. 305-316.
Xilinx Inc (2016) MicroBlaze Processor Reference Guide, UG984 (v2016.3).
Xu et al. (2011) IMDGuard: securing implantable medical devices with the external wearable guardian, IEEE INFOCOM.
Yoon et al. (2013) SecureCore: A Multicore-based Intrusion Detection Architecture for Real-Time Embedded Systems, 2013 IEEE 19th Real-Time and Embedded Technology and Applications Symposium (RTAS), Philadelphia, PA, USA, 2013, pp. 21-32.
Yoon et al. (2015) Memory heat map: Anomaly detection in real-time embedded systems using memory behavior. In Design Automation Conference, Jun. 8-12, 2015, 1-6.
Zhai et al. (2015) A method for detecting abnormal program behavior on embedded devices. IEEE Transactions on Information Forensics and Security 10, 8, 1692-1704.
Zhang et al. (2005) Anomalous Path Detection with Hardware Support, Conference on Compilers. Architectures and Synthesis for Embedded Systems, Sep. 24-27, 2005, pp. 43-54.
Zhang et al. (2013) MedMon: Securing medical devices through wireless monitoring and anomaly detection, IEEE Transactions on Biomedical Circuits and Systems, vol. 7, No. 6, pp. 871-881.
Zimmer et al. (2010) Time-Based Intrusion Detection in Cyber-Physical Systems, ACM/IEEE International Conference on Cyber-Physical Systems (ICCPS), Apr. 13-15, 2010, pp. 109-118.
Zion Market Research (May 2018) Cyber Security Market Size Will Reach $181.77 Bn by 2021: Zion Market Research.

\* cited by examiner (a) UAV structure

Task1 (T1): Navigation
Task2 (T2): Camera control
Task3 (T3): Image compression
Task4 (T4): AES encryption
Task5 (T5): Communication (b) RSM for the software tasks of UAV (a) Pacemaker structure (b) RSM for the software tasks of Network-connected Pacemaker Task1 (T1): Calculate URI and write log
Task2 (T2): Communicate with physician
Task3 (T3): Warming thread ISR1 (I1): Record atrial rate
ISR2 (I2): Pace atrium
ISR3 (I3): Pace ventricles
ISR4 (I4): Record ventricular rate

RUNTIME ADAPTIVE RISK ASSESSMENT AND AUTOMATED MITIGATION

CROSS-REFERENCE TO RELATED APPLICATIONS

This application is a U.S. National Stage Application filed under 35 U.S.C. § 371 of International Application No. PCT/US2019/059551, filed Nov. 1, 2019, which claims the benefit of U.S. Application No. 62/755,110, filed Nov. 2, 2018. Both of these applications are hereby incorporated by reference in their entireties.

STATEMENT REGARDING FEDERALLY SPONSORED RESEARCH OR DEVELOPMENT

This invention was made with government support under Grant No. 1615890, awarded by NSF. The government has certain rights in the invention.

BACKGROUND

The Internet of Things (IoT) represents the foundation of dramatic and widespread changes in cyber-physical systems (K. Carruthers, "Internet of Things and Beyond: Cyber-physical Systems," *IEEE Internet of Things Newsletter*, 2016). The rapid development and incorporation of Internet-connected devices in our lives has been possible due to advancements in computational resources, sensors, and networking capabilities (Rose et al., "The Internet of Things (IoT): An Overview," *Internet Society*, 2015). Unsurprisingly, IoT is strongly influencing advances in healthcare and medical devices. Such devices are now part of a digital health ecosystem (Krishnamurthy et al., *Cognizant* 20-20 *Insights, Cognizant*, 2016), providing continual patient monitoring and services, interoperability, and real-time data access, as illustrated in FIG. 1.

Within this ecosystem, life-critical medical devices, including implantable pacemakers and wearable insulin pumps, are essential to preserving patients' health, well-being, and life. Non-life-critical devices (e.g., fitness trackers and smartphones) also provide data on daily habits to assist users in maintaining their general health (P. Roberts, "Intel: New Approach Needed to Secure Connected Health Devices", URL: www.securityledger.com/2015/03/intel-new-approach-needed-to-secure-connected-health-devices/, *The Security Ledger*, 2015). These medical IoT systems use various communication methods (e.g., Wi-Fi, Bluetooth) to enable remote monitoring of patients, to support real-time data analysis by healthcare providers, to assist physicians with diagnosing health problems, and to enable remote updates/configurations of device parameters (D. V. Dimitrov, *Healthcare Informatics Research* 22.3, 156-163, 2017).

With a wide attack surface across the entire healthcare ecosystem, security of medical devices is a critical concern among all stakeholders (Symantec Industry Focus: Medical Device Security, "Medical Device Cybersecurity", URL: www.symantec.com/content/dam/symantec/docs/data-sheets/symc-med-device-security-en.pdf", *Symantec*, 2016; Burleson et al., *Design Automation Conference (DAC)*, pp. 12-17, 2012; and Williams et al., *Medical Devices* (Auckland, N.Z.), 305-316, 2017). With their pervasive network access, medical IoT systems face numerous and wide ranging security and privacy threats that must be addressed throughout the entire lifecycle from design and development to deployment and long-term maintenance. Medical devices are complex embedded systems with, often, limited resources that present several challenges in balancing the needs for security, safety, privacy, and regulatory compliance (Bandyopadhyay et al., *Wireless Personal Communications* 58.1, 49-69, 2011; R. H. Weber, *Computer Law & Security Review*, Vol. 26, Issue 1, 23-30, 2010; Miorandi et al., *Ad Hoc Networks*, Vol. 10, Issue 7, 1497-1516, 2012; and Sametinger et al., *Communications of the ACM*, 58(4), pp. 74-82, 2015).

Regulatory guidance may manage exposure to security risks and vulnerabilities during design and deployment but is not sufficient to fully secure medical devices throughout their lifecycle (see U.S. Department of Health and Human Service, "Postmarket Management of Cybersecurity in Medical Devices", URL: www.fda.gov/downloads/medicaldevices/deviceregulationandguidance/guidancedocuments/ucm482022.pdr, *U.S. Food and Drug Administration (FDA)*, 2016; and U.S. Department of Health and Human Service, Center for Devices and Radiological Health, and Center for Biologics Evaluation and Research, "Content of Premarket Submissions for Management of Cybersecurity in Medical Devices", URL: www.fda.gov/downloads/medicaldevices/deviceregulationandguidance/guidancedocuments/ucm356190.pdf, *U.S. Food and Drug Administration (FDA)*, 2014).

Additionally, while proactive methods to secure systems during the design stage by minimizing vulnerabilities and utilizing secure protocols are essential, the likelihood of zero-day threats cannot be ignored (Chen et al., *IFIP International Conference on Communications and Multimedia Security*, Vol. 8735, pp. 63-72, 2014; and Kartik et al., *IEEE International Conference Pervasive Computing and Communication Workshops (PerCom Workshops)*, 2016). Several efforts have demonstrated how vulnerabilities in several life-critical medical devices can be exploited to perform life-threatening hacks, including attacking pacemakers and implantable cardiac defibrillators. Examples, include a life-threatening stimulus to a patients' heart (Halperin et al., *IEEE Symposium on Security and Privacy*, 2008; and Hanna et al., *USENIX Conference on Health Security and Privacy*, 2011), attacking an insulin pump to inject a fatal dose of insulin (Li et al., *IEEE International Conference on e-Health Networking, Applications and Services*, pp. 150-156, 2011; and J. Radcliffe, *Black Hat Conference Presentation Slides*, 2011), and hijacking neurological implants (Pycroft et al., *World neurosurgery* 92, pp. 454-462, 2016).

Furthermore, current approaches to deal with vulnerabilities in medical devices are costly, lengthy, and leave patients vulnerable. As recently as August 2017, the FDA recalled more than 465,000 implantable cardiac devices after detecting vulnerabilities that could allow an attacker to reprogram the pacemakers, and recalled 175,000 implantable cardiac defibrillators due to vulnerabilities that could lead to premature battery depletion (U.S. Department of Health and Human Services, "Firmware Update to Address Cybersecurity Vulnerabilities Identified in Abbott's (formerly St. Jude Medical's) Implantable Cardiac Pacemakers: FDA Safety Communication", URL: www.fda.gov/MedicalDevices/Safety/AlertsandNotices/ucm573669.htm", *U.S. Food and Drug Administration (FDA)*, 2017; and C. Morris, "465,000 Pacemakers Recalled on Hacking Fears", URL: fortune.com/2017/08/31/pacemaker-recall-fda/, *FORTUNE*, 2017). Correcting these problems requires either a physician visit to update the device software or surgery for immediate explant and replacement (U.S. Department of Health and Human Services, "St. Jude Medical Recalls Implantable Cardioverter Defibrillators (ICD) and Cardiac Resynchronization Therapy Defibrillators (CRT-D) Due to Premature Battery Depletion—Update", URL: www.fda.gov/MedicalDevices/Safety/AlertsandNotices/ucm573669.htm, *U.S. Food and Drug Administration (FDA)*, 2017). The economic impact of these recalls is enormous. The recent pacemaker recall alone may cost $3 billion, and studies have estimated the yearly costs of medical device recalls at $2.5 to $5 billion (Fuhr et al., *McKinsey Center for Government*, 2013). Of great concern is that while patients are awaiting software updates or replacement, their medical devices remain vulnerable, which aggravates the severity of the situation.

In view of the above, what is needed are medical devices designed to support runtime mitigation schemes capable of identifying software security threats and safely reconfiguring the device's operation to mitigate the threat, during which the utmost concern is ensuring the continuity of life-critical operations.

SUMMARY OF THE INVENTION

Incorporating network connectivity in cyber-physical systems (CPSs), Internet of Things (IoT), and embedded systems has led to advances yielding better healthcare and quality of life for patients. However, such advances come with the risk of increased exposure to security vulnerabilities, threats, and attacks. Numerous vulnerabilities and potential attacks on these systems have previously been demonstrated. Accordingly, CPS, IoT, and embedded system software and devices have to be designed and developed with security as a key consideration by enforcing failsafe modes, ensuring critical functionality and risk management. This invention provides operating modes, risk models, and runtime threat estimation for automatic switching to fail-safe modes when a security threat or vulnerability is detected.

The present invention provides life-critical systems, specifically medical CPS, IoT, and embedded devices, having runtime adaptive risk assessment and mitigation capabilities. The invention provides methods and systems able to assess the risk of vulnerabilities and threats at runtime, including but not limited to threats to the operational software of the device, and develop automatic mitigation methods to reduce the risk.

In an embodiment, risk assessment and mitigation methods are achieved by reconfiguring the device to operate in a different operational mode that will isolate threats by disabling the affected system components. In an embodiment, the invention comprises one or more of the following:

i. A multi-modal software design approach that yields adaptive software implementation in which operational modes have monotonically increasing composite system risk. The approach models the individual risk of accessing, controlling, or configuring system components (e.g., sensors, actuators, patient data) and to automatically calculate the risk of operational modes;

ii. Risk models dynamically calculate risk levels based on the system's operational mode and detected threats. More specifically, to support an accurate and fine-grained adaptive risk model, the method non-intrusively detects potential threats, isolates the threat to specific hardware or software components, and estimates the threat probability;

iii. Runtime mitigation methods automatically change the operational mode when the composite risk of the current operational mode or the individual risk of software/hardware components exceeds pre-defined risk thresholds; and iv. A secure system architecture and middleware controls access to life-critical system components and implement the adaptive, risk-based automated mitigation.

In an embodiment, the present invention provides a system for detecting and mitigating malware in a device, said system comprising:
a) said device having one or more sensors or actuators, and a computer processor able to operate said sensors or actuators, wherein the device is able to be connected to a network or external computer system;
b) a first module implemented on the computer processor able to operate said one or more sensors or actuators in a base operational mode and operate said one or more sensors or actuators in one or more higher operational modes;
c) a second module implemented on the computer processor able to estimate a probability that a malware risk will effect a function performed by said one or more sensors or actuators in said one or more higher operational modes;
d) an optional third module implemented on the computer processor able to model normal system behavior of the base operational mode and one or more higher operational modes of the device, compare current system operation to the modeled normal system behavior, and estimate a probability of the current system operation being affected by malware based on performance deviation between the current system operation and the modeled normal system behavior; and
e) a fourth module implemented on the computer processor able to analyze the estimated probabilities from the second and third modules and cause the first module to switch from the one or more higher operational modes to a higher operational mode having less functionality or to the base operational mode when the estimated probabilities exceed a calculated risk threshold.

Preferably, the system further comprises the third module. The modules may be software modules and/or hardware modules. Optionally, the first, second, third and fourth modules are each a software module. In an embodiment, the second and third modules, independently from one another, are a software module or hardware module.

As used herein, "malware" refers to software that disrupts or damages the intended function of a computer system, or provides unauthorized access to the computer system. Often, the malware is intentionally designed to cause the disruption or damage or to provide the unauthorized access. In embodiments provided herein, the computer system is specifically a medical device or cyber-physical system. Optionally, the medical device or cyber-physical system is implanted within a patient. Alternatively, the medical device or cyber-physical system is a wearable device or system. For example, the one or more sensors or actuators are able to monitor a biological function in a patient, administer a drug to the patient, administer an electric pulse to the patient, or combinations thereof. In an embodiment, the device is an insulin pump which administers insulin to a patient, or is a pacemaker which administers an electrical pulse to a patient.

As used herein, a "base operational mode" refers to a mode of operation of a device, preferably a medical device, that performs a basic level of functionality necessary in order for the device to function. For example, in an embodiment, the base operational mode performs only essential functions of the device. Preferably, a device or component of a device in a base operational mode also has little to no interaction with a network or computer system outside of the device, and is therefore is less at risk of being affected by malware. In contrast, a "higher operational mode" refers to a mode of operation of a device having increased functionality compared to the base operational mode and, optionally, increased connectivity with an outside network or computer system. In an embodiment, a device has multiple higher operational modes, where each higher operational mode has greater or lesser functionality compared to another higher operational mode.

Preferably, software able to operate one or more sensors or actuators in the base operational mode is implemented on a different region of the computer processor than software able to operate the one or more sensors or actuators in the one or more higher operational modes. As a result, if the software operating the higher operation modes is damaged, compromised, or infected with malware, the software operating the base operational mode will be unaffected. In an embodiment, in order to further insulate the base operational mode, the system further comprises middleware software implemented on the computer processor able to transfer data from the software able to operate the base operational mode and other software implemented on the computer processor.

In an embodiment, the present invention provides a method for detecting and mitigating malware in a medical device able to be connected to a network or external computer system, said method comprising the steps of:

a) operating one or more sensors or actuators of said device in a base operational mode and one or more higher operational modes;
b) estimating a probability that a malware risk will effect a function performed by said one or more sensors or actuators in said operational modes; and
c) analyzing the estimated probabilities from step b) and switching from one or more higher operational modes to a higher operational mode having less functionality or to the base operational mode when the estimated probabilities exceed a calculated risk threshold.

Preferably, the method further comprises: step d) modeling normal system behavior of the operational modes of the device, comparing current system operation to the modeled normal system behavior, and estimating a probability of the current system operation being affected by malware based on performance deviation between the current system operation and the modeled normal system behavior. The analyzing step further comprises analyzing the estimated probabilities from steps b) and d) and switching from one or more higher operational modes to base operational mode when the estimated probabilities exceed a calculated risk threshold.

Optionally, the method further comprises the step of transferring data from software operating the base operational mode to other software implemented on a computer processor of the device through secured middleware software implemented on the computer processor.

In an embodiment, the method further comprises continuously updating the estimated probability that the malware risk will effect functions performed by said one or more sensors or actuators during operation of the device.

Preferably, the modeling step (step d)) comprises analyzing timing samples within a fixed-size execution window, comparing cumulative distribution functions (CDFs) of the execution window against the modeled normal system behavior, and estimating the probability of the current system operation being affected by malware.

In an embodiment, the method further comprises performing a static risk evaluation, performing a dynamic risk evaluation during operation of the device, or both, and determining the calculated risk threshold, estimated probabilities, or both, based on the risk evaluations. In a further embodiment, performing a static risk evaluation comprises assigning calculated security-health and security-data-sensitivity scores to tasks performed by each operational mode of the device, calculating a task risk score for each of said tasks, and establishing static risk thresholds for each operation mode based on accumulated task risk scores. During operation of the device, dynamic threat probabilities are calculated for individual operations performed by each operational mode, and dynamic mode risk scores are calculated for each operational mode based on accumulated dynamic threat probabilities. Preferably, the method further comprises analyzing the static risk thresholds and dynamic mode risk scores for each operation mode during operation of the device, and switching from risky operation modes, where the dynamic mode risk scores are outside selected static risk thresholds, to safe operation modes where the dynamic mode risk scores are within selected static risk thresholds.

Thus, the systems and methods of the present invention substantially advance the state-of-the-art by enabling fast and accurate runtime detection and assessment of threats, and providing formal and rigorous methods to mitigate life-threatening intrusions while preserving the life-critical operations of the device.

DETAILED DESCRIPTION OF THE INVENTION

Overview

Advancements in computational resources, sensors, and networking capabilities have led to the widespread incorporation of Internet-connected devices in everyday life. These developments have also strongly influenced advances in healthcare and medical devices. Continual patient monitoring and services, interoperability, and real-time data access has become a normality. Life-critical devices, including but not limited to implantable pacemakers and wearable insulin pumps, are essential for patients' health, well-being, and life. However, such devices pose additional security challenges in addition to those being considered for regular information technology. This is particularly exacerbated due to communication methods like Wi-Fi or Bluetooth that enable remote monitoring, real-time data analysis, and remote updates and configurations of device parameters.

With the rise of internet transactions and systems, cybersecurity is needed to prevent hacking or malware. There is a need for a technology that automatically disables systems that are affected by cyber attacks, in order to automatically prevent risk. In particular, healthcare related devices are advancing due to the internet of Things (IoT) and advances in technology. The security of both life-critical and non-life-critical devices has become of increased importance to insure a patient's medical information is safe as well as the patient themselves remains safe. As more life-critical, medical, IoT devices become available, attacks such as attacking pacemakers, insulin pumps, and neurological implants need to be mitigated.

Accordingly, the present invention provides methods and a multi-modal software and system security framework for life-critical and safety-critical devices, specifically medical cyber-physical systems (CPSs), Internet of Things (IoT) devices, and embedded systems. These methods and systems assess risks, vulnerabilities, and threats and then implements automated mitigation techniques when necessary. The present invention has applications, particularly for medical systems and devices, in terms of risk management, system security, threat detection. The software and systems of the present claims also provide improved adaptability, improved versatility, increased safety, and lower risk.

Figure 2:
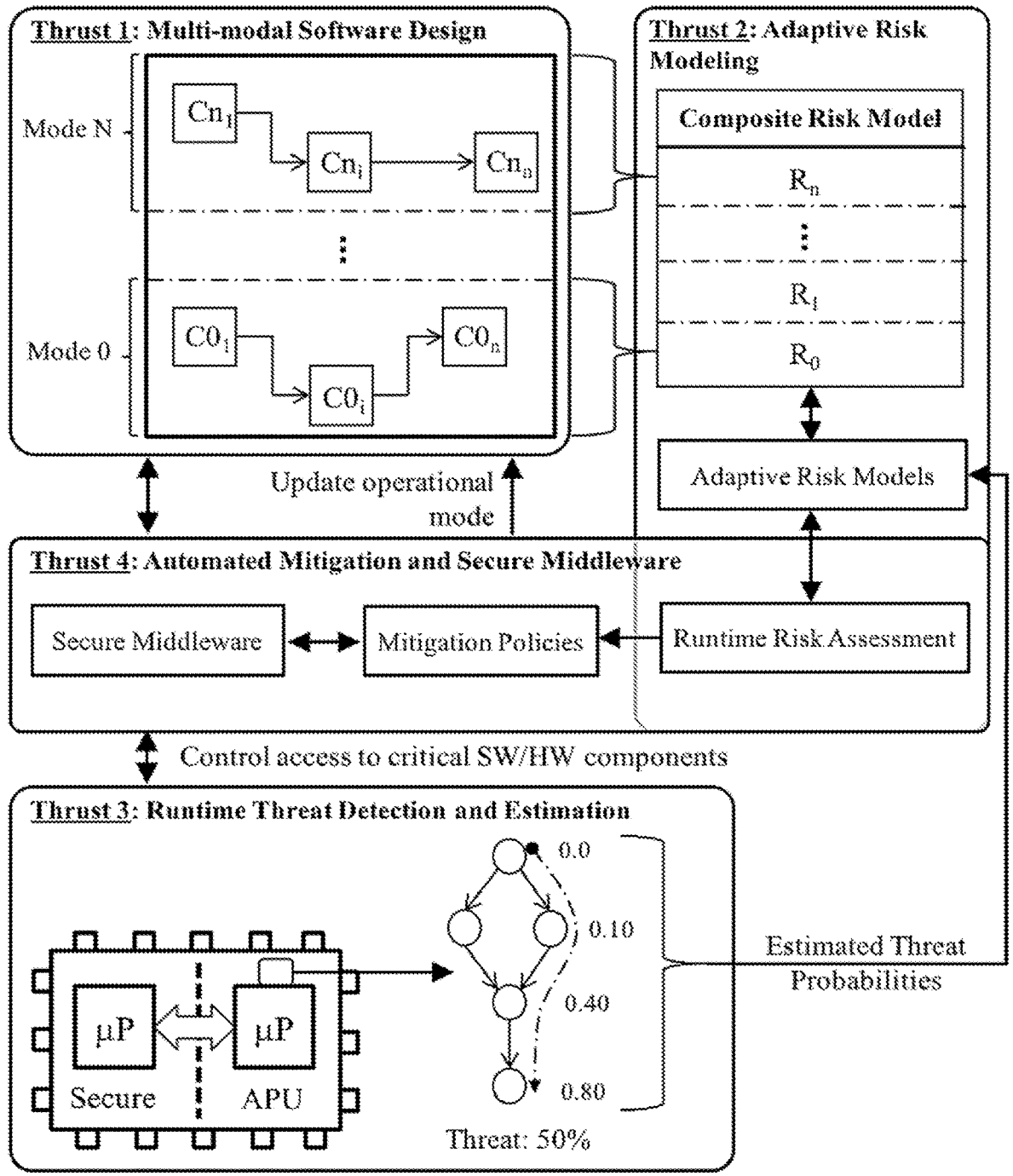
FIG. 2 shows four main components for runtime adaptive risk assessment and threat mitigation in life-critical systems in an embodiment of the present invention.

FIG. 2 provides an overview of four main components in an embodiment of the invention. The systems and methods of the present invention preferably comprise at least one or more of these components, although an integrative framework is envisioned, where each component is indispensable in accomplishing the goal of securing life-critical systems. The components' interdependence is depicted in the figure and described in detail below.

Component 1: Multi-Modal Software Design. In an example, this component constructs models and defines behaviors based on expected behaviors by connecting with Component 4 to access the system resources such as sensors and actuators as well as data gathered by the systems. An overarching multi-modal software design approach is described that defines software as several operational modes, each operational mode having monotonically increasing system risk. Thus, operational modes range from a base operational mode (Mode 0) that only implements life-critical operations with minimal risk to the highest operational mode (Mode N) with the highest system functionality that comes with the highest system risk. The proposed multi-modal software design approach utilizes the secure middleware (Component 4) to access critical system resources (e.g., sensors, actuators) and sensitive data (e.g., patient data, device configuration). Methods to assess an operational mode's base system risk and construct formal models that define expected system behavior are employed.

Component 2: Adaptive Risk Modeling. This component utilizes formal and statistical methods to analyze and update risks, and also estimates the probability that a risk will affect a certain function or task. Formal risk models capture the base system risk as a function of the component, data, operation, and access type. The risk models both enable the risk assessment of specific operations by the medical device (e.g., reading a cardiac sensor) and the composite risk of each operational mode. Risk modeling supports adaptive risk assessment that dynamically updates the risk of operations, tasks, and modes based on the runtime threat detection. Specifically, formal and statistical methods are used to update risk across the component, data, operation, and access type models given an estimated probability of a threat affecting a specific operation/task within the current operational mode.

Component 3: Runtime Threat Detection and Estimation. To automatically detect system threats, a statistical approach for modeling the normal system behavior of operational modes using cumulative distribution functions (CDF) of timing data and execution sequences has been developed. Runtime detection, using non-intrusive observation methods, analyze the system execution to assess the compliance with the normal system behavior model. This approach uses a probabilistic formulation to estimate the presence of a threat affecting individual operations and sequences of operations. To ensure rapid detection, the runtime detector analyzes timing samples within a fixed-size execution window, compare the CDFs of the execution window against the normal system model, and estimate the probability of a threat.

Component 4: Automated Threat Mitigation and Secure Middleware. This component uses the above components to categorize threats as minor or severe, and using risk thresholds, changes operational modes when essential to mitigate threats. The automated threat mitigation uses the adaptive risk models and runtime threat detection to decide when changing operational modes is essential to mitigate potential threats or vulnerabilities. The resulting mitigation approach distinguishes between severe threats requiring immediate mitigative actions and minor threats that can allow delayed mitigative actions. A central component of the automated mitigation is the specification of risk thresholds, which are used to determine the appropriate operational mode for the current cumulative system risk. To support the proposed framework, a secure middleware and embedded architecture separates the low-level access to life-critical components from the high-level software for each operational mode. The secure middleware acts as an intermediary between these components and within the secure enclave implements the dynamic risk assessment and automated mitigation.

The above framework supports the specifications of mitigation policies for controlling the critical transition between operational modes, which enables the analysis of total latency from threat detection to mitigation.

EXAMPLES

Example 1—Limitations of the State-of-the-Art in Secure Medical Devices

Several works have been proposed for ensuring safety and security in medical devices, in broad areas of risk management, hardware devices, formal modeling and verification, and security schemes (Xu et al., *IEEE INFOCOM*, 2011; Zhang et al., *IEEE Transactions on Biomedical Circuits and Systems*, 2013; Sorber et al., *Proceedings of the Workshop on Mobile Computing Systems and Applications*, 2012; Li et al., *IEEE Embedded Systems Letters*, 2013; Jiang et al., *Found. Trends Electron. Des. Autom.* 9, pp. 309-391, 2015; and Rostami et al., *ACM SIGSAC conference on Computer & Communications Security*, pp. 1099-1112, 2013). These proposed defenses require additional hardware to be worn by the patient or involve biological authentication schemes requiring further processing. However, security must be deeply integrated in the design of software for medical devices. Suitable mitigation schemes have to be incorporated in order to dynamically mitigate the risk during deployment. Such research has been conducted distinctly (but not integratively) in several aspects of embedded systems as described below.

Runtime Anomaly Detection

Much work exists in real-time threat assessment and management, especially in intrusion detection systems (Blyth et al., *J. Computer Security*, Vol. 14, pp. 513-534, 2006; and Cherdantseva et al., *Computers and Security*, Vol. 56, pp. 1-27, 2016). Probabilistic methods such as Markov models are popularly utilized to detect threats in such systems (Ames et al., *Lecture notes in computer science*, pp. 145-164, 2006). However, in critical medical cyber-physical systems that are characterized by timing constraints, expeditious and robust threat detection is key (Lu et al., *Asia and South Pacific Design Automation Conference*, pp. 809-814, 2015; and Lu et al. *Proceedings of the WESS'15: Workshop on Embedded Systems Security*, 2015). This necessitates the analysis of the distribution of events in a single execution window as compared to the current state sample as in Markov models. In the present example, cumulative distribution functions (CDF) were utilized for modeling the normal device behavior that is used to quantify the likeliness of security threats at runtime (Rao et al., *IEEE Software*, Vol. 35, pp. 38-43, 2017).

Several previous efforts for malware detection in embedded systems have used timing information within anomaly-based detection methods. Patel et al. (*IEEE Transactions on Very Large Scale Integration (VLSI) Systems*, No. 99, pp. 1-14, 2010) presented a fine-grained intrusion detection method that monitors the execution sequence and execution time of each basic block using a control flow map. However, this incurs a performance overhead of up to 44%. For life-critical systems, such detrimental impact on the performance of the software application is often infeasible or prohibitive. Zimmer et al. (*ACM/IEEE International Conference on Cyber-Physical Systems (ICCPS)*, pp. 109-118, 2010) proposed a timing-based intrusion detection system at the granularity of function calls and return paths. This approach makes decisions based on individual operations, instead of considering entire execution paths. This can lead to a high number of false positives. Yoon et al. (*Real-Time and Embedded Technology and Applications Symposium (RTAS)*, 2013) presented SecureCore, which measures the execution time of basic blocks and estimates the probability of that timing value from a statically determined timing distribution. If that probability is less than a specified threshold (e.g., 5%), SecureCore flags the execution as malicious. High false positive rates are inherent in this approach, as timing values of normal execution that have low probability are intentionally marked as malicious.

Previous work developed a nonintrusive runtime anomaly detection hardware that monitors the best-case execution time (BCET) and worst case execution time (WCET) of individual operations within a software application (Lu et al., *Asia and South Pacific Design Automation Conference*, pp. 809-814, 2015; Lu et al., *Proceedings of the WESS'15: Workshop on Embedded Systems Security*, 2015; and Lu and Lysecky, *ACM Transactions on Embedded Computing Systems (TECS)*, Vol. 17(2), pp. 1-27, 2017). Although this approach can detect malware efficiently, it independently makes decisions based on individual operations without considering statistical characteristics of execution timing. By only considering the BCET and WCET of individual events, the timing variability of those events presents challenges in accurately training the model to achieve low false positives.

While previous efforts have made excellent advances in threat detection, none specifically use statistical properties of execution windows, sufficiently minimize false positive rates, monitor complete execution paths or tasks, or provide an estimate of the probability of a threat. In contrast, the present approach in this example attempts to minimize the false positive rate, maintain a high detection rate, consider complete execution paths, and provide a quantitative estimate of probability of malware.

Multi-Modal Software Design

Modal implementations have been used in embedded systems ranging from cyber-physical systems, network routers, to life-critical systems. The main goal of using multiple modes in previous work has been to dynamically adapt the system to different algorithms, controllers, resource demands, or unexpected scenarios. Oh and Ha (*Proceedings of the Tenth International Symposium on Hardware/Software Codesign (CODES)*, pp. 133-138, 2002) proposed a hardware/software co-synthesis methodology for multi-modal embedded systems that maps function modules to processing elements for real-time scheduling constraints. A mode is comprised of tasks, which in turn contain functional blocks that are mapped either to software or hardware to meet task deadlines. A significant body of work has focused on design and analysis of multi-mode frameworks for adaptive cyber-physical systems (Phan et al., *IEEE International Conference on Embedded and Real-Time Computing Systems and Applications*, pp. 67-73, 2011; Phan et al., *IEEE Euromicro Conference on Real-Time Systems (ECRTS)*, 2010; and Phan et al., *IEEE Real-Time Systems Symposium (RTSS)*, pp. 271-280, 2009).

Phan et. al. (*IEEE International Conference on Embedded and Real-Time Computing Systems and Applications*, pp. 67-73, 2011; and *IEEE Real-Time Systems Symposium (RTSS)*, pp. 271-280, 2009) models systems as multiple mode components and interfaces to facilitate efficient resource usage, incremental integration and adaptivity. Each mode of a multi-modal application consists of different tasks, arrival rates or scheduling policy. Tasks are independent and are characterized by parameters representing the needs for schedulability and resource usage. Mode change protocols are assumed to be either event or time triggered.

Most of the prior research in multi-modal frameworks has focused on modeling and analyzing systems/applications to efficiently use resources and ensure schedulability of tasks. The present focus, on the other hand, is to design multi-modal applications for life-critical devices to ensure security by tightly integrating a risk model that assigns composite risk values to each mode. The application is composed of modes of increased operational functionality with a monotonically increasing order of risk.

Example 2—Resilient Security of Medical Cyber-Physical Systems

The present example provides resilience in cyber-physical systems (CPSs) by designing such systems to have multiple modes, by modeling risk, by adaptive update of these risks, and eventually by automatic mitigation schemes.

Multi-Modal Design

Application software is first designed for medical CPSs in a multi-modal fashion, where the system can operate in only one mode at a time (Phan et al., *IEEE International Conference on Embedded and Real-Time Computing Systems and Applications*, pp. 67-73, 2011; and Rao et al., *Annual Simulation Symposium*, article no. 17, pp. 1-9, 2018). To ensure critical functionality of the medical device, the system has one essential mode that runs with a minimal attack surface. Each mode consists of a set of tasks to be performed by that mode, where a task would represent the implementation thread. In the essential mode, the tasks performed are the critical ones required for the essential functionality of the system. Different modes can have tasks in common based on the functionality.

Adaptive Risk Modeling

Risk modeling is a central activity in order to ensure security of systems (National Institute of Standards and Technology: Guide for Conducting Risk Assessments, *NIST Special Publication* 800-30 *Revision* 1, September 2012). A risk model is deeply integrated into the multi-modal software model by associating risk values at every hierarchical level of the mode to provide robust risk assessment and management (Rao et al., *Proceedings of the Modeling and Simulation in Medicine Symposium*, Virginia Beach, VA, USA, pp. 899-908, 2017). During the deployment of the device, risks of the operations are assessed and updated based on the threats detected and estimated threat probabilities of the operations. The threat detector in this example is implemented in hardware and focuses on monitoring and analyzing the timing of the internal operations of the target system by utilizing a sliding window (Lu et al., *ACM Trans. Embed. Comput. Syst.*, 17(2), 38:1-38:27, 2018). At runtime, the timing samples inside each sliding window are analyzed, and the probability of the current execution being malicious (threat probability) is calculated. In addition to the proposed risk update in Rao et al. (*IEEE Softw.*, 35(1), 38-43, 2018), an additional risk update condition is provided for impactful operations.

Impactful operations are defined as operations whose base risk is beyond an impact threshold that would directly affect the critical functionality of the system. The risk update is exponential for these operations as compared to an additive increase as proposed in Rao et al. (*IEEE Softw.*, 35(1), 38-43, 2018).

Threat Estimation

For runtime risk assessment, risk values need to be updated in a composite risk model. If security threats are detected with estimated threat probabilities, risk values can be updated accordingly, depending on the estimated security threat probabilities. Initial composite risks to the modes are assigned based on their composition of tasks or task options that constitute the modes. For example, initial operation risks can be assigned based on security scores as proposed in (Sametinger et al., *Proceedings of the 9th International Joint Conference on Biomedical Engineering Systems and Technologies (BIOSTEC* 2016), Vol. 5: HEALTHINF, pp. 533-541, 2016).

Automatic Mitigation Schemes

In many domains, including health, risks have arisen through the addition of software and connectivity. Attack vectors that did not previously exist have suddenly become a priority (Biro et al., *IEEE Softw.*, 35(1), 24-29, 2018). To ensure risk management during deployment of the device, an automatic mitigation scheme is also provided that changes operating modes of the system triggered by updates in risk values in order to reduce the effective risk of the system. The system risk is the risk of the current operating mode. A system level risk threshold is defined by an expert that represents the level beyond which the system cannot operate in the current operating mode. It is assumed that during initial deployment the system always operates in the highest mode, thus, having full functionality and connectivity to the outside world.

Architectural Overview

Figure 1:
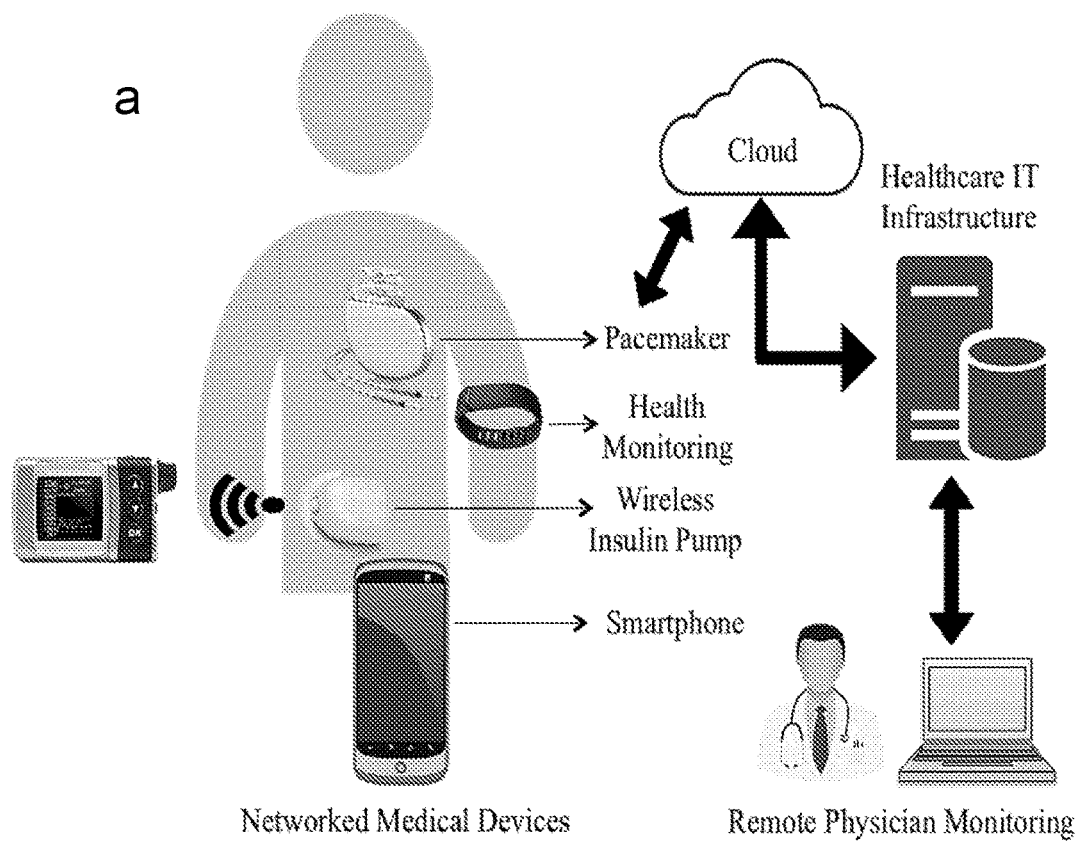
FIG. 1 shows an exemplary schematic of Integration of IoT devices within a digital health ecosystem (panel a), and illustrates an architectural overview of a cyber-physical system having a multi-modal design (panel b).
Figure 1:
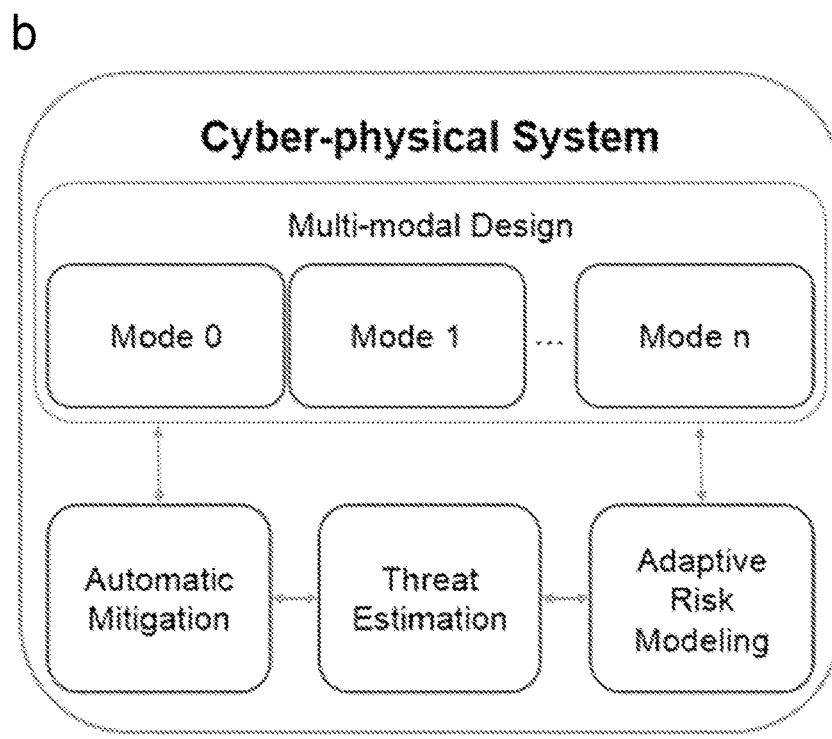

FIG. 1, panel b, gives an overview of the components of a secured cyber-physical system, where various modes are available that are switched depending on the risk assessment. Depending on the determination of risks, threat estimations will lead to mitigation activities that have an effect on the operation of the CPS by means of switching the modes. The modes have common functionalities, but the lower the mode number, the more restrictive are activities that may lead to security problems. For example, in the essential Mode 0, a CPS will only provide basic functionality with any communication turned off that is not absolutely necessary for basic functioning. Thus, Mode 0 will have the smallest attack surface possible, while Mode n will provide full functionality of the system with the biggest attack surface.

Insulin Pump

The architectural overview has been evaluated with different insulin pump scenarios. The attacks in these scenarios are based on known malware that are adapted to the insulin pump model. For example, the Fuzz malware is a common attack by malicious users, with the purpose of interfering with the predefined functionality of the target system by "fuzzing", or slightly altering the data. The Information Leakage malware is another well-known attack, with the goal of breaking confidentiality by extracting information from the patient and transmitting it to an unauthorized user. The same configuration is used for all simulations. The starting point of the simulations will be the highest functionality mode, and the system is evaluated on its ability to adapt to different threat scenarios and whether these adaptations are effectively able to mitigate the threats.

Conclusion

CPSs pose many security threats. In addition to considering security issues during development from the very beginning, these systems must be capable of reacting to threat scenarios not yet known during development. Software updates are a means of adapting systems in such scenarios. However, for CPSs, updates and patches are not always practicable. For such cases, resilience mechanisms with a multi-mode design, adaptive risk updating, and an automatic mitigation scheme provide an effective solution.

Example 3—Trustworthy Multi-Modal Framework for Life-Critical Systems Security

With the advent of network connectivity and complex software applications, life-critical systems like medical devices are subject to a plethora of security risks and vulnerabilities. Security threats and attacks exploiting these vulnerabilities have been shown to compromise patient safety by hampering essential functionality of the system. This necessitates incorporating security from the very design of software. Isolation of software functionality into different modes and switching between them based on risk assessment, while maintaining a fail-safe mode ensuring device's essential functionality has been shown to be a compelling design. Formal modeling is an essential ingredient for verification of such a design.

This example describes a trustworthy multi-modal framework for life-critical systems security and in turn safety. This example also describes a multiple mode based software design approach of operating such systems with a fail-safe mode that maintains critical functionality. Trustworthiness is ensured by formalizing a composite risk model incorporated into the design for run-time risk assessment and management.

Introduction

Life-critical systems especially medical devices have been composed of complex hardware and software. With networking and interoperability capabilities, such systems provide a wide range of convenient features being classified under the umbrella of Internet of Things (IoTs). Augmented with networking capabilities the possibilities of vulnerabilities are eminent, providing a potential for a wide attack surface for cybersecurity threats. Security and privacy have become critical concerns in recent times (Sadeghi et al., 52nd *ACM/EDAC/IEEE Design Automation Conference (DAC)*, pp. 1-6, 2015) (Williams and Woodward, *Medical devices* (Auckland, NZ) vol. 8, pp. 305, 2015; and Hossain et al., *IEEE World Congress on Services*, pp. 21-28, 2015).

Security and privacy threats must be addressed throughout the lifecycle from design and development to deployment and maintenance. Life-critical systems have limited resources that present several challenges in balancing the needs for security, safety, privacy, and regulatory compliance (R. H. Weber, *Computer Law & Security Review*, Vol. 26(1), pp. 23-30, 2010; Sametinger et al., *Communications of the ACM*, Vol. 58(4), pp. 74-82, 2015; and Miorandi et al., *Ad Hoc Networks*, Vol. 10(7), 1497-1516, 20122012).

In order to proactively and robustly manage security vulnerabilities and threats, risk management and assessment has emerged as the tangible solution ("Guidance for the Content of Premarket Submissions for Software Contained in Medical Devices", *U.S. Food and Drug Administration (FDA)*, 2005; and "Postmarket Management of Cybersecurity in Medical Devices", *U.S. Food and Drug Administration (FDA)*, 2016). Suitable mitigation schemes to reduce potential risk and sustain essential functionality of the life-critical system during deployment are required. System hardening has been a promising security remedial approach for such systems involving isolation of critical functionalities into fail-safe modes from "other" functionalities (Sametinger et al., *Communication of ACM*, 58(4), pp. 74-82, 2015; and Almohri et al., *IEEE/ACM International Conference on Connected Health: Applications, Systems and Engineering Technologies (CHASE)*, pp. 114-119, 2017).

Life-critical systems are adaptive systems that operate in multiple modes based on environmental and system conditions. Each mode represents a different device operational state that is characterized by a unique set of resource configurations and tasks. These modes mainly facilitate with efficient use of resources, adaptability, schedulability and system configurability. Mode switches are either event or time triggered reflecting system or environmental changes. These systems are often accompanied by adaptive software/ middleware to orchestrate the modifications based on respective parameters. Such systems become quickly complex and require model-driven and formal modeling approaches to verify functional and behavioral operation.

Towards this direction, previous work proposed a multi-modal secure design framework with a composite risk model for automatic threat mitigation during system deployment (Rao et al., *Proceedings of the Symposium on Modeling and Simulation in Medicine, MSM '17*, pp. 9:1-10, 2017; and Rao et al., *IEEE Software*, Vol. 35, pp. 38-43, 2017). The framework incorporates abstracting of hardware and corresponding software into different modes based on potential risk and functionality. Mode change decisions are triggered by changes in composite risk values handled by a middleware. With hardware security support provided by technologies like ARM's TrustZone® (ARM Security Technology, ARM Limited, Available infocenter.arm.com/help/topic/com.arm.doc.prd29-genc-009492c/PRD29-GENC-009492C_trustzone_security_whitepaper.pdf, 2005-2009), it is apparent that the multi-modal framework with risk modeling must be software driven with accompanying middleware for mitigation decisions.

Formal modeling approaches are required to understand the behavior and functioning of the system under such a multi-modal adaptive framework that incorporate security. This facilitates in design verification for security. Hence, as described in the examples below, the present invention demonstrates a formal modeling approach for a trustworthy multi-modal software design for life-critical systems that employs mode switching policies based on events triggered by changes in risk values at several abstraction layers of the multi-modal software. Each mode is composed of tasks to be performed that are decomposed into a set of operations and an essential mode incorporates tasks that are responsible for the critical functioning of the system. A system is provided that comprises a composite risk model that is associated at every abstraction layer viz. mode, task and operation levels that ensures trustworthiness. A trustworthy system state is thus represented by the multi-modal functional model incorporated with the composite risk model that performs real-time risk assessment.

Related Work

Considerable work has been done in analysis and formal modeling of adaptive systems that incorporate multiple modes and adaptive software. Phan et. al. (*IEEE International Conference on Embedded and Real-Time Computing Systems and Applications*, pp. 67-73, 2011; and *IEEE Euromicro Conference on Real-Time Systems (ECRTS)*, 2010) models systems as multiple mode components and interfaces to facilitate efficient resource usage, incremental integration and adaptivity. Each mode of a multi-modal application consists of different tasks, arrival rates or scheduling policy. Formal modeling of adaptive systems that employ policies for governance and adaptation has been shown in (Khakpour et al., *Science of Computer Programming*, Vol. 78 (1), pp. 3-26, 2012).

A complementary area of work has been in the development of adaptive software/middleware for various requirements in an adaptive system. For instance, Koo et. al. (*International Workshop on Embedded Software*, pp. 344-360, 2001) designed a hierarchical architecture for a group of multiple mode autonomous vehicles by developing a middleware that is timing-triggered in "lower levels" to meet hard task deadlines and asynchronous at "higher levels". Formal techniques for compositional adaptive software have been established in (Cheng et al., *Software engineering for self-adaptive systems*, pp. 1-26, 2009) (McKinley et al., *Computer*, Vol. 37 (7), pp. 56-64, 2004). Additionally an intrusion tolerant middleware for automatic security was discussed in (Verissimo et al., *IEEE Security Privacy*, Vol. 4 (4), pp. 54-62, 2006). The present focus, on the other hand, is to design and formally model multi-modal software for life-critical devices to ensure security by tightly integrating a risk model that triggers mode switches based on risk changes.

Nomenclature and Definitions

App={App1, . . . , Appi, . . . , Appn} is the set of software applications running on life-critical system $\mathbb{S}$.

T={$T_1$, . . . , $T_i$, . . . , $T_n$} is the set of all tasks that can run on life-critical system $\mathbb{S}$.

Each $T_i$={$T_{i,1}$, . . . , $T_{i,i}$, . . . , $T_{i,n}$} can be characterized as a set of different task implementation alternatives.

$O_{Ti}$={$o_i$, . . . , $o_p$} is the set of operations to be performed by a task $T_i \in T$.

$\mathbb{C}$ ={$C_1$, . . . , $C_i$, . . . , $C_n$} is the set of components in the system $\mathbb{S}$.

A={$a_1$, . . . , $a_i$, . . . , $a_n$} is the set of all access types.

D={$d_1$, . . . , $d_i$, . . . , $d_n$} is the set of all data sets related to the components $\mathbb{C}$ to be managed.

O={$o_1$, . . . , $o_i$, . . . , $o_n$} represent the set of all operations that can be performed by the system.

Operation: An operation is characterized by a tuple $o_i$= $\langle C_i, a_i, d_i \rangle$, where $C_i$ is a set of components s.t.$C_i \in \mathbb{C}$ , $a_i$ is the access type, and $d_i$ is the data set to be accessed/modified s.t. $o_i \in O$.

Task Alternative: Each task Ti implementation can be characterized by set of different implementation alternatives $T_i$={$T_{i,0}$, . . . , $T_{i,i}$, . . . , $T_{i,n}$}, where $T_{i,i}$ represents a specific implementation option. A task $T_k$ that does not have implementation alternatives is represented as {$T_k$} itself.

Proposition 1: A task implementation alternative $T_{i,j}$ can be defined as a function $f_T: I_{Ti} \to O_{Ti}$ that results in the same output $O_T$; for every single task alternative given the set of inputs $I_{Ti}$ to the task. That is, $\forall \{T_{i,1}, \ldots, T_{i,j}, \ldots, T_{i,n}\} \in T_i, \exists OT_{i,j} = \{o_i, \ldots, o_k, \ldots, o_n\} \subset O$ s.t. $I_{Ti}$ will result in the same output of the task $O_{Ti}$, where $O_{i,j}$ is the set of operations to be performed by $T_{i,j}$.

Operational Risk: The operational risk $rd_o$ is the risk of an operation $o \in O$. Since, $o = \langle C, a, d \rangle$, $r_o \stackrel{\text{def}}{=} r_C \oplus r_a \oplus r_d$, where the effective operational risk $r_o$ is defined as the composition ($\oplus$) of the risks of the component C utilized by the operation, component access type a and data set d associated with the component. This risk is assigned by a risk assignment function fr: $o \to r_o$ assigns the operational risk $r_o$ given the input operation $o = \langle C, a, d \rangle$.

Task Risk: The task risk $R_{Ti}$ for $T_i \in T$ is an aggregation of the set of risks associated with its composing operations, $O_{Ti}$ such that $R_{Ti} = r_{o1} + \ldots + r_{oi} + \ldots + r_{on}$.

Trustworthy Multi-Modal Design

To ensure trustworthy software design, a multi-modal framework integrated with a composite risk model is proposed for designing software for life-critical systems. This framework is based on a fixed off-the-shelf hardware that supports dual-processors, with one processor being a dedicated secure enclave like the SoCs running ARM TrustZone technology (ARM 2009). A formal modeling approach is utilized to design, model and analyze this framework.

Figure 3:
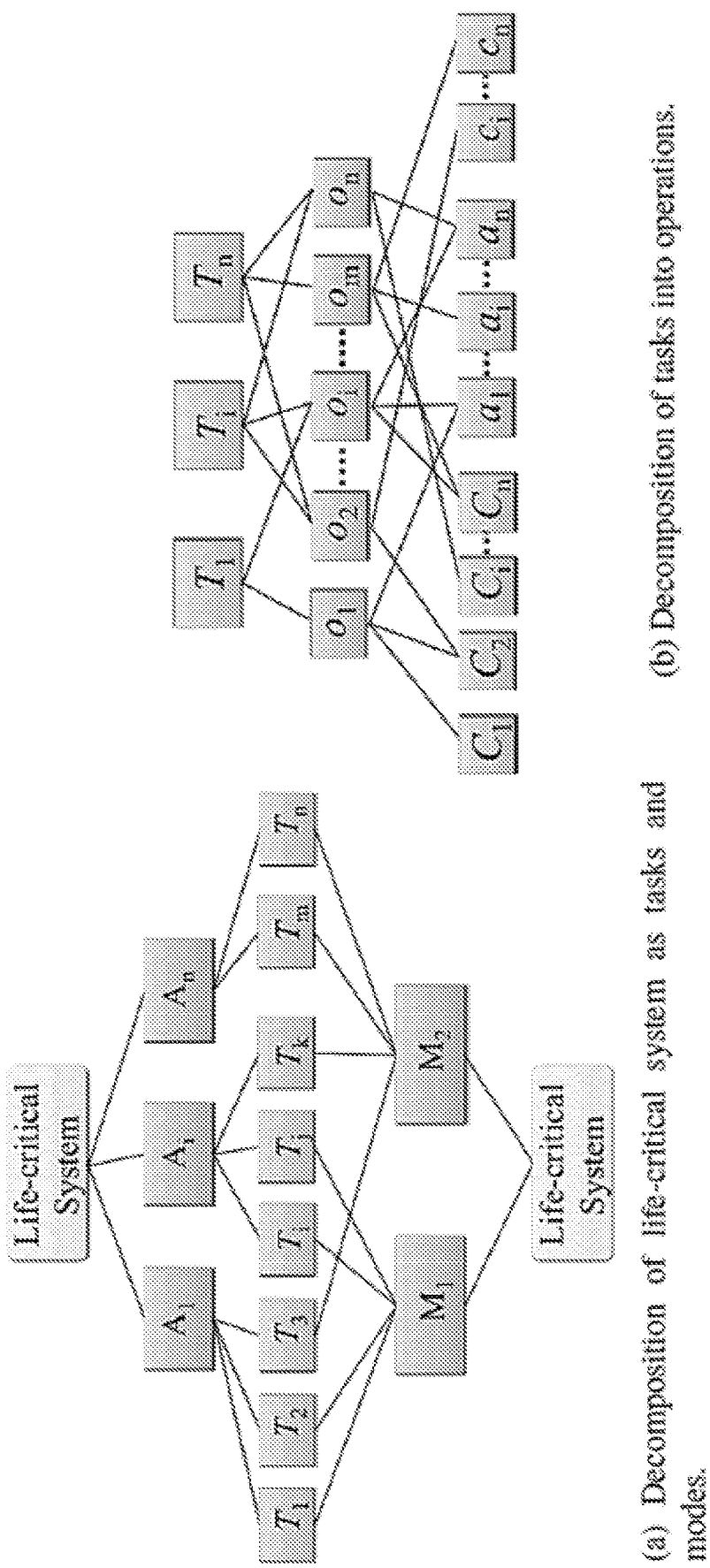
FIG. 3 shows a diagram of an exemplary decomposition of a life-critical system of a device. Panel illustrates the decomposition of the system as tasks and modes, while panel illustrates the decomposition of tasks into operations.

Multi-modal design. The system operating state $\mathbb{S}$, is composed of multiple applications "App" running on it. Each application $App_i$ is considered to be a set of tasks, $App_i \Rightarrow = \{T_1, \ldots, T_i, \ldots, T_k\} \subset T$. In this framework, a mode M is defined to be a set of tasks (can be composed of task alternatives) to be performed by the system and is characterized by a set, $M \stackrel{\text{def}}{=} T_M \Rightarrow \{T_i, \ldots, T_{i,j}, \ldots, T_{ij}\}$. The system operates in a set of modes $\mathbb{M} = \{M_1, \ldots, M_i, \ldots, M_n\}$ determined by the designer based on the granularity of functionality and security required as shown in FIG. 3, panel a. Each task $T_i$ is composed of a set of operations $OT_i$ that should be performed by it, where each operation is mapped onto a set of components required to perform that operation. A hierarchical decomposition of a life-critical system based on the multi-modal design is shown in FIG. 3.

Proposition 2: Without loss of generality (w.o.l.o.g) the set of tasks of a mode and application may be independent, $T \mathbb{M} \perp T App$. Consider a life-critical system $\mathbb{S}$ as represented in FIG. 3, panel a, where $T = \{T_1, T_2, T_3, T_i, T_j, T_k, T_m, T_n\}$ are the set of all tasks running. $\mathbb{S}$ can be decomposed into a set of applications App running on the system $\mathbb{S} \stackrel{\text{def}}{=} \{App_1, App_i, App_n\}$ or a set of modes $\mathbb{M}$ that the system operates in $\mathbb{S} \stackrel{\text{def}}{=} \{M_1, M_2\}$. Even though $\mathbb{S}$ runs the same set of tasks T, $T \mathbb{M} \perp T_{App}$ s.t. $T_M \cup T_{App} = T$.

Proposition 3: Since the framework is based on fixed hardware technology the intersection of the set of operations representing two different tasks $O_{Ti}$ and $O_{Tj}$ is not always an empty set, $O_{Ti} \cap O_{Tj} \neq \emptyset$. Fixed hardware implies a fixed set of components/resources C available, that needs to be shared among all the operations O:

An operation $o = \langle C_j^\alpha, a, d \rangle$ is s.t. $a \in \mathcal{A}$, $d \in \mathcal{D}$ and $\{C_j^1 \in \mathbb{C}$ s.t. $1 \to \mathbb{C}$ where $C_j \subset \mathbb{C}$. $j = 1, \ldots, |\mathbb{C}|$ and $i = 1, \ldots, |C_j|\}$. Since, $(|C_j| << |\mathcal{O}|$ and $j << |\mathcal{O}|) \Rightarrow |\mathbb{C}| << |\mathcal{O}|$, thus imposing the proposition.

Composite Risk Modeling. A risk model is developed to augment the risk assessment functionality and security into the multi-modal design to ensure trustworthiness. Initial risk modeling involves assigning base risk values for all the operations $R_b{}^o = \{r_{o_i}, \ldots, r_{o_j}, \ldots, r_{o_n}\}$.

A risk r is assigned based on the composite risk assignment function $f_r(I_1) \to r$. An aggregation function is defined as $f_{o \to T}: R_{OT} \to R_T$, where $R_{OT} = \{r_{o1}, \ldots, r_{oi}\}$ and $R_T$ is the risk of the task/task alternative $T \in T$. An additional mode risk aggregation function is defined $f_{T \to M}: R_{TM} \to R_M$, that assigns a composite risk $R_M$ to a mode M, given the set of risks of M's containing tasks $T_M$. $R_M$ is the parameter ensuing risk assessment and management decisions during the deployment of the device. An external runtime security threat detector provides a stream of detected security threat probabilities at the operation level, upon which the assigned risks at each abstraction are updated.

A set of risk thresholds are defined that triggers state changes for risk management and mitigation decisions. The external threat detection system detects security threats at the operation level providing a set of threat probabilities upon which the operational risks are updated.

Operational Risk Threshold: $R_{th}{}^O$ represents the risk beyond which an operational level mitigation action $MA_{op}$ is performed in order to reduce the effective composite risk mode risk $R_M$.

Task Risk Threshold: $R_{th}{}^T$ represents the risk affecting a task $T_i$ beyond which a task alternative $T_{i,i}$ is chosen in order to mitigate the risk and this mitigative action is representative as $MA_{task}$ Mode Switch and Device Risk Threshold: $R_{th}{}^M$ represents the risk beyond which the threat to the current operating mode $M_i$ is too high and requires a shift to a lower mode of functionality, $\{M_i \to M_{i,j} \exists R_{th}{}^D$ s.t. $j < i$ and s.t. $j = 0\}$, and represent this action as $MA_{mswitch}$. $M_0$ is defined to be the essential operating mode that is responsible for the essential performance of a life-critical system and $R_{th}{}^D$ to be the risk beyond which the life-critical system operation has to be shifted to $M_0$ and this mitigative action is represented by $MA_{M0}$.

A key component to incorporate security or trustworthiness in this framework is the augmentation of the essential mode, $M_0$. The essential mode is the lowest operating mode of the system that ensures essential functionality of the life-critical system. The mode $M_0$ consists of set of tasks $T_{critical} = T_{M0} = \{T_{c1}, \ldots, T_{ci}, \ldots, T_{cn}\}$ s.t. $T_{M0} \in T$. $T_{M0}$ represents a set of tasks responsible for the critical/essential functioning of the system that cannot be affected by a mitigative action.

Figure 4:
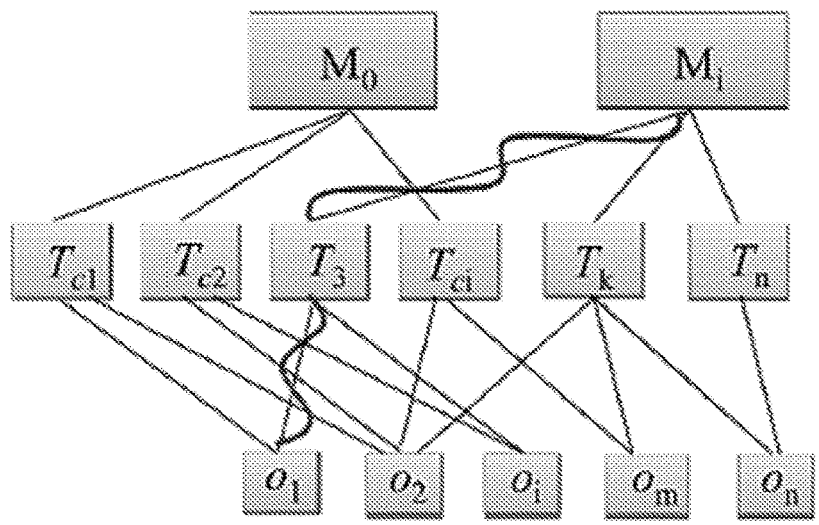
FIG. 4 shows an illustration of a mitigative action path in an embodiment of the present invention.

Proposition 4: A mitigative action to cut-off or disable operations does not affect the tasks in the essential mode, TM0. A mitigative action path is defined as the directed path leading to the cutting off or disabling of corresponding tasks or modes based the operations being affected by a security threat or vulnerability. A mitigative action path can be represented as a set of directed edges where the node represents an operation, task or mode and an edge is the composition among them. Consider two mitigative action paths $map_i$ and $map_{crit}$ s.t. $map_i = \{(M_i, T_i), (T_i, o_{ci})\}$ and $map_{crit} = \{(M_0, T_{ci}), (T_{ci}, o_{ci})\}$ where $T_i \in T_{Mi}$, $T_{ci} \in T_{M0}$ and $o_{ci} \in O$. From Proposition 3, oci can be a part of $map_{crit}$ and $map_i$. However, a mitigative action $MA_i$ affecting operation $o_{ci}$, will lead to a mitigative action along $MA_i \to map_i$ and not affecting $map_{crit}$, i.e. $map_i \perp map_{crit}$ and thus, $MA_i$ does not effect the task $T_{ci} \in T_{M0}$. An illustration is shown in FIG. 4, where the swiggly line represents a mitigative action path. The operation $o_1$ is a part of tasks $T_{ci}$ and $T_3$ of modes $M_0$ and $M_i$ respectively. Under the current operating mode of $M_i$, if an operation $o_1$ is affected by a security threat or vulnerability, then the mitigative action is taken along swiggly line which does not affect the path $\{(M_0, T_{c1}), (T_{c1}, o_1)\}$ that is responsible for the essential functioning of the device.

Trustworthy Multi-Modal Framework

The trustworthy multi-modal framework involves the incorporation of the composite risk model into the multi-modal design at every hierarchical level as discussed above. The system operates in modes organized in a monotonically increasing sequence of risks and functionalities. This can be decomposed as, $\mathbb{S}=\{(M_n, R_{Mn}), \ldots, (M_i, R_{Mi}), \ldots, (M_0, R_{M0})\}$ s.t. $M_{n\,func} \geq M_{n-1\,func} \geq \ldots M_{i\,func} \geq \ldots M_{0\,func}$ and $R_{Mn} \geq R_{Mn-1} \geq \ldots R_{Mi} \geq \ldots R_{M0}$.

Figure 5:
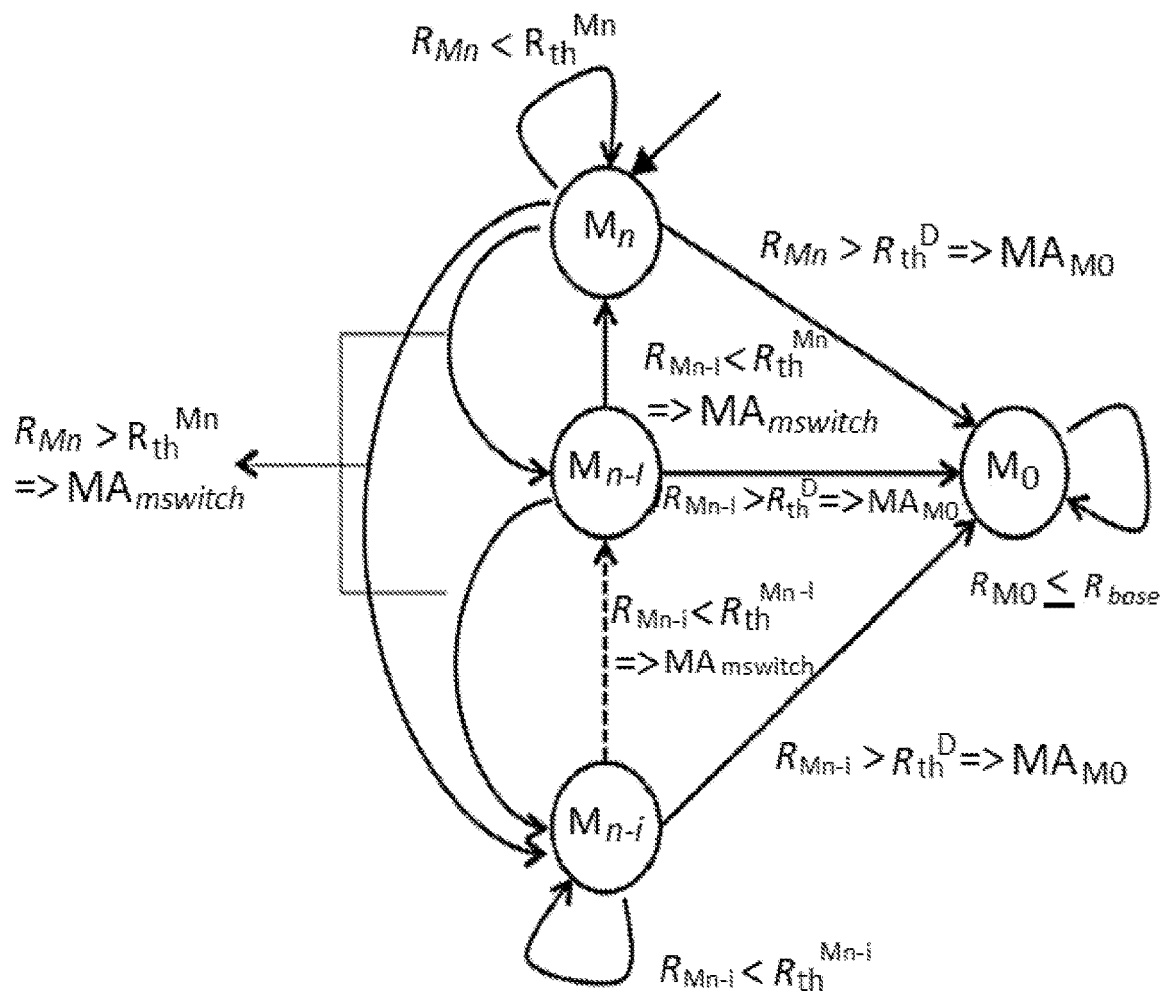
FIG. 5 shows an illustration of a finite state machine of a trustworthy multi-modal framework in an embodiment of the present invention.

Formally, this framework is modeled as a finite state machine (FIG. 5), whose states represent the operating modes of $\mathbb{S}$ and state transitions are represented by risk based event triggered mode changes. It is represented as TMM=($\mathbb{M}, \mathbb{R}_\mathbb{M}, M_n, \delta_r$) where:

$\mathbb{M}$ is the set of states which is the initial set of modes specified by the designer for the system $\mathbb{S}$.

$\mathbb{R}_\mathbb{M}$ is the input set of risk values associated with all the modes $\mathbb{M}$.

$M_n$ is the initial state which is the highest operating mode of the system representing full functionality of the system.

$\delta_r$: $\mathbb{M} \times \mathbb{R}_\mathbb{M} \to \mathbb{M}$ state or mode transition function based on the current operating mode and it's associated risk ($M_i$, $R_{Mi}$) resulting in an output mode $M_j \in \mathbb{M}$. The resulting mode $M_j$ is based on the application of the specific mitigative action as defined above.

Each mode can be described as a composition of the set of tasks to be executed by the mode and the risk associated with the mode M=($T_M$, $R_M$), s.t. M∈M ⊂ $\mathbb{M}$T and $R_M = f_{T \to M}(R_{TM})$. A mode is modeled by another finite state machine MFSM=($T_M, R_{TM}, \tau_{rt}, A$), where:

$T_M$ is the set of all the tasks/task alternatives that is composed of the mode M.

$R_{TM}$ is, the set of risks associated with all the comprising tasks/task alternatives ∀T∈TM, where T is either a task or a task implementation alternative.

$\tau_{rt}$: RTM×TM→TM is the task transition function based on the input set of tasks and their corresponding risks associated with the tasks ($T_M$, $R_{TM}$) that results in a new set of tasks or task alternatives based on the mitigative action specified above.

Task-Operation Interface Composition

An interface abstraction is utilized to formally define the interface between the set of tasks of the system T and the set of operations O under the trustworthy multi-modal framework. The trustworthy interface is abstracted as TINF=(T, $O_T, R_{OT}, R_T, f_{0 \to T}, fr, O'_T, R'_T, A, EXT$), where:

T represents the input task to TINF.

$O_T$ is the set of operations composed of the task T.

$R_{OT}$ is the composite risk associated with all the comprising operations $O_T$ where an operation $o \in O_T$ is assigned a risk based on the risk assignment function $f_r$.

$f_r$ is based on a probabilistic security threat estimator EXT (Rao et al. 2017).

$R_T$ is the risk associated with the input task T assigned by the function $f_{0 \to T}$.

$O'_T$ is the updated set of operations of task T if a mitigative action is taken at the operational level.

$RO'_T$ is the updated risk of the updated set of operations that propagates to an updated task risk $R'_T$.

Conclusion

This example provides a formally modeled a trustworthy software design for life-critical systems that will aid in verification and synthesis of actual designs. The software follows a multi-modal design, where each mode represents a set of tasks to be performed and the modes are arranged in an increasing order of functionality and risk. By modeling a composite risk model along with the multi-modal design trustworthiness is ensured by real-time risk assessment. Finite state machines are utilized to model the trustworthy multi-modal framework.

Example 4—Hardware-Based Probabilistic Threat Detection and Estimation for Embedded Systems With billions of networked connected embedded systems, the security historically provided by the isolation of embedded systems is no longer sufficient. Both proactive security measures that prevent intrusions and reactive measures that detect intrusions are essential. Anomaly-based detection is a common reactive approach employed to detect malware that has evaded proactive defenses by observing anomalous deviations in the system execution. Timing-based anomaly detection detects malware by monitoring the system's internal timing, which offers unique protection against mimicry malware compared to sequence-based anomaly detection.

However, previous timing-based anomaly detection methods focus on each operation independently at the granularity of tasks, function calls, system calls, or basic blocks. These approaches neither consider the entire software execution path nor provide a quantitative estimate of the presence of malware. This example presents a novel model for specifying the normal timing for execution paths in software applications using cumulative distribution functions of timing data in sliding execution windows. A probabilistic formulation is presented for estimating the presence of malware for individual operations and sequences of operations within the paths, and thresholds are defined to minimize false positives based on training data. Experimental results with a smart connected pacemaker and three sophisticated mimicry malware demonstrate improved performance and accuracy compared to state-of-the-art timing-based malware detection.

Introduction

Internet connected devices have grown explosively and are estimated to reach several billions by 2020 (Evans, D., "The Internet of Things: How the Next Evolution of the Internet Is Changing Everything," Cisco White Paper, 2013). At the same time, more than 100 million new malware were created in 2016, which is indicative of the scope of the potential threat to the security and privacy of users and companies (McAfee Labs. Threats Report: December, 2016). Embedded systems used to be physically isolated (e.g., the computer inside a locked automobile), which in turn provided some measure of security because an attacker had to access to the system physically to preform an attack. However, an increasing number of previously secured embedded systems are now connected to the Internet, which opens the door to attackers. While Internet connectivity has tremendous bene-fits across wide ranging applications, including automobiles, medical devices, etc., that connectivity brings new threats to these systems. The impacts of malware can range from minor inconveniences to life-threatening situations. For example, Li et al. (*Conference on e-Health Networking Applications and Services*, pp. 150-156, 2011) demonstrated that by using publicly available information, a malicious packet could be transmitted to an insulin pump that would deliver a fatal dose of insulin.

While proactive approaches (e.g., secure communication protocols, static application security testing) are essential, runtime intrusion and malware detection are also needed to detect when attackers are able to circumvent a system's defenses. Malware detection can be broadly categorized into signature-based detection and anomaly-based detection. Signature-based detection detects malware by matching execution behaviors, code patterns, etc. to a library of known malware. This requires storing a large library for the growing number of malware and their variants, and limits the ability to detect zero-day exploits (Holm, H., "Signature Based Intrusion Detection for Zero-Day Attacks: (Not) A Closed Chapter?," *Hawaii International Conf. on System Sciences,* 2014). In contrast, anomaly-based detection detects malware by detecting deviations in execution behaviors at runtime from a pre-defined model of normal system behaviors. Anomaly-based detection commonly focuses on monitoring the internal sequence of operations within the system, where any deviation from the expected sequence would be considered anomalous (Chandola et al., *ACM Computing Survey,* 41(3), 2009; Zhang et al., *Conference on Compilers. Architectures and Synthesis for Embedded Systems,* pp. 43-54, 2005; and Arora et al., *Conference on Hardware Software Co-design and System Synthesis,* pp. 106-111, 2006). However, sequence-based anomaly detection does not protect against mimicry attacks. Wagner et al. (*Conf. on Computer and Communications Security,* pp. 255-264, 2002) and Kruegel et al., (*USENIX Security Symposium,* pp. 161-176, 2005) evaluated several sequence-based anomaly detection methods and demonstrated that malware can hide their presence by mimicking the correct execution sequence of the target application/device. This sophisticated type of malware is known as mimicry malware.

Timing-based anomaly detection improves the detection rate and resilience to mimicry malware by adding timing in-formation to the normal system model. Time is a critical component in embedded systems and strict timing constraints are often required to ensure system correctness and safety. The resulting time sensitivity means that small changes in the timing of some operations can adversely affect the system execution, in the worst case leading to system failures. By monitoring both the internal timing of operations and the execution sequence, timing-based anomaly detection can detect mimicry attacks by observing the resulting changes in system timing. Several approaches use timing of individual operations to detect malware at runtime (Zimmer et al., *ACM/IEEE International Conference on Cyber-Physical Systems (ICCPS),* pp. 109-118, 2010; Yoon et al., *Real-Time and Embedded Technology and Applications Symposium,* 2013; and Lu et al., *ACM Transactions on Embedded Computing Systems,* vol. 17(2), Article 38, pp. 1-27, 2017), but these approaches often suffer from high false positive rates, which is a well-known problem in existing anomaly detectors.

This example presents a statistical approach for modeling the normal system behavior of embedded applications using cumulative distribution functions (CDF) of timing data within sliding execution windows. Instead of independently focusing on single operations, the normal timing model enables the monitoring of each execution path within a software application. For each execution path, a probabilistic formulation is used to estimate the presence of malware for individual operations and sequences of operations. To ensure rapid detection, a hardware-based runtime detector analyzes timing samples within a fixed-size sliding window, comparing the CDFs of the sliding window against the normal system model. The detector calculates an estimated probability of malware by measuring the percent-age of the CDF that falls outside the normal boundaries for each operation and for the entire path. The malware detector is implemented in hardware that interfaces to a processor's trace port, which enable the runtime detection to be performed without impacting the software execution. Experiments with a smart connected pacemaker prototype and three mimicry malware were conducted to evaluate the detection rate, false positive rate, detection latency, area, and power consumption of the presented approach. The method was also compared to a state-of-the-art timing-based malware detection.

Related Work

Several efforts have been made to develop timing-based anomaly detection. Most of these existing approaches detect the timing of single operations and do not consider the history of execution timing at runtime. Also, some approaches incur high false positive rates. These approaches primarily focus on detection accuracy and detection rates, which are both critical aspects of malware detection, and many achieve excellent results. But none specifically consider minimizing the false positive rate or monitoring complete execution paths. In contrast, the present approach attempts to minimize the false positive rate, maintain a high detection rate, consider complete execution paths, and provide a quantitative estimate of the probability of malware.

Patel et al. (*Design Automation Conference,* pp. 858-861, 2008; and *IEEE Transactions on Very Large Scale Integration Systems,* No. 99, pp. 1-14, 2010) presented a MPSoC intrusion detection method that monitors the execution's sequence and time of basic blocks within the software application using a control flow map. The detection method inserts custom instructions in the software binary to identify basic blocks. Those instructions transmit the execution data to a dedicated processor for analysis. The overhead of the instrumented code and additional processors incur a performance overhead between 6.6% and 44% and an area overhead of 26.9%. For many embedded systems, such as implantable medical devices, the impact on the performance of the software application is often infeasible or prohibitively expensive.

Zimmer et al. (*ACM/IEEE International Conference on Cyber-Physical Systems (ICCPS),* pp. 109-118, 2010) proposed a timing-based intrusion detection system at the granularity of function calls and return paths, specifically designed to detect code injection attacks. However, this approach makes decisions based on individual operations, instead of considering entire execution paths. This can lead to a high number of false positives.

Lu et al. (*ACM Transactions on Embedded Computing Systems,* Vol. 17(2), Article 38, pp. 1-27, 2017) developed a range-based runtime anomaly detection method that monitors the best-case execution time (BCET) and worst case execution time (WCET) of individual operations within a software application. Although this approach can detect malware efficiently, it independently makes decisions based on individual operation without considering statistical characteristics of execution timing. By only considering the timing range defined the BCET and WCET of individual events, the timing variability therein presents challenges in accurately training the model to achieve low false positives.

Yoon et al. ("SecureCore: A Multicore-based Intrusion Detection Architecture for Real-Time Embedded Systems," *Real-Time and Embedded Technology and Applications Symposium,* 2013) presented SecureCore, which monitors the timing distribution of basic blocks. At runtime, SecureCore measures the execution time of a basic block and estimates the probability of that time from a statically determined timing distribution. If that probability is less than a specified threshold (e.g., 5%), SecureCore flags the execution as potentially malicious. This approach is highly dependent on the threshold utilized, since false alarms triggered at runtime may decrease the overall system performance. As such, a balanced threshold is critical for the correct functionality of the system. However, it should be noted that false positives are inherent in this approach, and when applied to operations at a coarse granularity (e.g., system/function calls) the false positive rate can be very high.

Assumptions and Threat Model

The goal of CDF-based anomaly detection is to detect sophisticated mimicry malware with minimum or no false positives given the following assumptions and threat model.

The target malware is mimicry malware (Wagner et al., *Conf. on Computer and Communications Security*, pp. 255-264, 2002; and Kruegel et al., *USENIX Security Symposium*, pp. 161-176, 2005), which attempts to evade anomaly detection by mimicking normal execution behavior. Mimicry malware interleaves malicious and normal execution and are sophisticated enough to escape detection from simple sequence-based anomaly detection. Sequence-based anomaly detection is also used in the present approach, which can detect non-mimicry malware and necessitates an attacker's need to use mimicry malware.

The attacker either has access to system software or can simulate the system execution to determine the system's execution sequence, which is needed to can create mimicry malware. The attacker is able to remotely insert the malware into the system utilizing software that exploits a vulnerability, which may be unknown or known but unpatched at the time of insertion. The anomaly-based malware detection presented in this example focuses on detecting malware that has already been inserted in the system and not on detecting the software or system vulnerabilities that lead to the intrusion.

The target embedded application consists of multiple software tasks (or threads) executing on a single processor core, although it is noted that the detection method presented herein can be applied to other application scenarios including multicore systems.

The granularity of detection in this example is at the level of system and function calls, generically called operations. The proposed approach can be applied at coarser or finer granularities following the same design principles.

The detection method considers individual execution paths, where a path is defined as a specific sequence of operations within the control flow of each software task.

To evaluate the CDF-based anomaly detection method, three mimicry malware based on known malware (albeit from different applications) were considered (Sametinger et al., *Communication of ACM*, Vol. 58(4), pp. 74-82, 2015; and Wasicek et al., *Design Automation Conference*, pp. 1-6, 2014). The File Manipulation malware breaks confidentiality and integrity by intruding into the file system and performing reads/writes on a target file. The malicious goal varies between malware and target application (e.g., in the pacemaker application, modifying the records in cardiac log file to deceive the physician). The second is a Fuzz malware (Wasicek et al., *Design Automation Conference*, pp. 1-6, 2014) that is commonly used to interfere with the system's pre-defined functionality by fuzzing (or slightly changing) data. Fuzz malware can be implemented in various levels, which enables the evaluation of the effectiveness of malware detection for different fuzzification levels. The Information Leakage malware reads the patient's cardiac activity log and transmits the data to a third-party server. These three malware were implemented by interleaving malicious operations with mimicked normal operations that overall follow the normal execution sequences and execution paths. The present primary threat is malware affecting legitimate executables, specifically mimicry malware, which assume an attacker knows which operations are monitored. As the approach detects deviations in execution sequences and timing, it can also indirectly detect other malware types.

CDF-Based Anomaly Detection

Figure 6:
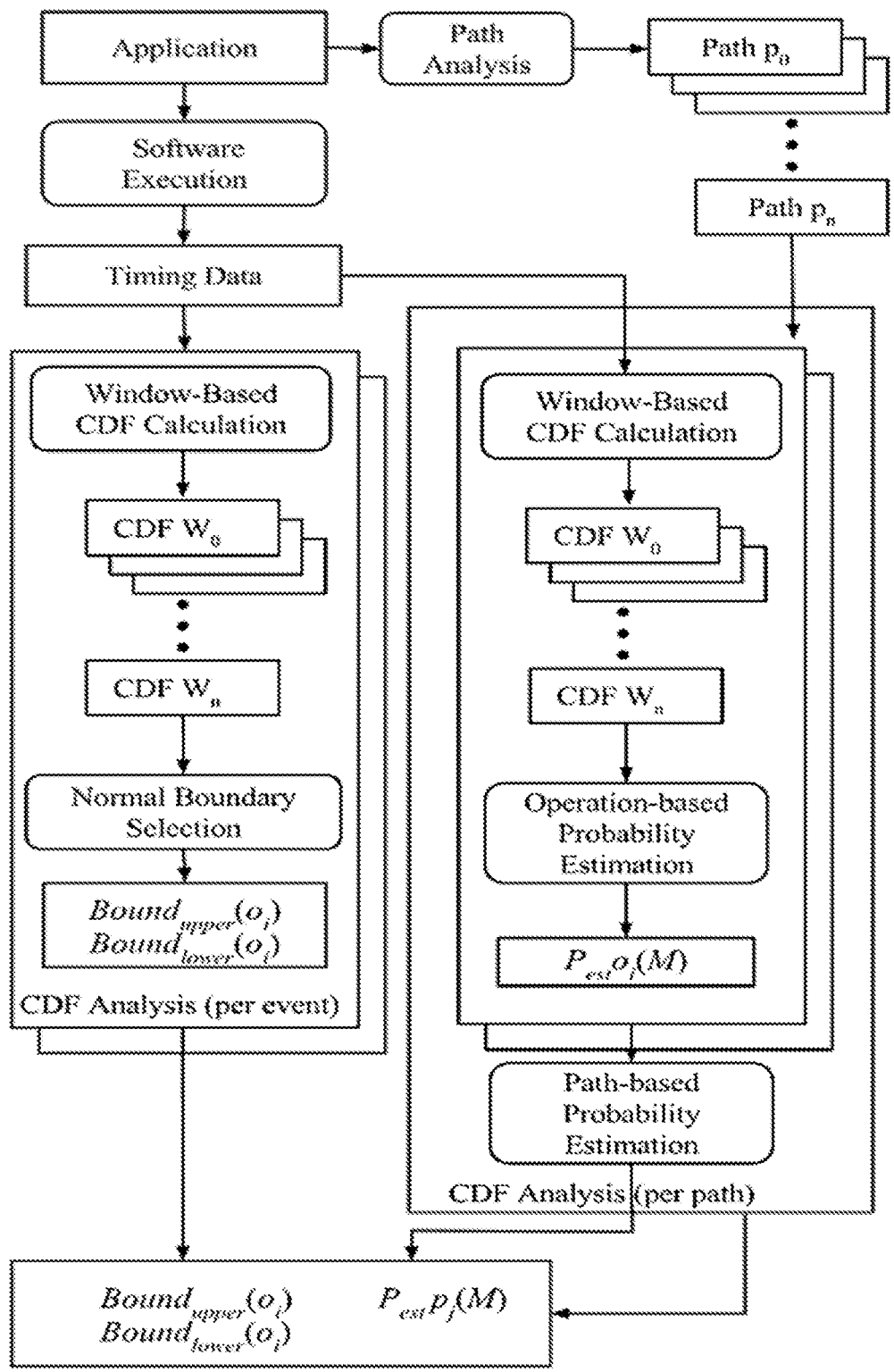
FIG. 6 shows a design flow of a CDF-based anomaly detection in an embodiment of the present invention. The CDF Analysis (per path) module is utilized both at runtime and in static analysis, with the only distinction being the input data will be extracted at runtime, which may or may not be malicious.

FIG. 6 presents the design flow of the CDF-based anomaly detection method. The software application is first statically analyzed to determine the operations, $o_i$, and execution paths, $p_i$, within all software tasks. For each operation, the system is executed to collect training data by executing the system under various normal execution scenarios, each for a sufficient duration. The processors trace interface (Stollon, N., "On-Chip Instrumentation: Design and Debug for Systems on Chip," Springer US, 2011) is utilized to observe the timing of operations without affecting the execution or timing thereof. For a specific window size and stride, the CDF analysis determines the CDFs per window within the training data. These CDFs are used to calculate the upper bound, $Bound_{upper}(o_i)$, and lower bound, $Bound_{lower}(o_i)$, of the CDF per operation, which can be used to detect deviations at runtime.

This approach is based on the Kolmogorov-Smirnov test (K-S test) (Chakravarti et al., Handbook of Methods of Applied Statistics, Volume I, John Wiley and Sons, pp. 392-394, 1967) and seeks to detect anomalies by statistically comparing the distribution of timing data between a normal system execution model and the runtime execution. Without assuming a specific distribution, the K-S test can be used to test a sample with a reference distribution for equality, where the reference distribution is the normal system model and the sample is the runtime execution. To test if the sample and normal distribution are equal, the K-S test computes the CDF for both, and measures the maximum difference between the two. While the K-S test can be directly applied to detect anomalous executions, one would need to collect 1000s of timing samples for each operation before testing the distribution for equality, thus leading to unacceptably long detection latencies. Based on the K-S test, the approach measures the execution timing with a small execution window. To construct the normal system model, the CDF for each execution window in the training data is determined. However, instead of storing all CDFs, which would require prohibitively larger memory requirements, only the minimum and maximum boundaries of the CDFs across all windows are stored. At runtime, instead of calculating the maximum difference between two distribution, the percentage of samples that do not fall within these CDF bounds were calculated.

After determining the CDF boundaries, additional normal training data is used to calculate the maximum deviation the CDFs can have from the normal execution while still being considered normal, defined as the threshold. For each operation, the percentage of CDF values for each execution window outside the operation's CDF boundaries is used to determine an estimate of the probability of malware. False positives can be quantified by analyzing the estimated probability of malware for normal execution timing. The probabilities of malware for all operations within an execution path are analyzed to determine a per-path threshold, which defines a per-path probability beyond which the approach is confident about the presence of malware.

At runtime, the detector utilizes the CDF boundaries to estimate the probability of malware for each execution path. Timing samples are collected using the same window size and stride. The CDFs for each operation are calculated, and the percentage of CDF values outside the statically determined CDF bounds are used to estimate the probability of malware for each operation. For each execution path, the detection method calculates the probability of malware affecting the timing of the path's operations. This estimated probability is compared against the predefined threshold to determine if malware is present in the system.

Window-Based CDF Boundary Construction

The CDF represents the distribution of timing samples within an execution window. Creating a model of the normal system behavior using CDFs allows one to estimate the percentage of overlap between runtime CDFs and the normal system model's CDFs. Additionally, it reduces the storage requirements compared to other approaches (e.g., KDE estimation).

Figure 7:
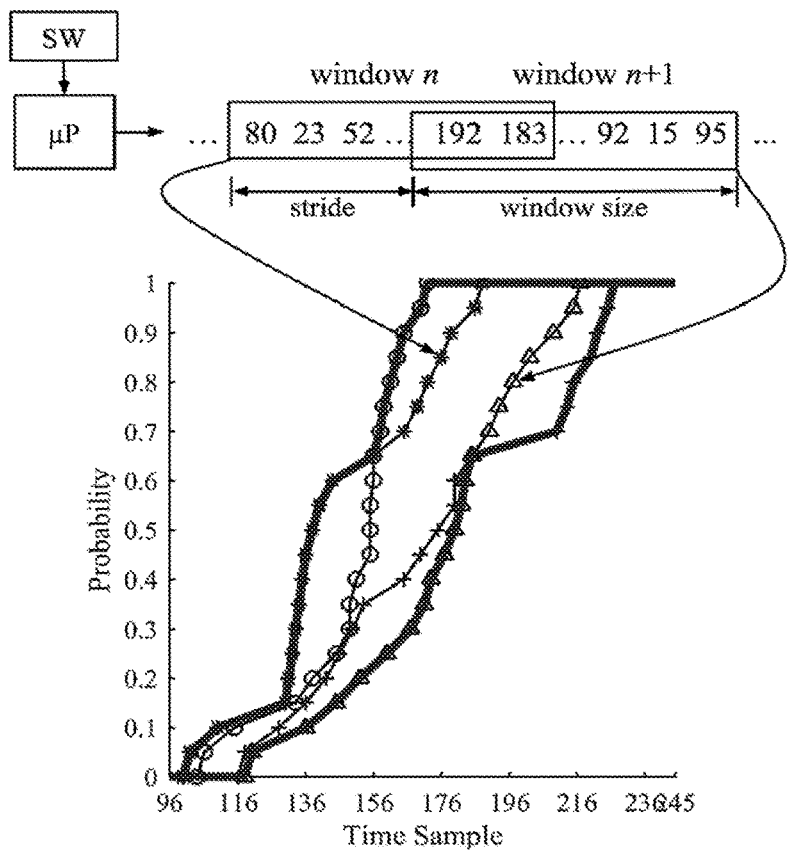
FIG. 7 shows a conceptual overview of a window-based CDF calculation in an embodiment of the present invention, highlighting the sliding windows of timing samples used to calculate the CDF of an operation. The plot shows the CDFs for four different windows, from which the upper and lower CDF boundaries can be calculated.

Storing and analyzing the entire execution history for an operation is infeasible and would lead to prohibitively long detection delays. Therefore, the CDF-based anomaly detection collects and analyzes an operation's timing within a fixed execution window that maintains multiple execution timing samples. The window size, defined as the number of timing samples maintained, should be large enough for statistical analysis but small enough to reduce the detection delay. For each window, the stride defines how many new timing samples are collected before re-calculating the CDF. A smaller stride produces smaller changes in the CDF, but requires re-calculating the CDFs more frequently to detect malware. However, a larger stride would allow malware to execute long-er before being detected, which could be fatal for some systems. FIG. 7 presents a conceptual overview of the window-based CDF calculations showing the resulting CDFs for four different execution windows and the resulting boundaries. In this example, the window size is 20 and the stride is 5. Thus, each CDF involves 20 samples, in which 25% are new timing samples and 75% are prior samples.

After the CDFs for all windows of an operation are obtained during the training stage, the boundaries that define the normal system's model can be determined. The bolded lines in FIG. 7 illustrates the CDF bounds for the sample windows. The lower boundary is constructed by points in the CDFs that have the lowest cumulative probability at each timing value, and the upper boundary is constructed by the points in the CDFs that have the highest cumulative probability at each timing value. These boundaries are configured into the anomaly detector and used at runtime. Instead of fitting the boundary curve to be a high dimensional representation, because a fixed window size is used, the CDF's cumulative probability will be discretized with a step size equal to the inverse of the window size. Thus, the CDF boundaries are stored as two scalar arrays, $Bound_{upper}(o_i)[\ ]$ and $Bound_{lower}(oi)[\ ]$, that contain the timing values corresponding to each discrete cumulative probability step.

Estimating Probability of Malware and Threshold-Based Malware Classification

Figure 8:
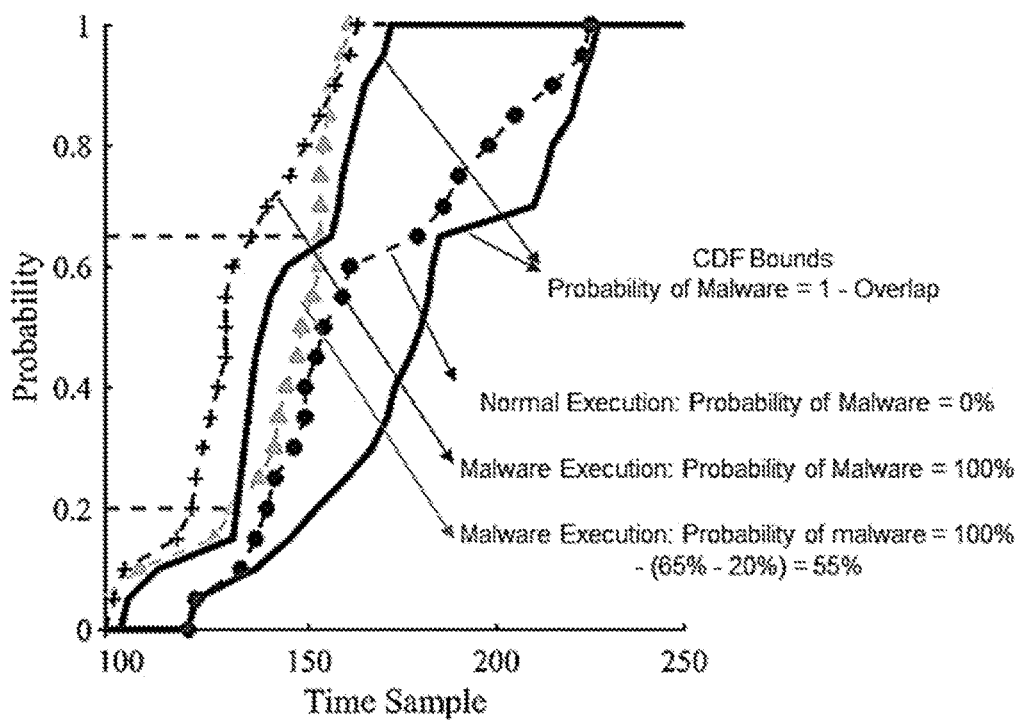
FIG. 8 shows three runtime CDFs plotted with upper and lower CDF bounds (solid lines), showing the overlap used to calculate the estimated probability of malware. Normal execution of the system (circles) is always inside the previously obtained boundaries. The CDFs for malware (crosses and triangles) results in a CDF that does not fall within the CDF boundaries.

For an operation $o_i$, the estimated probability of malware, $P_{est}o_i(M)$, depends on the percentage of CDF values outside the CDF boundaries defined in the normal system model. FIG. 8 presents an example demonstrating how the probability of malware is calculated. The red solid lines are the normal boundaries, and the dashed lines are the CDFs obtained from three different windows of runtime timing data. The black (crosses) CDF is completely outside the CDF boundary, and thus is estimated to have 100% malicious execution. In contrast, the blue (circles) CDF is completely within the CDF boundaries and thus is estimated to have 0% malicious execution. For a CDF that partially overlaps with the CDF boundary, the probability of malware is estimated as the percentage of points within the CDF that fall outside the boundaries. For example, the green (triangles) CDF has a probability of malware $P_{est}o_i(M)=1-(0.65-0.20)=0.55$, which indicates there is estimated to be a 55% probability the execution is malicious. In practice, with the $Bound_{upper}(o_i)[\ ]$ and $Bound_{lower}(o_i)[\ ]$ arrays, the $P_{est}o_i(M)$ is calculated by determining the number of samples that fall outside these bounds. For example, if 19 of 20 timing values in a window are outside the CDF boundary, the estimated probability of malware $P_{est}o_i(M)=0.95$.

Individual operations are considered malicious if the estimated probability of malware, $P_{est}o_i(M)$ is greater than a predefined threshold. Instead of making a decision based on a single operation, which may yield high false positive rates, a more robust decision is made by considering the $P_{est}o_i(M)$ for multiple operations in an execution path. An execution path is a sequence of operations within a software task. The probability of malware execution in a path would be higher if the probability of more operations within the path are estimated to be malicious. The probability of malware for a path $p_i$ is:

$$P_{est}p_j(M)=1-\Pi_{i=0}^{n}(1-P_{est}o_i(M)) \qquad (1)$$

Figure 9:
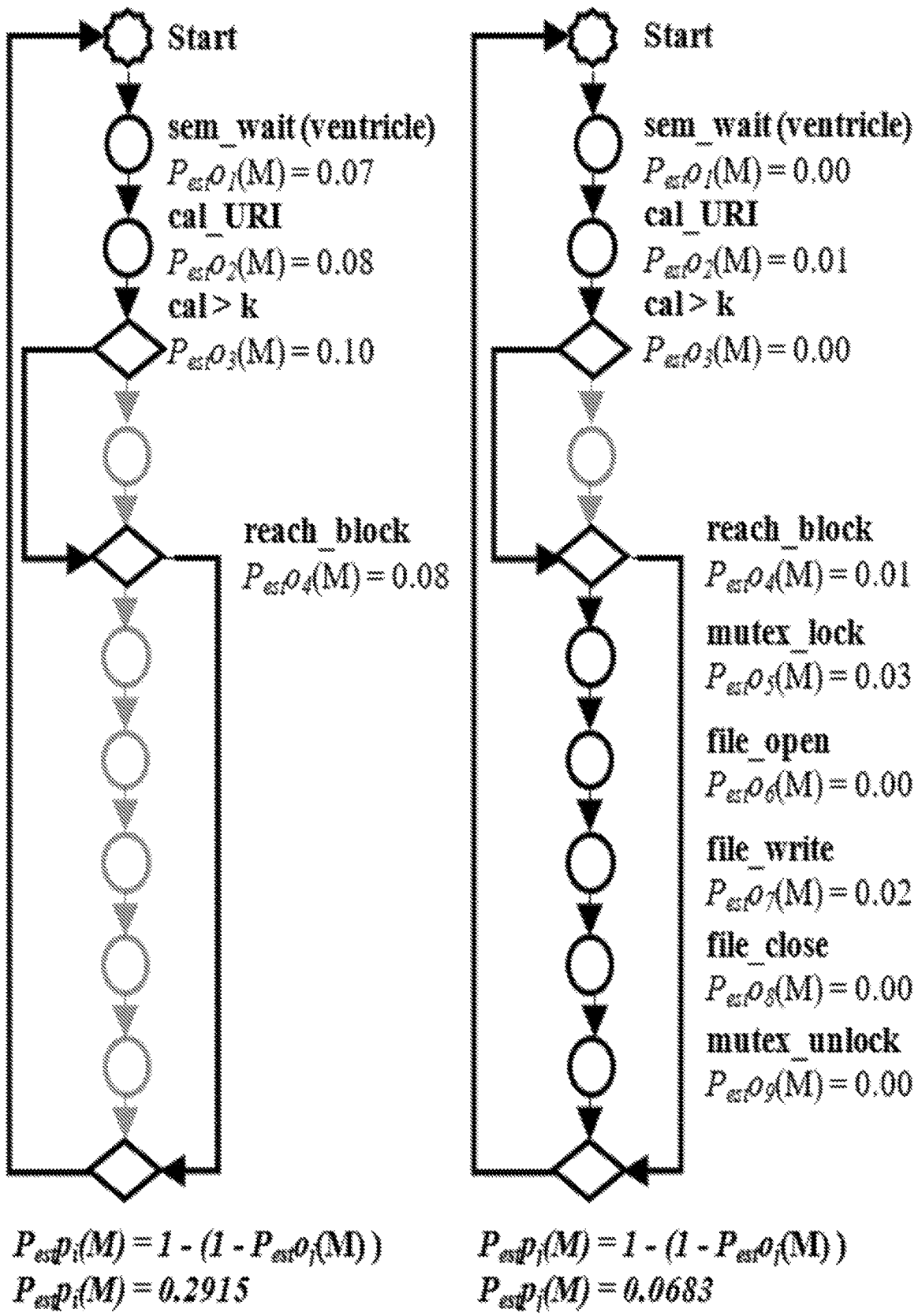
FIG. 9 shows annotated execution paths within a software task of a network-connected pacemaker in an embodiment of the present invention. The left path has four monitored operations, and the right path has nine. Annotations next to each operation indicate the estimated probabilities of malware for that operation. The resulting estimated probabilities of malware for each execution path and shown below each path.

FIG. 9 presents two different example execution paths for the smart connected pacemaker application considered in this example. For the execution scenario shown on the left, four operations are monitored and the estimated probability of malware for path is calculated as: $P_{est}p_i(M)=1-(1-0.07)(1-0.08)(1-0.10)(1-0.08)=0.2915$. This indicates there is a 29.15% chance that the execution of the task along this execution path for the current execution window is malicious. The execution path on the right represents a different execution path in the same task, in which nine operations are monitored. The estimated probability of malware for this alternative path is: $P_{est}p_j(M)=1-(1-0.00)(1-0.01)(1-0.00)(1-0.01)(1-0.03)(1-0.00)(1-0.02)(1-0.00)(1-0.00)=0.0683$, which indicates there is a only 6.83% chance this path's execution is malicious.

Whether malware is affecting the system execution is decided per execution path, comparing the path's estimated probability of malware to a path specific threshold. The threshold is defined by the maximum probability of malware execution $P_{max}o_i(M)$ per operation. The $P_{max}o_i(M)$ is calculated by processing a second set of normal training data utilizing the same approach as above. The threshold for path $p_j$ is:

$$Tp_j=1-\Pi_{i=0}^{n}(1-P_{max}o_i(M)) \qquad (2)$$

Due to limitations of design-time training, some normal system executions may deviate from the CDF boundaries. Without accounting for these deviations, a high false positive rate would be expected. The path-based threshold is utilized to minimize that false positive rate. Equation (2) utilizes the minimum overlap found in the second training data set (normal data only), while equation (1) is utilized at runtime to obtain the estimated probability of malware for the entire path. For example, assume the minimum overlap throughout all windows of operation $o_i$ for the second set of normal timing data is 0.90. This means that the highest estimated probability of malware for normal system execution is 0.10, which in turns means that a runtime estimated probability of malware greater than 0.10 will be reported as malware. If five operations within that path are monitored, and each has the same minimum probability, the path threshold $Tp_j=1-(1-0.10)^5=0.40951$. This approach strives to ensure the CDF-based anomaly detection is accurate with minimal false positives. It can also be observed that as the number of monitored operations increases, the threshold decreases, but the strictness of the approach remains.

Runtime Detection

At runtime, the threshold of each path and normal CDF boundaries are configured within the hardware-based malware detector. The malware detector collects timing samples of each operation by analyzing the signals from the processor trace port. Whenever the stride is reached for an operation's window, the detector calculates the CDF and $P_{est}o_i(M)$ for the operation. When the CDFs of all monitored operations within a path j are calculated, the anomaly detector calculates $P_{est}p_j(M)$ and compares that estimated probability with the threshold $Tp_j$. If $P_{est} p_j(M) > Tp_j$, the detector asserts a non-maskable interrupt indicating the presence of malware.

Figure 10:
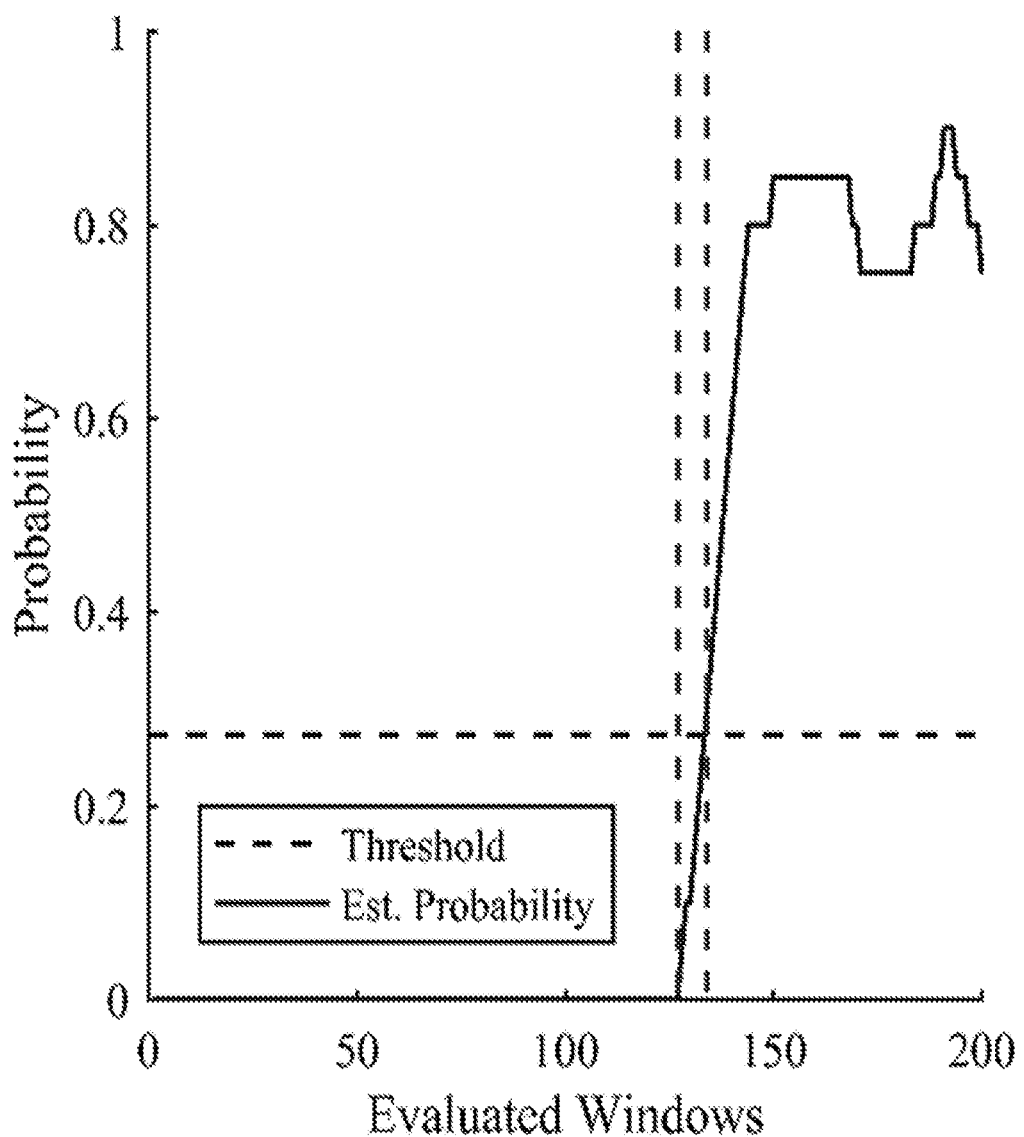
FIG. 10 shows a timeline of estimated probability of malware for both normal and malware (File Manipulation) execution highlighting the detection latency.

Detection latency is a critical indicator of the detection performance and is defined as the time between the moment when malware begins to execute and the moment the detector detects the anomalous execution and asserts the alert. For the CDF-based anomaly detection, the detection latency is primarily due to the window size and stride. FIG. 10 presents a demonstration of how the sliding window approach affects detection latency for a single execution path. As the malware begins to execute, the estimated probability of malware in-creases. With each stride, the sliding window contains more timing samples from the malware, which increases the estimated probability of malware. Once the estimated probability of malware exceeds the threshold, the detector asserts the presence of malware.

CDF-Based Anomaly Detection Hardware

Figure 11:
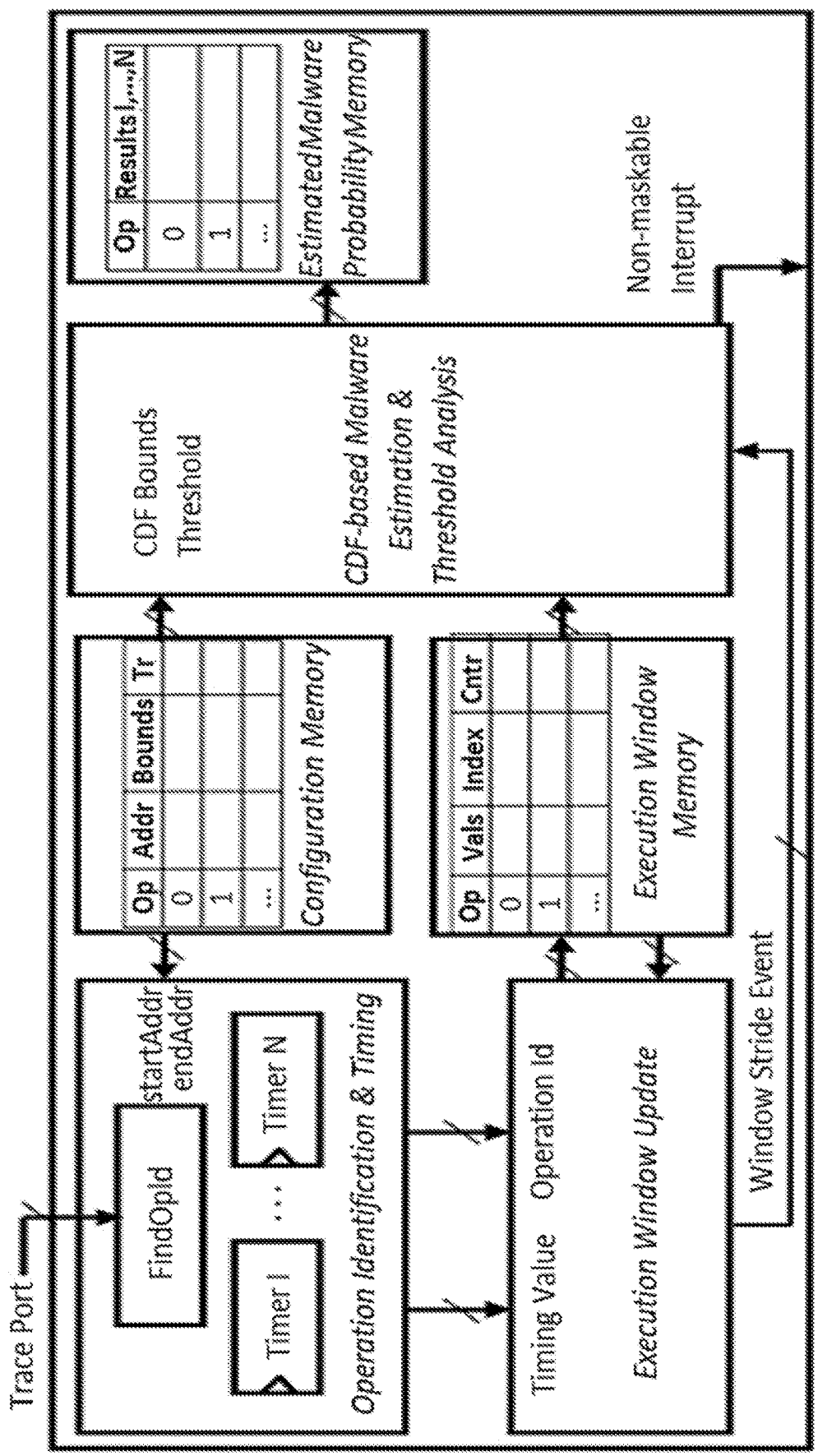
FIG. 11 shows a CDF-based anomaly detection hardware architecture in an embodiment of the present invention.

FIG. 11 presents an overview of the CDF-based anomaly detection (CDFAD) hardware. The CDFAD consists of three main components, the Operation Identification & Timing, Execution Window Update, and Malware Estimation & Threshold Analysis components. Additionally, the CDFAD uses three local memories to store operations' configuration, execution windows, and estimated malware probabilities, respectively. The Configuration Memory stores the monitored operations' start and end addresses, CDF boundaries, and thresholds. The Execution Window Memory stores the measured timing samples for the current execution window for all operations, as well as the number of new timing samples measured in the current stride. The Malware Estimation & Threshold Analysis Memory stores the current estimate of the probability of malware for all operations.

The Operation Identification & Timing component directly interfaces with the microprocessors' trace port to detect the execution of the monitored operations, using the operation's PC addresses. When the address for an operation's start address is detected, an internal timer is started to measure the execution for the current operation execution. That timer is then stopped when the operation's end address is detected. The Execution Window Update component receives the current measured timing value and operation ID from the Operation Identification & Timing and updates the corresponding entry within the Execution Window Memory. If the stride is reached, a window stride event signal is asserted to signal the Malware Estimation & Threshold Analysis component to perform the CDF-based analysis for this operation. The Malware Estimation & Threshold Analysis component reads the current execution window from the Execution Window Memory and the CDF boundaries and threshold from the Configuration Memory, calculates the $P_{est}o_i(M)$ of the current execution window, storing the results in the Estimated Malware Probability Memory component. If $P_{est}o_i(M)$ is greater than the threshold, the CDFAD asserts the non-maskable interrupt.

The CDFAD hardware was synthetized targeting an Artix-7 XC7A200T FPGA with Vivado 2016.4. The synthetized hardware support 32 operations, using 32-bit registers for both the operation's addresses and timers, and using block RAMs (BRAMs) to implement the local memories. The CDFAD hardware requires 6,481 lookup tables (LUTs), 7,666 flip-flops (FF), and three BRAMs (2×32 Kb, 1×64 Kb). No additional external memory or storage is needed. The CDFAD hardware has a maximum operating frequency of 128 MHz, which is sufficient for the target integration with a 100 MHz MicroBlaze based system. The CDFRAD hardware has a peak power consumption of 66 mW and average power consumption of 41.9 mW, which corresponds to a power overhead of only 3.56%.

Experimental Results

Figure 12:
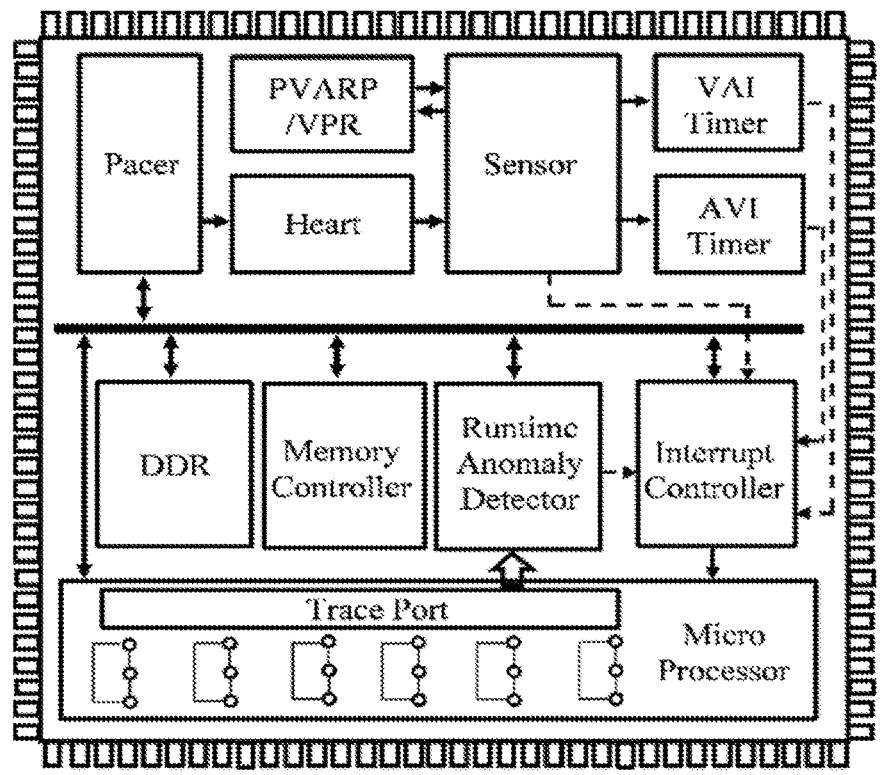
FIG. 12 shows a smart connected pacemaker system architecture in an embodiment of the present invention.

A. Smart connected pacemaker. A smart connected pacemaker was constructed and implemented a complete system prototype using the Artix-7 XC7A200T FPGA. The pacemaker prototype is representative of a complex embedded system that monitors, analyzes, stores, and transmits data, while providing life and safety critical operations. The pacemaker, shown in FIG. 12, includes a simulated heart, a tremor sensor, an impulse pacer, and four timers. The simulated heart beats irregularly and reacts to the impulse pacer controlled by the pacemaker's software. The cardiac activity sensor interfaces to the simulated heart and sends the measured activity to the microprocessor via interrupts. The output from the cardiac activity sensor also controls the Atrio-Ventricular Interval (AVI) and the Ventricular-Atrial Interval (VAI) timers. These timers are used to maintain the appropriate delay between the atrial/ventricular and ventricular/atrial activation and will generate an interrupt if the AVI/VAI exceeds a specific interval configured by a physician. The PVARP/VRP timers filter noise in the ventricular and atrial channels, respectively (Jiang et al., *Conf. on Tools and Algorithms for the Construction and Analysis of Systems*, pp. 188-203, 2012; and Singh et al., "The Cardiac Pacemaker Case Study and its Implementation in Safety-Critical Java and Ravenscar Ada", *Workshop on Java Technologies for Real-time and Embedded Systems*, 2012).

The pacemaker's software, which executes on a MicroBlaze processor, consists of three tasks and four interrupt service routines (ISRs). The ISRs interact with the pacemaker's cardiac activity sensor and timers. ISR operations include performing the atrial and ventricular pacing and recording ventricular and atrial activity. The first software task calculates the Upper Rate Interval (URI) and records cardiac activity to a daily log file. A second software task analyzes the cardiac activity and detects a high URI, which indicates the pacemaker cannot pace the heart correctly or that pacemaker's cardiac activity sensor has malfunctioned. In the operation of a high URI, the pacemaker immediate transmits a warning message to alert the physician. The third software task is responsible for communication, by which the physician can configure the pacemaker's settings, or a home monitoring device can access daily logs of the cardiac activity.

Finally, the CDFAD hardware was integrated within the sys-tem prototype, monitoring the signals of the MicroBlaze processor's trace interface to non-intrusively observe and analyze the system execution at runtime to detect anomalies (Xilinx, Inc. MicroBlaze Processor Reference Guide, UG984. 2016).

B. Detection rate and false positive rate. Using the four mimicry malware, the detection and the false positive rates of the CDF-based anomaly detection are evaluated. The true positive rate (TPR) (i.e., detection rate) is calculated as the number of malware executions classified as malware, divided by the total number of malware executions.

$$TPR = \frac{\text{Malware executions classified as malware}}{\text{Total malware executions}}. \quad (3)$$

Using a separate set of data, the false positive rate (FPR) is calculated as the number of normal executions classified as malware divided by the total number of normal executions.

$$FPR = \frac{\text{Normal executions classified as malware}}{\text{Total normal executions}}. \quad (4)$$

Table 1 presents the FPR for each execution path affected by the mimicry malware, the overall FPR across all paths, and the average TPR (i.e., detection rate) for the CDF-based anomaly detection compared to a range-based (RB) anomaly detection method (Lu et al. *ACM Transactions on Embedded Computing Systems*, Vol. 17(2), Article 38, pp. 1-27, 2017). The range-based method detects anomalies by determining when the timing of monitored operations falls outside of a [WCET, BCET] range.

While the ranges for operations can be either calculated using one of the many analysis techniques (Wilhelm et al., *ACM Transactions on Embedded Computing Systems*, Vol. 7(36), pp. 1-47, 2008), experimentally collected normal training data was used to construct the CDF-based model to determine the ranges, following the same approach proposed in Lu et al., ensuring a fair comparison. Additionally, the same operations were monitored within the same execution paths for the smart connected pacemaker for both approaches. Overall, the CDF-based detection achieves a 12.4% higher TPR compared to the range-based detection. The CDF-based detection also achieves a per-path and overall FPR of 0%, indicating the threshold determined during training effectively minimizes the FPR. In contrast, the FPR for the range-based approach is as high as 2.4%.

TABLE 1

False positive rates and true positive rates for CDF-based anomaly detection and range-based (RB) detection (Lu et al.).

| Detection Method | FPR (%) | | | | Overall FPR (%) | Avg. TPR (%) |
|---|---|---|---|---|---|---|
| | P 1 | P 2 | P 3 | P 4 | | |
| CDF | 0.00 | 0.00 | 0.00 | 0.00 | 0.00 | 96.2 |
| RB | 0.04 | 0.55 | 2.41 | 0.00 | 2.41 | 83.8 |

Table 2 presents the per-path TPR for each malware and the average TPR across all malware for the two detection methods. For Path 1, Path 3, and Path 4, the CDF-based anomaly detection has a TPR greater than 99% for all mal-ware. For Path 2, the CDF-based anomaly detection achieves a TPR greater than 91% for the File Manipulation and Fuzz 100% malware. For the Fuzz 20% malware, which exhibits the smallest deviation in execution timing and is thus the hardest to detect, the approach achieves a TPR of 80%. For the File Manipulation malware, the CDF-based detection approach yields a significant increase in the TPR compared to the range-based approach for Path 1, with an increase of 97.7%. Across all malware considered, the CDF-based approach has a higher TRP for Path 1. On the other hand, for Path 2 and Path 3, the range-based detection achieves a higher TPR for the two Fuzz malware, but again at the expense of an increase in the FPR. Overall, the CDF-based approach achieves a higher average TPR and lower FPR (i.e., 0% FPR).

TABLE 2

Per-path TPR for CDF-based anomaly detection and range-based (RB) detection (Lu et al.).

| Detection Method | Path | TPR (%) | |
|---|---|---|---|
| | | CDF | RB |
| File Manipulation | P1 | 99.8 | 2.1 |
| | P2 | 94.4 | 83.7 |
| | P3 | 99.5 | 100.0 |
| Fuzz 20% | P1 | 99.5 | 90.3 |
| | P2 | 80.0 | 100.0 |
| | P3 | 99.5 | 100.0 |
| Fuzz 100% | P1 | 99.0 | 62.9 |
| | P2 | 91.3 | 100.0 |
| | P3 | 99.5 | 100.0 |
| Infomation Leakage | P4 | 99.0 | 99.0 |
| Average | | 96.2 | 83.8 |

C. Analysis of design tradeoffs. Within the presented approach, the window size of 20 was determined at design-time to minimize the FPR and minimize hardware requirements. However, the window size also affects the TPR and detection latency. To understand and analyze these tradeoffs, the per-path TPR, average FPR, and detection latency was determined for different window size configurations, ranging from 20 to 200, as presented in Table 3. As the window size increases from 20 to 80, the TPR decreases for all paths and all malware. With further increases in window size, the TPR for some paths increases. For example, the TPR for Path 3 for the File Manipulation malware increase from 99.0% to 99.5%. Further increasing the window size to 200 results in only two cases in which the larger window size achieves a higher TPR than a window size of 20, specifically Path 3 for the File Manipulation and Fuzz 20% malware. Additionally, with a window size of 200, the FPR increases from 0% to 2.2%. Finally, as the window size increases, the malware detection latency increases linearly with the window size, requiring approximately 26 cycles per sample. Even though the window size was selected to minimize FPR and hardware area, a window size of 20 on average yields the highest TPR for the malware considered.

TABLE 3

Analysis of per-path TPR, average FPR, and detection latency for different window size configurations.

| Window Size | File Manipulation | | | Fuzz 20% | | | Fuzz 100% | | | Information Leakage | FPR (%) | Detection Latency (Cycles) |
|---|---|---|---|---|---|---|---|---|---|---|---|---|
| | P1 | P2 | P3 | P1 | P2 | P3 | P1 | P2 | P3 | P4 | | |
| 20  | 99.8 | 94.4 | 99.5  | 99.5 | 80.0 | 99.5  | 99.0 | 91.3 | 99.5 | 99.0 | 0.0 | 668 |
| 40  | 99.7 | 92.6 | 99.0  | 98.0 | 60.0 | 99.0  | 98.0 | 87.0 | 99.0 | 99.0 | 0.0 | 1192 |
| 60  | 99.6 | 88.9 | 99.0  | 97.0 | 60.0 | 99.0  | 97.5 | 82.6 | 99.0 | 97.5 | 0.0 | 1716 |
| 80  | 99.5 | 87.0 | 99.0  | 96.5 | 40.0 | 99.0  | 97.0 | 78.3 | 99.0 | 96.5 | 0.0 | 2240 |
| 100 | 99.4 | 81.5 | 99.5  | 95.5 | 30.0 | 99.0  | 95.5 | 73.9 | 99.0 | 98.0 | 0.0 | 2764 |
| 120 | 99.4 | 79.6 | 99.5  | 94.5 | 20.0 | 98.5  | 95.0 | 73.9 | 98.5 | 96.0 | 0.0 | 3288 |
| 140 | 99.4 | 77.8 | 99.5  | 94.0 | 20.0 | 98.5  | 94.5 | 73.9 | 98.0 | 94.0 | 0.0 | 3812 |
| 160 | 99.3 | 77.8 | 100.0 | 93.5 | 20.0 | 98.5  | 94.5 | 69.6 | 99.0 | 93.5 | 0.0 | 4336 |
| 180 | 99.3 | 75.9 | 100.0 | 93.0 | 20.0 | 99.5  | 94.5 | 69.6 | 99.5 | 95.0 | 0.0 | 4860 |
| 200 | 99.2 | 77.8 | 100.0 | 91.0 | 30.0 | 100.0 | 93.5 | 73.9 | 99.5 | 96.0 | 2.2 | 5384 |

Conclusions

The CDF-based timing anomaly detection detects small deviations in a system's timing distribution with high accuracy, achieving an average detection rate of 96.15% for the mal-ware considered. By determining a per operation and per path threshold, the presented approach yields a 0% false positive rate. The CDF-based anomaly detection further provides an estimate of the probability of malware that quantifies the possibility of deviation caused by malware execution, and potentially enables runtime mitigation methods to utilize this estimate to determine the appropriate actions.

Example 5—Probabilistic Threat Detection for Risk Management in Cyber-Physical Medical Systems The Internet of Things (IoT) represents the foundation of radical changes in cyber-physical systems (K. Carruthers, "IEEE Internet of Things Newsletter, 2016). There is rapid development and incorporation of Internet-connected devices in the present day, transforming several fields. This has been possible due to technical advancements of incorporating efficient computational resources, advanced sensors, and networking capabilities that allow communication of devices with the Internet as well as other devices (Rose et al., Internet Society, 2015). Unsurprisingly, the IoT is strongly influencing advances in healthcare and medical-device development. Such devices are now part of the digital health ecosystem. They facilitate continual patient monitoring and service, interoperability, and real-time data access. However, several critical challenges, including security, safety, privacy, essential performance, and regulatory compliance, have emerged.

Medical devices are exposed to a wide attack surface. Instances of malware, security vulnerabilities, and threats are proliferating. A significant number of recalls over the years have taken place (Kramer et al., "Security and Privacy Qualities of Medical Devices: An Analysis of FDA Post-market Surveillance," PLOS ONE, vol. 7, no. 7, 2012; J. Radcliffe, "Hacking Medical Devices for Fun and Insulin: Breaking the Human SCADA System," presentation at 2011 Black Hat Conf, 2011; and Halperin et al., "Pacemakers and Implantable Cardiac Defibrillators: Software Radio Attacks and Zero-Power Defenses," Proc. 2008 IEEE Symp. Security and Privacy (SP 08), 2008, pp. 129-142). In addition to strict regulations required for medical devices by the US Food and Drug Administration (FDA), recommendations for risk assessment and management for premarket and postmarket security management are now becoming standard ("Guidance for the Content of Premarket Submissions for Software Contained in Medical Devices," www.fda.gov/downloads/MedicalDevices/DeviceRegulationandGuidance/GuidanceDocuments/ucm089593.pdf, US Food and Drug Administration, 2005; and "Postmarket Management of Cybersecurity in Medical Devices," www.fda.gov/downloads/Training/CDRHLearn/UCM537944.pdf, US Food and Drug Administration, 2016).

To ensure safety, security, and privacy in the presence of unknown security threats, devices should dynamically detect and assess risk, subsequently taking automated mitigative actions when the risk is elevated. This requires that a risk assessment model be developed at design time with runtime security threat detection, adaptive risk management policies, and automated mitigation schemes during deployment. Flexible security frameworks that incorporate conventional security solutions along with in-device security are required (Babar et al., Proc. 2011 2nd Int'l Conf. Wireless Communication, Vehicular Technology, Information Theory and Aerospace Electronic Systems Technology (Wireless VITAE 11), 2011, pp. 1-5). Toward this goal, a multimodal-device design was previously proposed with a composite risk model (Rao et al., Proc. 2017 Spring Simulation Multiconf. (SpringSim 17), 2017). The present example describes the incorporation of a novel real-time threat detector with an adaptive risk assessment methodology to ensure unabridged threat mitigation during the deployment of devices.

Much work exists in real-time threat assessment and management, especially in intrusion detection systems (Blyth and P. Thomas, J. Computer Security, Vol. 14, no. 6, 2006, pp. 513-534; and Cherdantseva et al., Computers and Security, Vol. 56, February 2016, pp. 1-27). Probabilistic methods like Markov models have been utilized to detect threats in such systems (Ames et al., Recent Advances in Intrusion Detection, LNCS 4219, 2006, pp. 145-164). However, in critical medical cyber-physical systems that are characterized by strict timing constraints, expedient and robust threat detection is essential (Lu et al., Proc. $20^{th}$ Asia and South Pacific Design Automation Conf., pp. 809-814, 2015). This necessitates the analysis of the distribution of events in each execution window compared to the current state sample as in Markov models. Thus, cumulative distribution functions (CDFs) were utilized for modeling the normal device behavior, which is used to quantify the likeliness of security threats at runtime. This probabilistic threat detector is used to assess and manage the system's risk, which results in a precise real-time update of the current system risk. This approach reduces the false-positive rate to prevent erroneous activation of a mitigation scheme that may otherwise lead to accidental loss of functionality. This article presents a comprehensive framework for threat detection and mitigation during deployment of medical devices. This framework is demonstrated through a smart-connected-pacemaker scenario.

Framework Design Overview

Figure 13:
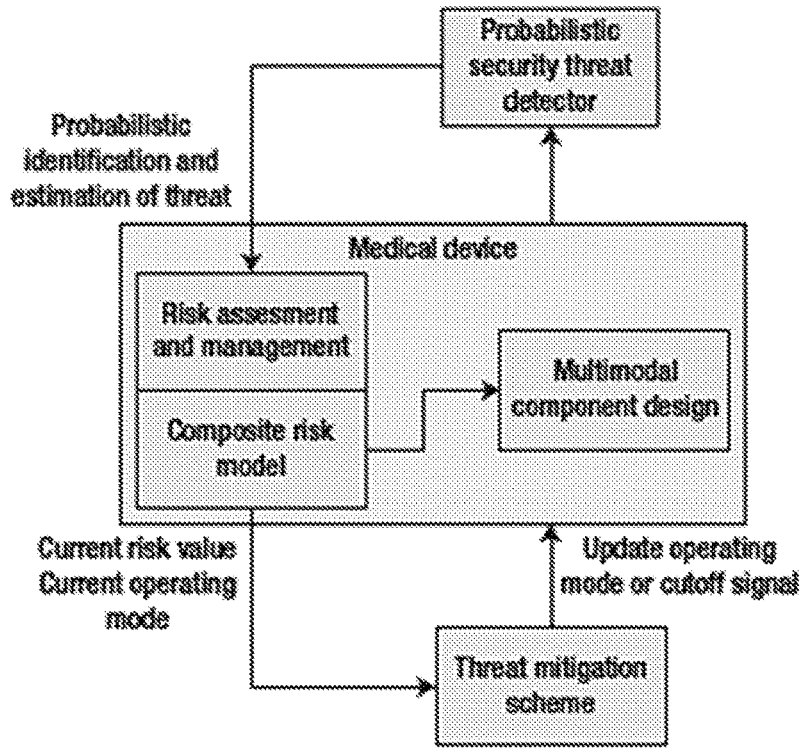
FIG. 13 shows an overview of a framework for runtime threat detection, risk-based assessment, and automated mitigation in medical devices in an embodiment of the present invention.

An overview of this approach is presented in FIG. 13. The medical device has been designed based on the multimodal approach. The composite risk model associates risk values with the device's various software and hardware components. For the details of the composite risk model and multimodal design, see "Composite Risk Modeling for Automated Threat Mitigation in Medical Devices" (Rao et al., Proc. 2017 Spring Simulation Multiconf. (SpringSim 17), 2017). Based on the current system risk, which will be updated dynamically, the threat mitigation either disallows access to the affected component or updates the current operating mode to mitigate the risk while sustaining essential functionality. This example focuses on the integration of threat detection with risk assessment and management during medical-device deployment.

Threat Detection Design

The runtime threat detector monitors the execution sequences and timing of all critical system operations, specifically those within the system's composite risk model. The threat detection analyzes the timing of these system operations within a sliding execution window. For each execution window Ew, the CDF is calculated and compared to predefined bounds of the system's normal execution behavior. Using a CDF-based model of the system behavior under normal execution scenarios enables the runtime threat detection to estimate the presence of a threat affecting each operation. Utilizing the internal execution time provides protection against cloaked threats that follow the correct execution sequence but whose behaviors still have an impact on the operation execution time, a feature lacking in sequence-only detectors. This estimation compares the overlap between the CDFs obtained at runtime and the CDFs obtained from the system under normal circumstances.

To construct the normal execution model, the software application is statically analyzed to identify the critical operations defined in the device's composite risk model. The system is executed under different execution scenarios, and timing measurements are collected for all operations. The timing of the operations is obtained automatically and nonintrusively through the system's trace port (in a case study, the pacemaker's), which, importantly, does not perturb the device's execution.

The CDF analysis checks the timing across all execution windows for the training data and calculates the upper and lower distribution bounds for each operation. This is used at runtime to detect any deviation from the expected execution. For a single operation, the estimated threat probability depends on the complement of the overlap between the runtime CDFs and the CDF boundaries of the normal system execution. Finally, to eliminate or minimize false positives, cross-validation is used to determine the maximum estimated threat for normal operation execution. This threshold $P_{th}$ is used to filter out false positives at runtime.

Risk Assessment and Management Unit

The estimated threat probabilities from the runtime threat detection are directly utilized as the input of the risk assessment to update the risk values of system components and operations. A level-based approach is used to update the risk for individual system operations based on the estimated threat probability. Risk values are updated as follows:

$$\text{risk}_{updated} = \text{risk}_{initial} + P_t \times C_l, \quad (5)$$

where Pt represents the estimated threat probability affecting the component and $C_l$ is the level-based constant. During device design, every component is assigned an initial base risk value. This is determined by the criticality of the component or an expert's judgment, which is updated during deployment according to Equation 1. $C_l$ is deduced as:

$$C_l = \begin{cases} 0, & P_t < P_{th} \\ \left\lceil \dfrac{P_t}{P_{th}} \right\rceil, & \text{otherwise} \end{cases},$$

where Pth represents the probability thresholds. As $P_t$ increases, $\text{risk}_{updated}$ will increment faster, and if it is slightly above the threshold (still a security threat), the risk will increase at a slower rate. The formulation also restricts the risk from increasing too rapidly by truncating $C_l$ to the smallest succeeding integer value. If the threat persists, the cumulative risk will continue increasing, relative to the threat probability, until the device's operating threshold is reached. At this point, the mode of operation is switched to a lower mode.

A key aspect to consider while incorporating the proposed framework is to assure that the latency of the overall risk management is well within the temporal limits of activating the principal intended action by the medical device (Martin et al., Applied Ergonomics, Vol. 39, no. 3, 271-283, 2008). Thus, once the threat is detected, the mitigation latency L is calculated as:

$$L = n \times t_{update} + t_{mode}, \quad (6)$$

where n is the number of windows that were analyzed between the time when the threat was introduced in the system and the time when the current-mode maximum risk was reached, $t_{update}$ is the time required for the risk to be updated, and $t_{mode}$ the time to switch-mode is modes. n depends on multiple factors, mainly the threat and execution window $E_w$. In the real world, there is no method to precisely know when the threat was introduced into the system. Therefore, the latency is calculated by conducting experiments and measuring the estimated probability of the threats. The present threat mitigation response of this example adapts according to the measured estimated probability.

Smart-Connected-Pacemaker Scenario

Figure 14:
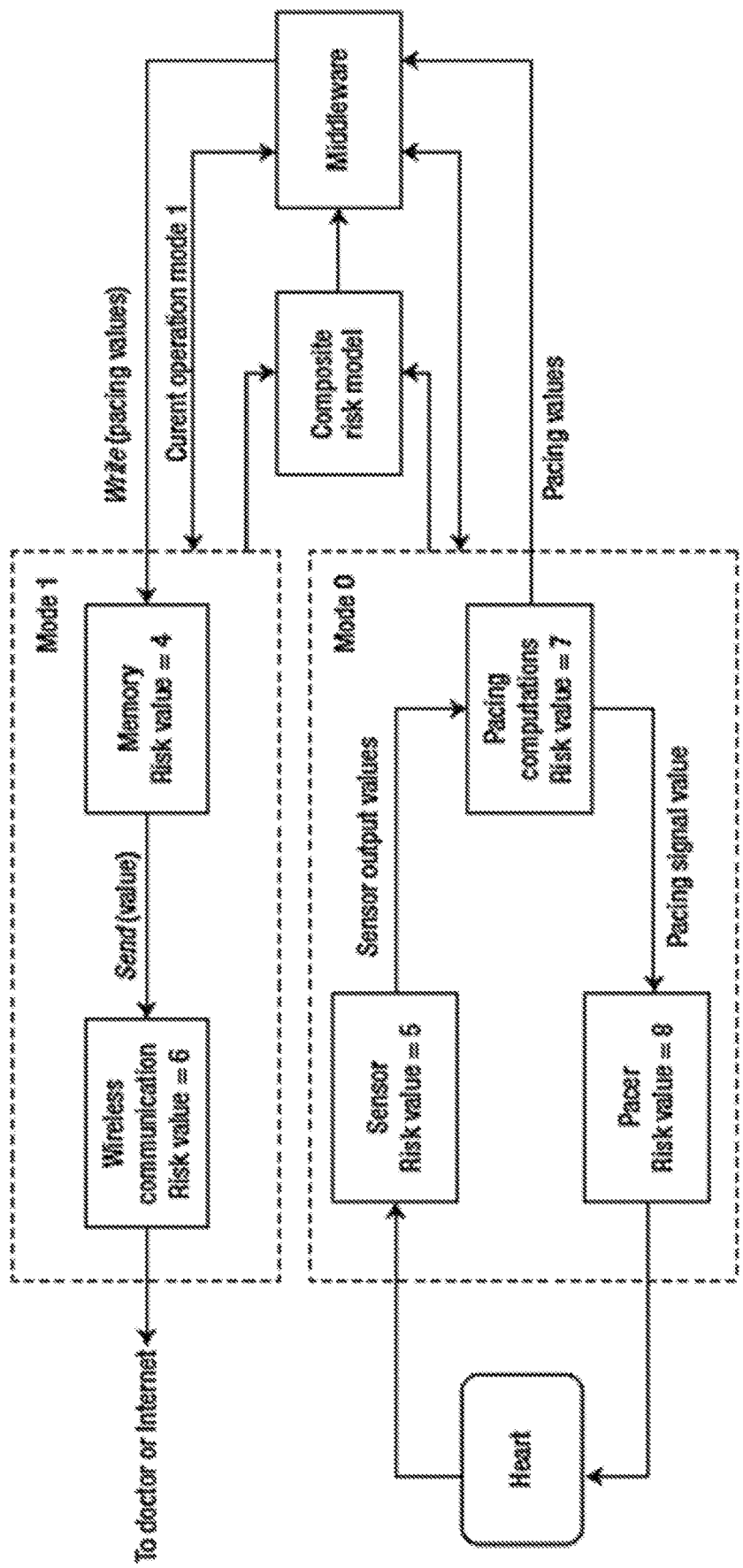
FIG. 14 shows a multi modal smart connected pacemaker with its composite risk model in an embodiment of the present invention.

A smart-connected-pacemaker prototype was developed and implanted malware therein to demonstrate the present framework (Lu et al., Proc. 20th Asia and South Pacific Design Automation Conf., pp. 809-814, 2015). FIG. 14 shows the pacemaker design, based on the multimodal approach with the composite risk model as described in "Composite Risk Modeling for Automated Threat Mitigation in Medical Devices" (Rao et al., Proc. 2017 Spring Simulation Multiconf. (SpringSim 17), 2017). For demonstration, two operational modes were considered, but it is noted that the present framework can accommodate any number of modes as required by the designer. Higher levels of abstraction were modelled for the device components (e.g., Bluetooth or WiFi would both be included in the wireless-communication component) to emphasize the operation of the proposed framework. The critical components required for the pacemaker's essential performance include the pacer, sensor, and pacing-computations component, which are incorporated in Mode 0. The other components are used in Mode 1, as they do not contribute to the essential functionality. Hardware-software middleware facilitates the secure transfer of data and signals between operational modes. The middleware is also responsible for analyzing the runtime threat detection, updating the risk model, and determining what mitigation strategy to invoke when a threat is detected. The device is assumed to run with full functionality in the highest mode. Note that the cumulative risk for Mode 0 is 20 and the cumulative risk for Mode 1 is 30.

Figure 15:
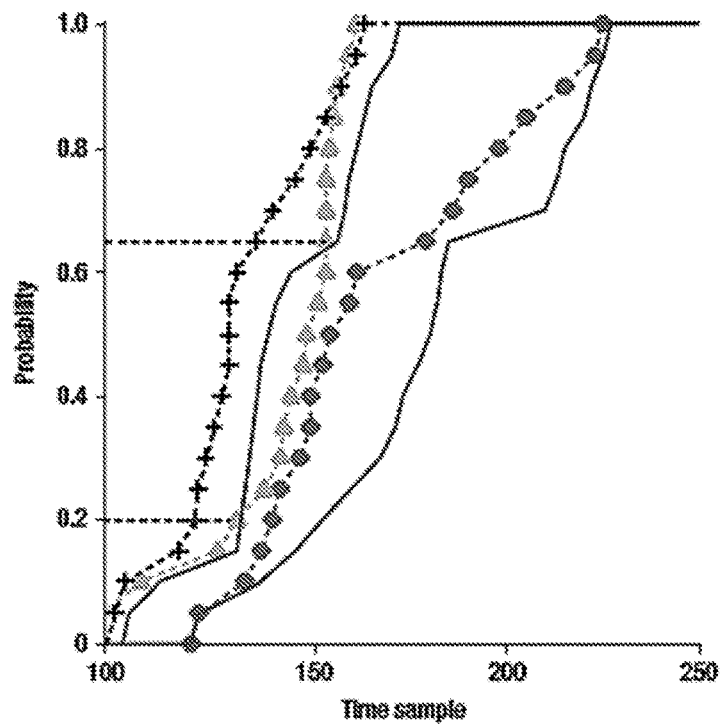
FIG. 15 shows an example of CDF-based threat estimation based on real data from the smart-connected-pacemaker prototype in an embodiment of the present invention. The solid line represents CDF (cumulative distribution function) bounds. The remaining lines (crosses, circles, and triangles) are runtime CDFs with estimated threat probabilities of 100%, 0%, and 55%, respectively.

Making the value of $C_I$ dependent on both the estimated threat probability and the threshold allows the system to increase the risk at either a faster or slower rate for different scenarios. FIG. 15 presents how the threat probability is calculated in the present scenario. The red solid line represents the CDF bounds for the normal execution model. The black, blue, and green lines represent the CDFs for three runtime execution windows. The black CDF is completely outside the boundaries and thus has an estimated threat probability of 100%. In contrast, the blue CDF is completely inside the boundaries, and thus the threat estimate is 0%. For the green CDF, there is partial overlap with the predefined boundaries, and the probability is estimated as the percentage of points of the CDF that fall outside the boundaries. The threat probability is equal to 1−(0.65−0.20), or 0.55, indicating there is an estimated 55% chance of a threat.

An illustrative example shows how the shift in modes is done based on the estimated threat probability. Using FIG. 14 as a starting point for the example and Mode 1 as the initial operating mode, it can be observed that the wireless-communication component has a risk value of 6 for the current execution. For simplicity, only malware that affects the wireless-communication component where $R_{th}$ (wireless)=5% was considered.

Figure 16:
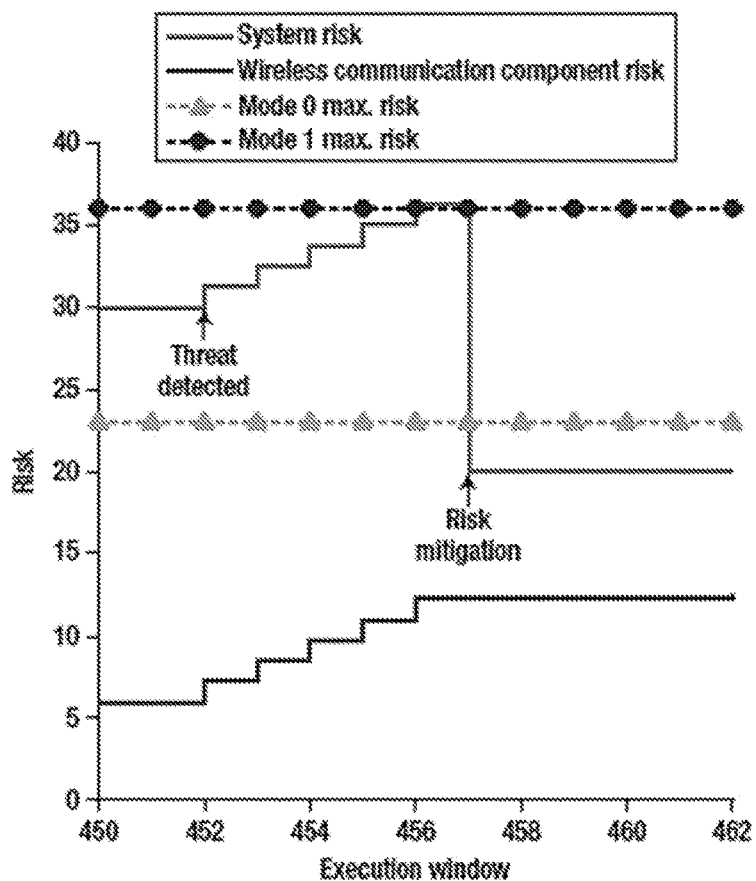
FIG. 16 shows a mode switch scenario in an embodiment of the present invention.

From the conducted experiment, FIG. 16 shows how the wireless communication component's risk (the red line) increases over time, based on the estimated threat probability. As the threat persists, the risk continues to increase, until the cumulative risk (the blue line) exceeds Mode 1's maximum risk threshold (the black line). In response, the middleware mitigates the risk by transitioning to Mode 0, thereby reducing the overall system risk. Additionally, the affected component is no longer used in Mode 0.

In this scenario, runtime threat detection is performed on an execution window corresponding to five iterations of the communication component. As such, the detection latency of five execution windows is equivalent to 25 iterations of the communication thread. The principal intended action of a pacemaker is to trigger a pulse to ensure a normal heart rate from 60 to 100 beats per minute, translating to 1 beat every 1 to 0.6 seconds. Utilizing Equation 2, the total threat detection and mitigation latency L is approximately 375 ms, which is well within the lower threshold time of 600 ms to trigger a normal beat.

Example 6—Statistical Time-Based Intrusion Detection in Embedded Systems

Broadly defined, there are two types of essential security measures for securing embedded systems. Proactive measures commonly include communication protocols and static application security testing, among others, but system designers must also consider scenarios in which attackers can circumvent a system's defenses. Reactive security measures are also needed to analyze the system at runtime to determine if malware is affecting the system execution. Signature-based detection systems (e.g. an antivirus running in a computer) focus on matching known traces in its database, because of this it is not able to protect against newly found threats (i.e. zero-day attacks) (Holm, H., *Hawaii International Conf. on System Sciences*, 2014). Anomaly-based detection systems create a model based on the normal behavior of the system and detect any deviation from the expected behavior. One of the most common approaches is monitoring the execution sequence of the system's function calls (Chandola, et al., *ACM Computing Survey*, 41(3), 2009; Zhang et al., *Conference on Compilers. Architectures and Synthesis for Embedded Systems*, pp. 43-54, 2005; and Arora et al., *Conference on Hardware Software Co-design and System Synthesis*, pp. 106-111, 2006). Every time a function is executed out of the expected order, sequence-based anomaly detection flags it as malware. However, these type of anomaly detectors do not provide protection against mimicry malware. Mimicry avoids detection by interleaving malicious functions within normal functions, avoiding executing functions out of order, but successfully carrying out the attack by eventually reaching the necessary functions following the normal execution sequence.

Timing-based anomaly detection exploits the fact that many embedded systems have tight timing constraints to additionally detect deviations in the execution times of a system's operations. Although mimicry malware doesn't execute any function out of the expected order, the malicious actions have a noticeable effect on the internal timing of the system. Thus, utilizing a system model that combine sequence and timing based execution enables more robust malware detection against mimicry malware.

However, existing timing-based anomaly detection primarily relies on so called lumped timing measurements that can have significant variations due to the timing overhead incurred by interrupts, cache misses, and the system architecture. Alternatively, the timing data can be broken down into subcomponents with tighter distributions that enable better malware detection. A timing model with three subcomponents splits the timing measurement into different measurable subcomponents, including the intrinsic software execution (i.e. ideal software execution time without the overhead due to the operating system, interrupts, etc.), the time overhead due to the instruction cache (I$) misses, and the timing overhead due to data cache (D$) misses.

This example presents a statistical timing-based anomaly detection methods that analyzes the cumulative distribution functions (CDF) of timing subcomponents within sliding execution windows. Also presented is a path-based method for estimating the probability of malware based on observed timing measurements at runtime, and a methodology is presented for defining probabilities thresholds to minimize false positive rates, which is a critical concern for any anomaly-based detection method. The novelty of this example resides on analyzing the subcomponent timing using cumulative distribution functions along execution sequences, to create a model of the system.

Related Work

Several efforts have been made to develop sequence-based anomaly detectors. Patel et al. use a control flow map to monitor execution sequences of the target system (*Design Automation Conference*, pp. 858-861, 2008; and *IEEE Transactions on Very Large Scale Integration Systems*, No. 99, pp. 1-14, 2010). However, their detection methods require code instrumentation to transmit measurements to a dedicated processor for analysis, which incurs up to a 44% performance overhead and 27% area overhead. Embedded systems usually have very tight constraints, especially medical systems. Thus, these overheads may be infeasible or cost prohibitive.

Although sequence-based detectors can achieve good detection rates, they are unable to protect the system against mimicry attacks. Wagner et al. demonstrated that sequence-based detectors are unable to detect mimicry malware. They did this by evaluating different sequence-based detectors against mimicry malware. However, although mimicry malware does not alter the execution sequence, it still influences the internal timing. The mimicked normal operations commonly use dummy or null parameters, and the malicious operations change the internal functionality of said operations, which impacts the operation execution time. Even small changes in the timing of execution of a single function can have measurable impacts to the timing of other operations.

Creating a model of the system by analyzing the timing behaviors provides additional resilience against mimicry malware, as has been demonstrated by several existing methods.

Lu et al. defined several methods to analyze the timing distribution and create anomaly detectors using non-intrusive hardware. Their approaches include a distance-based approach and a support vector machine approach. The granularity of their approach is at a subcomponent-level, in which they separate the timing information into three different times, namely D$, I$, and intrinsic timing. However, their approach separately analyzes the timing behavior of each execution of each operation, meaning that it does not consider the statistical distribution of timing behaviors nor the timing of entire execution paths.

Yoon et al. presented SecureCore, which focuses on analyzing the timing distribution at the basic block level. At runtime, the timing of the basic block is measured, and the probability of that measurement being observed is estimated. If the probability is below a previously defined threshold, the execution is flagged as malicious. Since false positives may deteriorate the performance of the system, defining the correct thresholds is critical. However, it false positives are inherent in this approach, and when applied to operations at a coarse granularity (e.g. system or function calls) the false positive rate can be as high as 66%.

Other efforts include monitoring the control flow sequences within sliding windows (Zhang et al., Conference on Compilers. Architectures and Synthesis for Embedded Systems, pp. 43-54, 2005), analyzing the data dependencies between internal operations by monitoring the dataflow of an application (Chen, et al., *USENIX Security Symp.*, pp. 177-192, 2005), creating stochastic models based on Markov chains (Frossi, et al., *Conf. on Detection of Intrusions and Malware, and Vulnerability*, pp. 206-223, 2009) that describe any possible sequence of events along with their probabilities, and modelling the dataflow as the relationship between the arguments for different function calls or control flow operations (Bond, et al., *Programming Languages and Analysis for Security*, pp. 1-10, 2010; and Bhatkar, et al., *Symposium on Security and Privacy*, pp. 15-62, 2006). However, these would be infeasible in the present target systems due to performance or area overheads, data not being accessible at runtime, or their susceptibility to mimicry malware.

Assumptions and Threat Model

To appropriately evaluate the proposed model, several assumptions about the target systems were made. It is assumed the considered malware has already been able to gain access to the system. How the malware was able to gain access to the system is out of the scope for this example, and it doesn't influence the evaluation of the proposed model. All malware were implemented as mimicry malware, done by interleaving malicious operations within normal operations. Since mimicry malware does not violate the execution sequence, therefore, a sequence-based anomaly detector would not be able to detect any of these malware.

Seven mimicry malware (Hartmann, et al., *Conf. on Cyber Conflict*, 2013; Kim et al., "Cyber attack vulnerabilities analysis for unmanned aerial vehicles," *The American Institute of Aeronautics and Astronautics*: Reston, VA, USA, 2012; Sun et al., *Pacific Rim Conf. on Multimedia*, pp: 367-375. 2007; Sametinger et al., *Communication of ACM (CACM)*, Vol. 58 No. 4, pp. 74-82, 2015; and Wasicek et al., *Design Automation Conference*, pp. 1-6, 2014) were implemented targeting prototypes of a network connected pacemaker and an unmanned aerial vehicle (UAV). These malware all represent real threats from different systems that have been modified to attack present systems. The Fuzz Malware interferes with the normal behavior by "fuzzing" (i.e. randomizing) the data within the pacemaker's cardiac log. This malware is implemented at two different fuzzification levels, namely 20% and 100%. The Information Leakage malware breaks confidentiality by sending private patient's data from the pacemaker to an unauthorized party. A Data Manipulation malware modifies data stored inside both target systems. For the pacemaker, this malware modifies the cardiac log so as to mislead a physician. For the UAV, the malware manipulates the encrypted files that causes a failure when decrypting them. The Gain Scheduling malware manipulates the gains or gain scheduling logic, which could cause decreased performance or dangerous instability in the control systems of the UAV. The Image Fuzz malware renders an image unusable by adding a Gaussian noise during the compression process onboard the UAV. The Camera Obfuscation malware interferes with the correct functionality of the UAV's camera by altering the behavior of the camera's flash (i.e. increasing or disabling the flash), rendering the image unusable. Finally, the Key Leakage malware breaks confidentiality by stealing and transmitting the encryption keys of the UAV to an unauthorized party.

Figure 17:
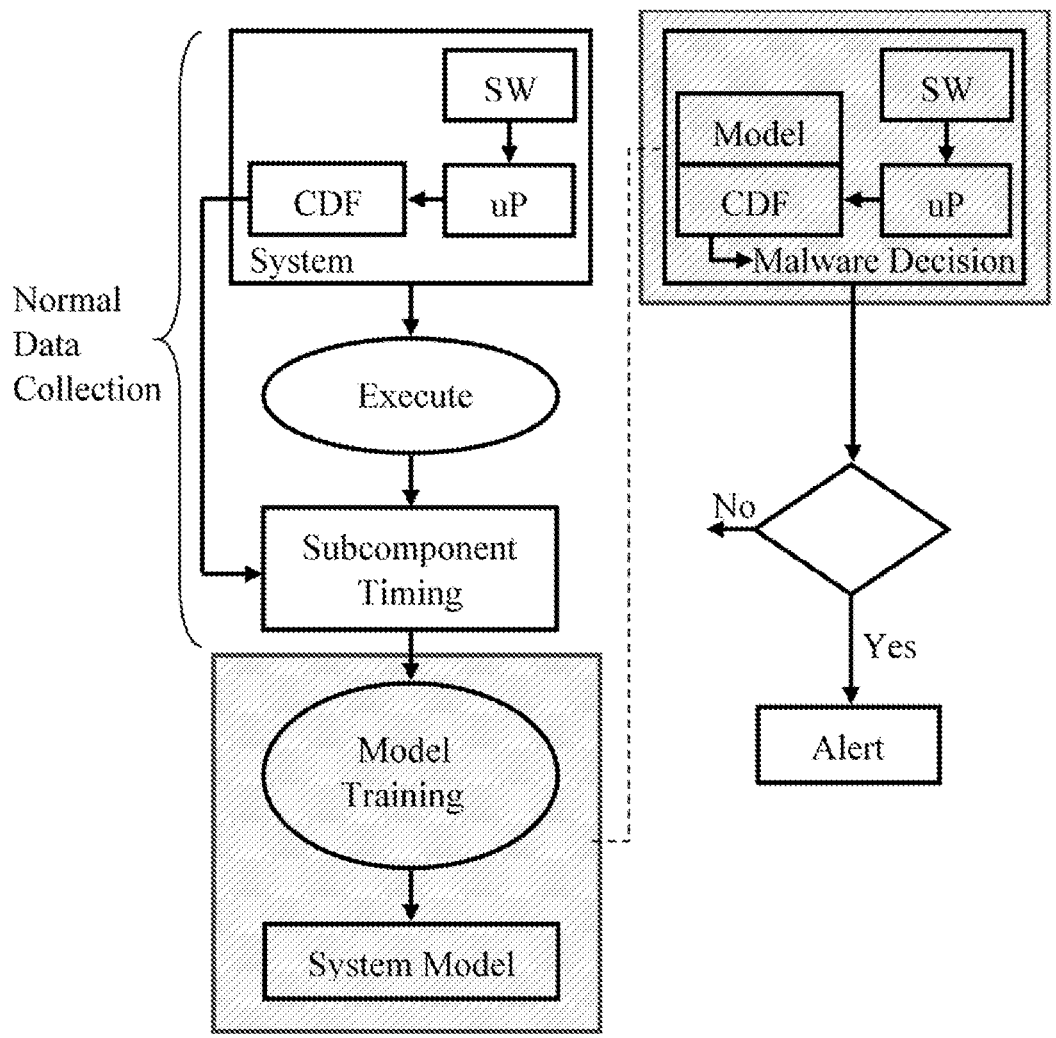
FIG. 17 illustrates a CDF-based anomaly detection using timing subcomponents in an embodiment of the invention.

FIG. 17 shows an overview of the proposed system architecture and methodology for CDF-based anomaly detection using timing subcomponents. The system is first executed under normal circumstances to collect the required amount of timing samples to create a model of the expected system execution behavior. A CDF hardware component analyzes the system non-intrusively by directly interfacing with the microprocessor's trace port, measures the time each operation takes to execute, and extracts the timing data of the different subcomponents.

Once the required amount of timing samples have been collected, the CDF-Analysis (highlighted in blue) creates the normal model of the system. The model is created by analyzing the timing distribution of the different subcomponents using Cumulative Distribution Functions (CDFs). This model is stored inside the CDF component to be used at runtime to determine if the runtime execution matches the expected CDF model or if timing deviation are due to malicious activities.

At runtime (highlighted in red) the state of the system is analyzed by looking at the state of the microprocessor through the trace port. Once enough timing samples have been collected, the CDF-Analysis is executed and the timing distribution is compared against the stored model. If the state of the system deviates beyond a previously defined threshold, an alert is sent.

Timing and Classification Models

The system is monitored by analyzing the state of the microprocessor by directly interfacing with it through its trace port. This approach is non-intrusive in the sense that the observation method does not affect the system behavior (i.e. no performance overhead is incurred). The CDF component detect the operation's execution by observing the program counter (PC) and looking for matching addresses against previously known addresses. Whenever an address matches the start address of an operation a timer starts, and whenever an address matches an end address, said timer stops.

Time measurements can be done at different granularities (e.g. operation-level, subcomponent-level). Building the model utilizing a finer granularity yield tighter bounds, which in turn improves accuracy. An operation is generally defined as a function call of the system, and the intrinsic timing is generally defined as the ideal execution time of the software without any overhead produced by the environment (i.e. OS, cache misses). On the other hand, the incidental timing is the overhead produced by the environment in which the software executes. The incidental timing is further broken down into the timing overhead produced by the I$ and D$ misses. The present approach measures the time of three different subcomponents: intrinsic, D$, and I$ timing.

Using these timing measurements, several classification models can be used to determine if the execution is malicious. An overview is presented of two existing subcomponent timing classification from Lu et al. (*ACM Trans. Des. Autom. Electron. Syst.*, 24, 3, Article 33, April 2019), including a Euclidean distance-based model and support vector machine (SVM) model, which are compared to in the experimental results. New proposed methods are then proposed using CDF-based statistical analysis of execution windows, one which performs malware classification at the operation level and one at the execution path level.

Distance based subcomponent (DBS) evaluates the data from each subcomponent together. The data points are arranged in a multi-dimensional feature space, with each dimension representing the timing data of one subcomponent (i.e. intrinsic, I$, D$). Clusters (i.e. spheres) are created from the data points utilizing the Euclidian distance, with the center of each one being their mean, and the farthest data point from the mean determining its radius. In this approach, every value that falls outside a sphere's radius is flagged as malware. Hierarchical clustering is used to cluster the normal data into multiple spheres, where the number of spheres has a direct effect on the tradeoff between detection accuracy and false positives. For this analysis, the number of spheres was set to 8, which yields a false positive rate below 1% for both target systems.

Support Vector Machines (SVM) use supervised learning theory for binary classification, which have been extensively used in the field of bioinformatics and image recognition. For anomaly detection, where only a model of normal system execution exists, the decision of whether the incoming data belongs to the one normal class can be solved using a one-class SVM (Chandola et al.), which are particularly useful when a higher number of features to train the system are available. In this case, the timing subcomponents are the features used by the SVM. The advantage of SVM against other existing machine learning techniques is its lower complexity and requirement of only needing normal timing measurements to train the model (Kulkarni et al., "Real-time anomaly detection framework for many-core router through machine learning techniques," *Journal on Emerging Technologies in Computing Systems*, 2016). Using the Schölkopf's model (Schölkopf et al., *Advances in Neural Information Processing Systems*, 12, pp. 526-532, 1999) all features of the training data (i.e. subcomponent timing data) are mapped into a hyperplane, maximizing the distance between the hyperplane and the original feature space. A binary function is then used to make the decision whether malware is executing inside the system.

A new Operation-based Historical CDF (OHCDF) based malware classification model is described that makes malware classification at the operation level. The CDF-Analysis is based on the Kolmogorov-Smirnov test (K-S Test), both of which focus on analyzing the data distribution. However, a traditional K-S test requires collecting thousands of timing samples before testing distributions, which is infeasible due to the resources and time needed to collect and store the data. Instead, a modified K-S test is used to statistically analyze the CDFs of operation's timing within a fixed size sliding execution window. Each window has two properties, the window size defines how many samples are stored inside the window at any given time, and the stride defines how many new samples needs to be recollected before executing the CDF analysis again.

The CDF-Analysis consist of two parts, constructing the model of the system, and calculating the runtime threshold. The normal data collected to train the system is split into two sets, the first is used to create the model of the system, and the second to calculate the threshold of the subcomponents per operation.

Boundary Construction

The timing samples of the first data set are split into small segments (i.e. windows). Each window overlaps 75% with the previous one, and having 25% of new timing samples (e.g. a stride of 5 for a window size of 20). The CDF of each window is then computed and compared against each other. The most extreme points found across all their CDFs, as shown in FIG. 7, define the CDF bounds of the normal behavior for an operation. These boundaries are used at runtime to estimate the probability of the execution being malicious based on how much it deviates from the CDF boundaries. The estimated probability of malware is defined as the percentage of the runtime CDF that falls outside the CDF boundaries, calculated as the complement of the overlap between the runtime CDF and the CDF boundaries.

Threshold Calculation

The second set of normal timing measurements is also split into overlapping windows and their CDFs are computed. For each window of each subcomponent, the complement of the overlap between their CDF and the subcomponent's CDF boundaries is calculated. The obtained value reflects how different the data inside the window is from the expected behavior. Next, the system finds the window that deviates the most from the expected behavior and set that as the threshold. In the present approach, the threshold defines the maximum deviation the runtime CDF can have, while still being considered normal.

Figure 18:
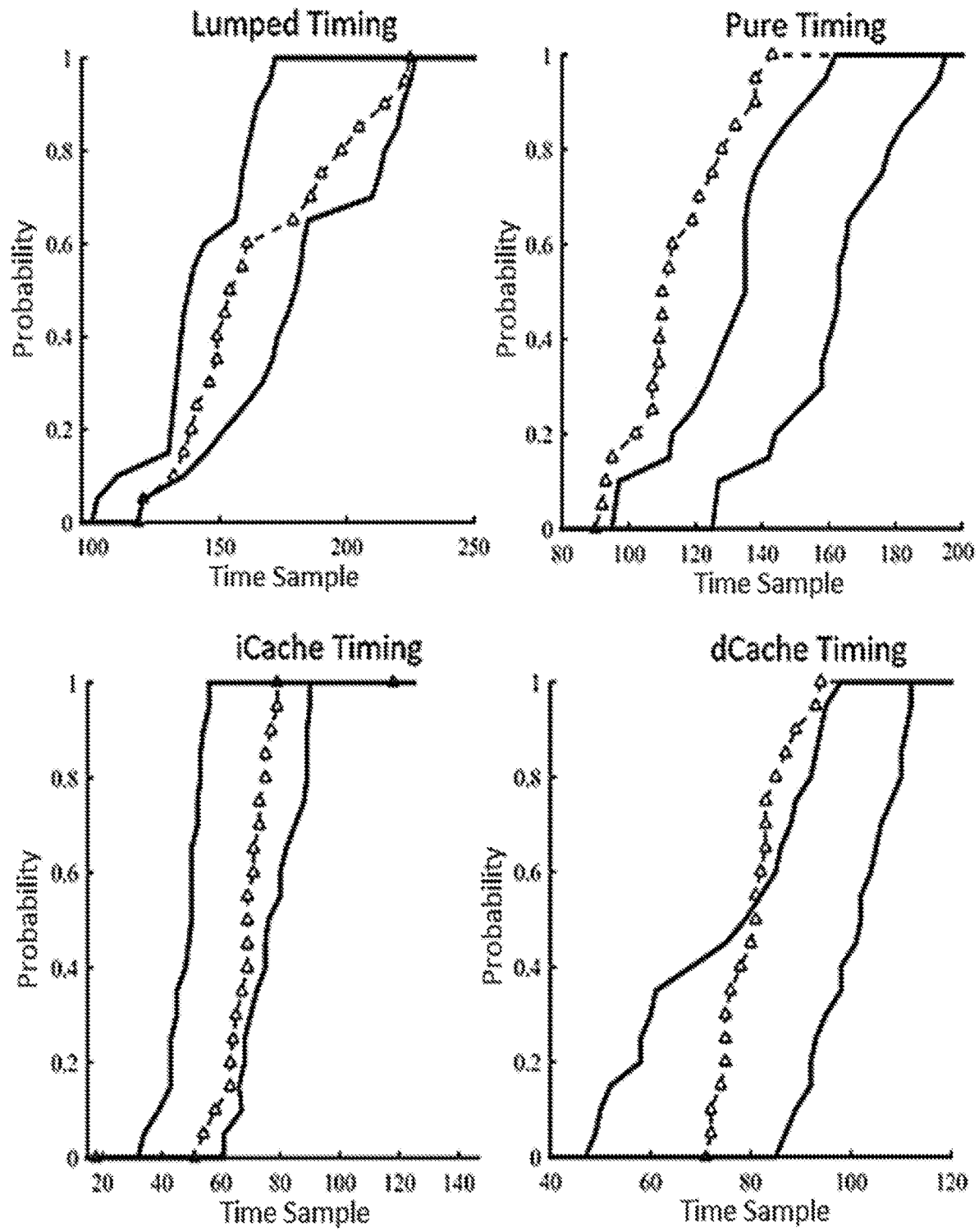
FIG. 18 comparisons between the normal timing (solid lines), and the fuzz malware timing (triangles) for a single execution window using the lumped timing and the subcomponent timing models. The malware is detected 100% of the time by the intrinsic timing, but would not be detected by the lumped timing.

At runtime, once enough data samples have been collected to fill a window, the CDF for each subcomponent is computed and compared against the subcomponent's previously defined CDF boundaries. The estimated probability of malware is then calculated and compared against the threshold of the subcomponent. An example of three different execution windows can be seen in FIG. 8. If the estimated probability of malware is above the threshold the execution window is flagged as malware, and a non-maskable interrupt is sent. Analyzing the timing data at the subcomponent level may reveal malware that would not be detected by a lumped timing as can be seen on FIG. 18. Profiling the system using the subcomponent timing data yields a finer granularity, which increases the accuracy of the anomaly detector. At runtime, if any of the subcomponents of an operation flags the execution window as malware, the operation is said to be malicious.

The OHCDF approach performs classification at the operation level, which can achieve high detection rates but with higher than desired false positive rates. Thus, this approach is further extended to create Path-based Historical CDF (PHCDF) that perform malware classification by aggregating the estimated probabilities of malware of several operations inside a path, yielding a more robust decision. A path is defined as a specific sequence of operations that execute at the same rate inside a software task. The path-based CDF analysis has an extra step compared to the OHCDF analysis, which is the aggregation of the thresholds and runtime CDFs per path.

Path Malware Probability Calculation

Estimating the probability of malware of an execution path depends on the independent probabilities of malware of the operations inside the path. The estimated probability of malware of a path is calculated using (1), defined as the probability that at least one of the operations is malicious.

$$P_{est}P_j(M)=1-\Pi_{i=0}^{n}(1-P_{est}o_i(M)) \quad (1)$$

Path Threshold Calculation

Previously, it has been shown that the decision whether the execution was normal or malicious was made by comparing the estimated probability of malware against the threshold. Similarly, the decision of whether the path execution is malicious or not is made by comparing the path's estimated probability of malware against the path's threshold. Calculating the path threshold is similar to calculating the estimated probability of malware of the path. However, instead of utilizing the estimated probabilities of malware, the previously calculated thresholds were utilized of all operations inside the path, as shown in (1). The resulting threshold is rigorous enough to accurately distinguish normal from malicious executions.

$$Tp_j=1-\Pi_{i=0}^{n}(1-P_{max}o_i(M)) \quad (2)$$

At runtime, once enough timing data has been collected to fill the windows of each operation in the path, the subcomponents CDFs are calculated and compared against the previously defined CDF boundaries to determine their individual probabilities of malware. The estimated probability of malware of the execution path is then calculated and compared against the t path threshold. If the estimated probability of malware is above the threshold the execution path is flagged as malware, and a non-maskable interrupt is sent. Like in the previous approach, this process is repeated for the three subcomponents considered, with any subcomponent flagging the execution as malicious resulting in the path determined to be malicious.

Experimental Results

Experiments were conducted with two target systems and a total of seven mimicry malware to demonstrate the advantages the CDF-based analysis of timing subcomponents compared to existing methods. Table 4 shows the two target systems considered along with a summary of their characteristics. The Unmanned Aerial Vehicle (UAV) is a prototype for an autonomous drone capable of automatically (or under manual control) collected images for target locations. The Pacemaker is a prototype for a connected pacemaker featuring remote connections for both automated communication of cardiac activity to healthcare providers and configurable pacing parameters by physicians. Across all malware classification method considered, any operation with an individual false positive rate above 5% was excluded from the timing model (i.e., the operation was not monitored at runtime). Cross validation (k=10) was used to determine the detection and false positive rates using 1000 execution per malware for the corresponding target system.

TABLE 4

Number of Tasks/ISRs, Number of operations, and malware affecting the Pacemaker and UAV target systems.

|  | Pacemaker | UAV |
| --- | --- | --- |
| # Operations | 43 | 51 |
| # Tasks/ISRs | 3/4 | 5/0 |
| Affecting Malware | Fuzz 20%, Fuzz 100%, File Manipulation, Information Leakage | Gain Scheduling, Image Fuzz, Data Manipulation, Key Leakage, Camera Obfuscation |

A hardware implementation of PHCDF malware detector was designed and synthetized targeting an Artix-7 XC7A200T FPGA with Vivado 2016.4. The hardware supports 51 operations, using 32-bit registers for both the operation's addresses and timers, and using block RAMs (BRAMs) as local memories. The hardware requires 7,979 lookup tables (LUTs), 9,100 flip-flops (FF), and three BRAMs (1×254 Kb, 2×512 Kb). No additional external memory or storage is needed. The hardware component has a maximum operating frequency of 111 MHz, which is sufficient for the target integration with a 100 MHz MicroBlaze based system. The hardware component has a peak power consumption of 112 mW (with 65 mW being consumed by the BRAMs), and average power consumption of 80.74 mW, which corresponds to a power overhead of only 6.89%. It is noted that only the event detection and timing components need to operate at the processor frequency and using a dual clock configuration could enable lower energy consumption.

Figure 19:
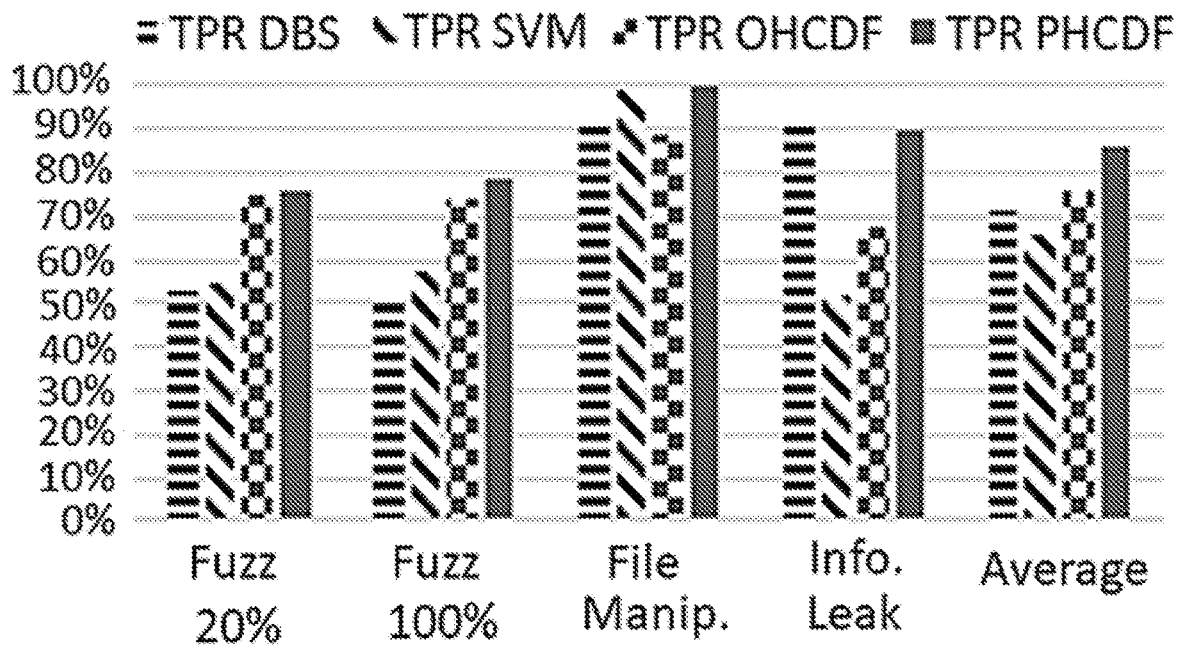
FIG. 19 shows detection rates for all malware affecting the pacemaker.

FIG. 19 presents the detection rates for each one of the malware affecting the pacemaker, for the four different approaches previously discussed. The SVM has the lowest average detection rate across all malware with 65.8%, although it's important to note that this is due to SVM having a very low detection rate for the Information Leakage malware, achieving just 52.0%. On the other hand, PHCDF achieves the highest average detection rate of 86.2%, with the highest detection rate for all malware except the Information Leakage malware. PHCDF achieves a detection rate of 76.22%, 78.57%, and 100% for Fuzz 20%, Fuzz 100%, and File Manipulation malware, respectively. While PHCDF achieves a 90% detection rate for the Information Leakage malware, DBS achieves a higher detection rate of 92.0%. In contrast, OHCDF has the second highest detection rate with an average of 76.1%, DBS achieves the third highest with 71.6%, and SVM the lowest with 65.8%.

Figure 20:
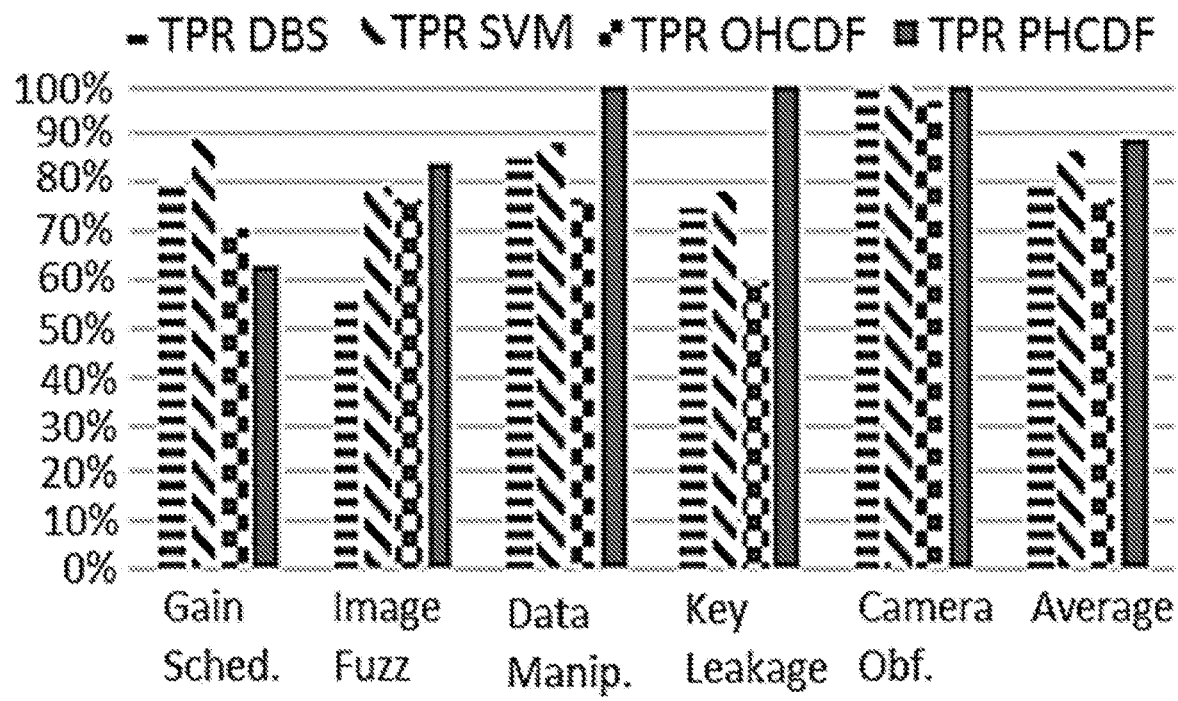
FIG. 20 shows detection rates for all malware affecting the UAV.

For the UAV, as shown in FIG. 20, OHCDF achieve the lowest average detection rate with 76.0%. PHCDF achieved again the highest average detection rate with 89.3%, having the highest detection rates on all analyzed malware except Gain Scheduling. However, it must be noted that Gain Scheduling might be an outlier, since the operation selection criteria left out most of the affected operations, lowering the detection rate drastically by up to 62.7%, as opposed to 83.8% for Image Fuzz, and 100% detection rates for the Data Manipulation, Key Leakage, and Camera Obfuscation malware. SVM yields the second highest detection rate with 86.8%, followed by DBS with 79.2%.

Table 5 shows the average false positive rate for both systems monitoring only operations whose individual false positive rate is below 5%. OHCDF yield false positive rates of up to 3.25% for the pacemaker, and 2.45% for the UAV, which is 2.18% higher than the second highest false positive rate for the pacemaker, and 1.56% higher the second highest false positive rate the UAV. Although SVM yields high detection rates, its false positive rates are the second highest for both target systems, yielding 1.07% and 0.89% for the pacemaker and UAV respectively. On the other hand, PHCDF yields the lowest false positive rates for both target systems, with 0.07% for the pacemaker, and 0.17% for the UAV.

TABLE 5

Average false positive rate for all different approaches, for both the pacemaker and UAV target systems.

|      | Pacemaker | UAV    |
|------|-----------|--------|
| DBS  | 0.0022    | 0.0079 |
| SVM  | 0.0107    | 0.0089 |
| OHCDF| 0.0325    | 0.0245 |
| PHCDF| 0.0007    | 0.0017 |

Conclusions

Path-based statistical analysis of subcomponent timing yields higher detection rates compared both to statistical analysis of individual operations and previously presented methods using Euclidean distance and support vector machines. Aggregating the results from the PHCDF analysis across all subcomponents yield high detection rates along with very low detection rates at the cost of a small increase in latency due to the system needing to gather enough new data samples before executing the CDF analysis again. For the considered target systems and malware, the PHCDF malware detection achieves the highest average detection rates with the lowest average false positive rates. Specifically, the PHCDF detection achieving 10.1% and 2.5% higher detection rates and 0.02% and 0.09% lower false positive rates compared to the next best detection methods for the pacemaker and UAV target systems, respectively.

Example 7—FIRE: A Finely Integrated Risk Evaluation Methodology for Life-Critical Embedded Systems Security risk assessment generally has two elements: (i) the probability of security threat, and (ii) impact on patient's safety if the vulnerability was exploited. It was assumed that a threat detector is incorporated within the system, such as the probabilistic threat detection/estimation design in, which achieves an average detection rate of 96% (Carreon, et al., *IEEE 36th International Conference on Computer Design (ICCD)*, pp. 522-529, 2018). Notably, the key requirement for the use of a threat detector is to provide an estimate of the threat probability at runtime that can be used for automated risk evaluation. In order to enable a system to automatically mitigate threats while ensuring life-critical operations remain uninterrupted, software for such systems can be designed in a multi-modal fashion based on the works of Rao et al. (*IEEE Software*, vol. 35, no. 1, pp. 38-43, 2018; and *Proceedings of the Annual Simulation Symposium*, Article 17, 2018). Such a system can perform runtime threat mitigation by automatically switching operating modes based on the evaluated system risk. However, the composite risk assessment model used in these works of Rao et al. is rudimentary and does not consider the impact on health and privacy according to established risk assessment guidelines. Comprehensive risk assessment also requires static and dynamic risk evaluation methods with robust experimental evaluation.

In this example, a detailed comprehensive risk evaluation approach, called FIRE—a Finely Integrated Risk Evaluation methodology for life-critical embedded systems, is described. It is believed that this is the first approach that considers the security threat impact on safety and privacy from the fundamental operations and augments an adaptive risk evaluation scheme during runtime of life-critical embedded systems. Specifically, this method provides the following contributions:

During design—Static risk evaluation: (i) base security-health and security-data-sensitivity impact scores are assigned in terms of Confidentiality, Integrity and Availability metrics to operations (Melt et al., "A complete guide to the common vulnerability scoring system version 2.0," *Forum of Incident Response and Security Teams (FIRST)*, 2007; and The MITRE Corporation, "Rubric for Applying CVSS to Medical Devices", available: /www. mitre.org/publications/technical-papers/rubric-for-applying-cvss-to-medical-devices, accessed September 2019). These scores are aggregated to the composing tasks using fuzzy union to generate task impact scores. Task risks are calculated using these impact scores. These task risks are accumulated to the successive mode risks. Mode risks are normalized in the range of 0-10.0 to adhere to popular standards established in CVSS (The MITRE Corporation, "Rubric for Applying CVSS to Medical Devices"). A hierarchical graph (FIRE graph) incorporating the control flow of the operations along with the associated risk scores is built for efficient calculation of both static and dynamic system risk. (ii) the threat probability thresholds of individual operators provided by a threat detector are then utilized, such as Rao et al. (*IEEE Software*, vol. 35, no. 1, pp. 38-43, 2018) to establish static risk thresholds for each software mode. During deployment, these thresholds will establish the mode risks beyond which the mode is likely compromised by a security threat.

During deployment—Dynamic risk evaluation: The same runtime threat detector provides threat probabilities of individual operations at runtime that are used to calculate dynamic system mode risks. Using the FIRE graph, the dynamic risk calculation are similar to the static risk ones, which benefits the resource constrained nature of life-critical embedded systems.

Sensitivity analysis: With the static mode risk threat threshold and dynamic mode risk evaluations established, a sensitivity analysis experiment is performed to analyze how the overall system risk is impacted by security threats affecting differing number of operations and with differing threat probabilities. This helps in understanding the criteria under which appropriate mitigative actions must be taken.

Related Work

Security risk assessment and management have been studied extensively over the years within software and cyber-physical systems (Kure et al., *Applied Sciences*, 8(6), pp. 898, 2018; and Boehm et al., *IEEE Software*, vol. 8, no. 1, pp. 32-41, 1991). Such methods typically utilize attack graphs, Bayesian networks or decision-driven modeling to express the likelihood of attacks combined with a vulnerability scoring system, e.g., CVSS. Comprehensive risk management is also considered throughout a system's lifecycle as in Kure et al. However, these risk assessment methods are created in the context of known attacks and vulnerabilities and are not deeply integrated within a system's design.

Furthermore, approaches with dynamic risk assessment only provide metrics and information about the system risk, and rely on manual risk management and mitigation methods (Ammann et al., *Conference on Computer and communications security* (CCS '02), pp. 217-224, 2002; and Poolsappasit et al., *IEEE Transactions on Dependable and Secure Computing*, vol. 9, no. 1, pp. 61-74, 2012). Such approaches may fail in life-critical systems that require runtime adaptive risk evaluation to sustain essential functionality during risk mitigation. Hence, risk evaluation methodologies are needed that: (i) enables the derivation and analysis of risks at the operation, task, and system levels based on established security scoring guidelines, and (ii) enables runtime adaptation of risks based on runtime probabilistic detection of threats.

Life-Critical Embedded System Overview

Figure 21:
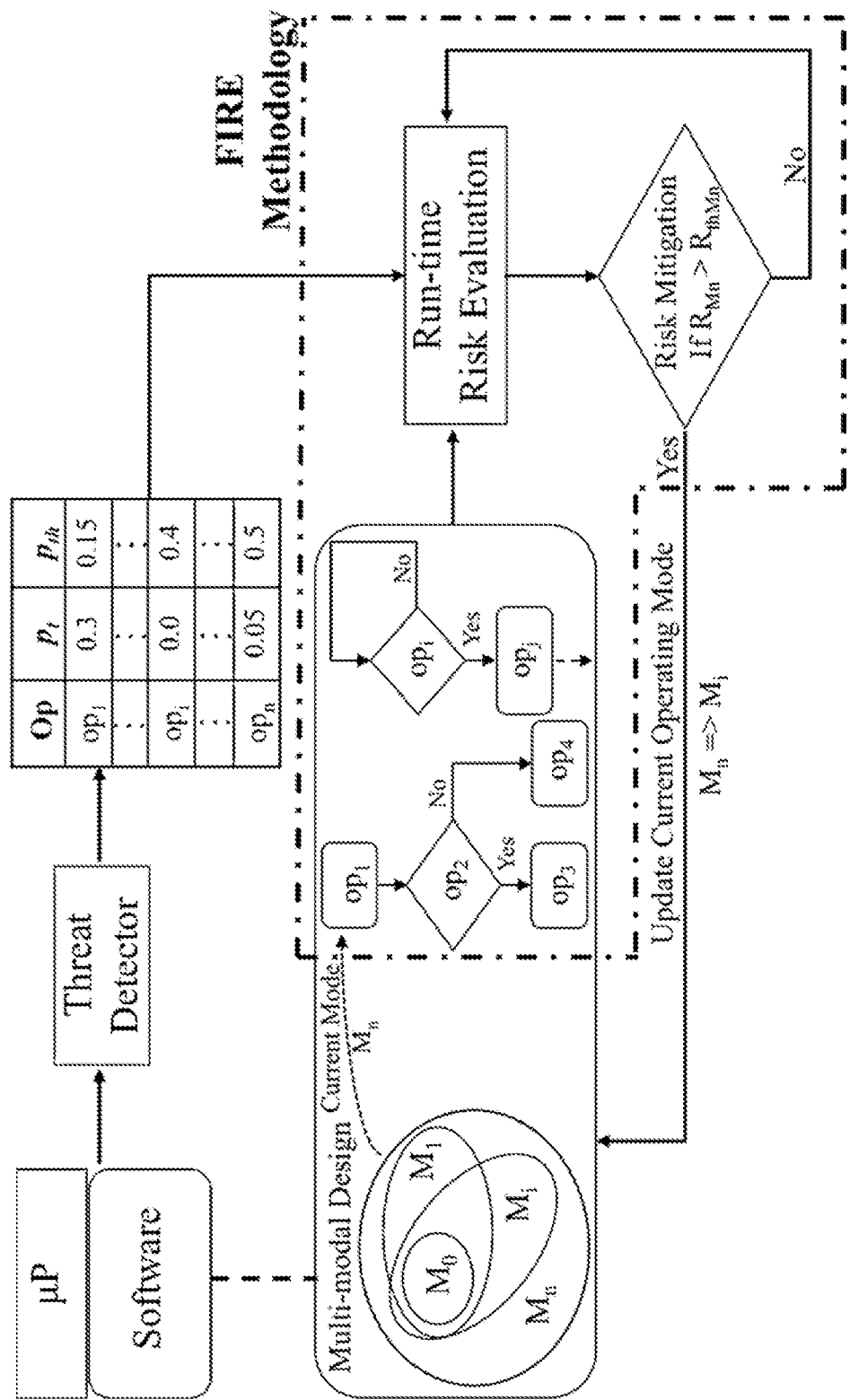
FIG. 21 shows a life-critical embedded system overview in an embodiment of the invention, including: Multi-modal software design, on-chip threat detector and estimator, and FIRE (runtime risk evaluation and mitigation).

It is assumed the architecture of a life-critical embedded system as illustrated in FIG. 21. The main components of such a system are:

On-chip Threat Detector and Estimator: The system is assumed to have a probabilistic threat detector and estimator (as in Carreon et al.) that monitors all the operations of the system at runtime to provide threat probabilities of the monitored operations {po1 . . . , poi, . . . , pon}. During design time, the probabilistic threat detector utilizes training data to establish per operation probability thresholds to minimize false positives and accurately determine the presence of security threats {ptho1, . . . , pthoi, . . . , pthon}.

Multi-modal Software Design: The system is composed of several modes {M0, . . . , Mi, . . . , Mn}, such that it can operate in only one mode at a time. M0 represents the essential mode that is required for the essential functioning of the system and is contained in every other mode. The assumption made by the work in Rao et al. (*Proceedings of the Annual Simulation Symposium*, Article 17, 2018) is that the software of the essential mode is flashed onto the secure core of the embedded system microprocessor. Each mode is composed of a set of tasks {T1, . . . , Ti, . . . , Tn}. Each task is a control flow graph of fundamental operations of the system {o1, . . . , oi, . . . , on}.

FIRE: As highlighted in FIG. 21, the FIRE methodology described in this work integrates a comprehensive risk evaluation method to the multi-modal design from the operations-to-modes level. During design, it utilizes the estimated probability thresholds of the monitored operations to establish static mode risk threat thresholds. During deployment, it actively gets estimated threat probabilities of the operations from the threat detector to calculate dynamic mode risks. The dynamic mode risks and the established static thresholds provide runtime risk assessment that aids in automatic risk mitigation decisions for life-critical embedded systems.

FIRE Methodology

Figure 22:
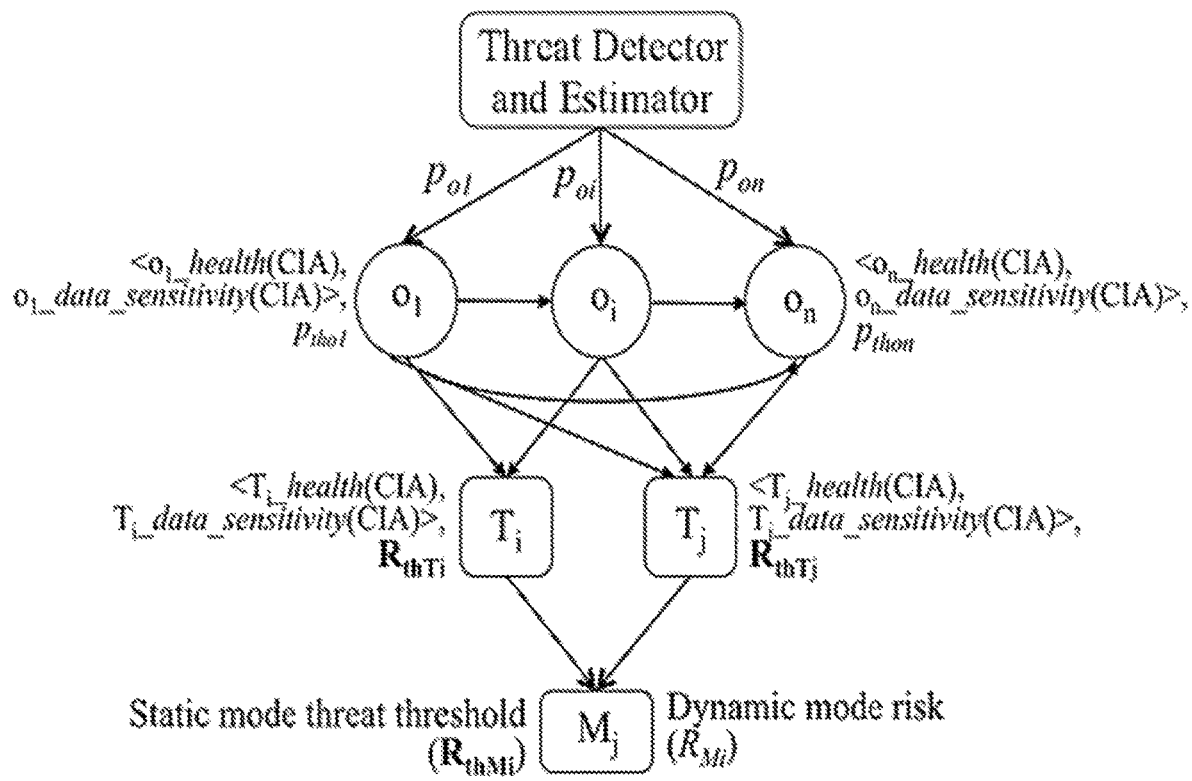
FIG. 22 shows an illustration of the FIRE graph.

The FIRE methodology operates in two stages: (i) static risk evaluation during design, and (ii) dynamic risk evaluation during deployment. A hierarchical risk evaluation graph is built and is called a FIRE graph, which is the execution flow of the system associated with the evaluated risks across all the hierarchical levels, as represented in FIG. 22.

Static Risk Evaluation

Operations level: Every operation is assigned a set of standardized Confidentiality, Integrity, and Availability (CIA) impact scores for health and data-sensitivity as $o_i < C_h, I_h, A_h, C_s, I_s, A_s>$. Health and data-sensitivity are aspects to be considered specific for life-critical embedded systems and is defined as the impact of the compromise of CIA on the health/safety of the patient and the data-sensitivity/privacy. The list of possible CIA impact scores and their corresponding assigned values are described in Table 6. To standardize the values and set bounds for risk evaluation, the values are in the range [0, 1.0] as described in CVSS.

TABLE 6

Health and data-sensitivity scores

| | | |
|---|---|---|
| None (N) | Operation has no impact on health and sensitivity. | 0.0 |
| Low (L) | Impact of exploited operation on health and sensitivity is minimal like semaphore_wait. | 0.22 |
| Medium (M) | Operation if compromised can considerably impact health and sensitivity but patient is not at risk like read_sensor. | 0.31 |
| High (H) | Operations if compromised may lead to life threatening health consequences like write_actuator or loss/invasion of critical sensitive data like calculate_insulin dose. | 0.56 |

Tasks level: With the operations' impact score assigned, these values are propagated up to the tasks in the FIRE graph by using Hamacher sum—a fuzzy aggregation operator (Liu, *IEEE Transactions on Fuzzy Systems*, vol. 22, no. 1, pp. 83-97, 2014). Fuzzy methods have been popularly used for security risk evaluation as they better represent likelihood of threats and impact values (de Gusmão, et al. *International Journal of Information Management*, vol. 36, no. 1, pp. 25-34, 2016). A Hamacher sum is employed as it is a t-conorm operator that emphasizes high possibility values in the effective final value. This aligns well with the case of security risk evaluation in life-critical systems, where a high possibility risk in one criterion (say Confidentiality) must result in an effective high risk value as well.

The aggregated task CIA impact scores are calculated as follows:

$$T_i < C_h, I_h, A_h, C_s, I_s, \quad (7)$$

$$A_s >= (o_1 < C_h, I_h, A_h, C_s, I_s, A_s > \times p_{o1}) \oplus \ldots (o_i < C_h, I_h, A_h, C_s,$$

$$I_s, A_s > \times p_{oi}) \oplus \ldots (o_n < C_h, I_h, A_h, C_s, I_s, A_s > \times p_{on})$$

where p is the threat probability of the operation provided by the threat detector and ⊕ represents the Hamacher sum. The Hamacher sum is calculated as:

$$x \oplus y = \frac{x + y - (2 \cdot x \cdot y)}{1 - (x \cdot y)} \quad (8)$$

where, x and y represent the fuzzy input values in the range of [0,1]. A single task security impact score is calculated as:

$$T_{isi} = T_i < C_h + I_n + A_n + C_s + I_s + A_s > \quad (9)$$

With the task risk calculated as:

$$R_{Ti} = T_{isi} \times sf \quad (10)$$

where, sf is a scaling factor to normalize the calculated risk in the range of 0-10.0 as represented in CVSS. The static task risk threshold $R_{thTi}$ is calculated by, (i) making poi...n=pthoi...n in (7), where pthoi...n is the operation threat thresholds provided by the threat detector during design, and (ii) using (9) and (10) to calculate $R_{thTi}$. The maximum upper bound task risk $R_{Ti(upper\_bound)}$ is calculated by making po1...n=1.0 in (7) and utilizing (10). The operation threat probability being 1.0 represents the maximum likelihood of a possible threat and hence would result in an upper bound task risk threshold. In no case can the risk of a task go beyond $R_{Ti(upper\_bound)}$.

Modes level: the composing tasks' security threat risk thresholds are accumulated in a mode to come up with the initial mode threat risk threshold as:

$$R_{thMi(initial)} = \Sigma_{j=1}^{i} R_{thTj} \quad (11)$$

In order to normalize the mode risk threshold in the standard range of 0-10.0, the following normalization technique is performed:

$$R_{thMi} = \max(R_{thT1..i}) \times \left( \frac{R_{thMi(initial)}}{\max(R_{thMi..n(initial)})} \right) \quad (12)$$

Mode risk threat thresholds are calculated for all the modes of the system. The system risk threat threshold at design time is $R_{thMn}$ where Mode n represents the highest operating mode of the system. The upper bound mode risk $R_{thMn(upper\_bound)}$ for every mode is also calculated using the composing upper bound tasks risk $R_{Ti(upper\_bound)}$ in (12) and (11).

Dynamic Risk Evaluation

A dynamic risk, which is the runtime risk of the system in its current operating mode, is calculated during deployment. The advantage of the FIRE graph is that the propagation equations required for the dynamic risk calculation is the same as the equations used to compute the static mode risk thresholds. This is specifically essential as life-critical systems have limited resources and security risk evaluation in just one consideration in the functioning of the entire system. During deployment poi=ptoi in (7), where ptoi is the runtime threat probability of the operations provided by the threat detector. The dynamic mode risk, $R_{Mi}$ is then calculated and normalized in the range 0-$R_{thMn(upper\_bound)}$ ($R_{thMn(upper\_bound)} \leq 10.0$, represents the maximum attainable risk of the system and n is the highest operating mode), using (11) as follows:

$$R_{Mi} = R_{thMn(upper\_bound)} \times \left( \frac{R_{Mi(initial)}}{\max(R_{Mi..n(initial)})} \right). \quad (13)$$

Insulin Pump Case Study: FIRE Evaluation

Smart-Connected Insulin Pump Model

Figure 23:
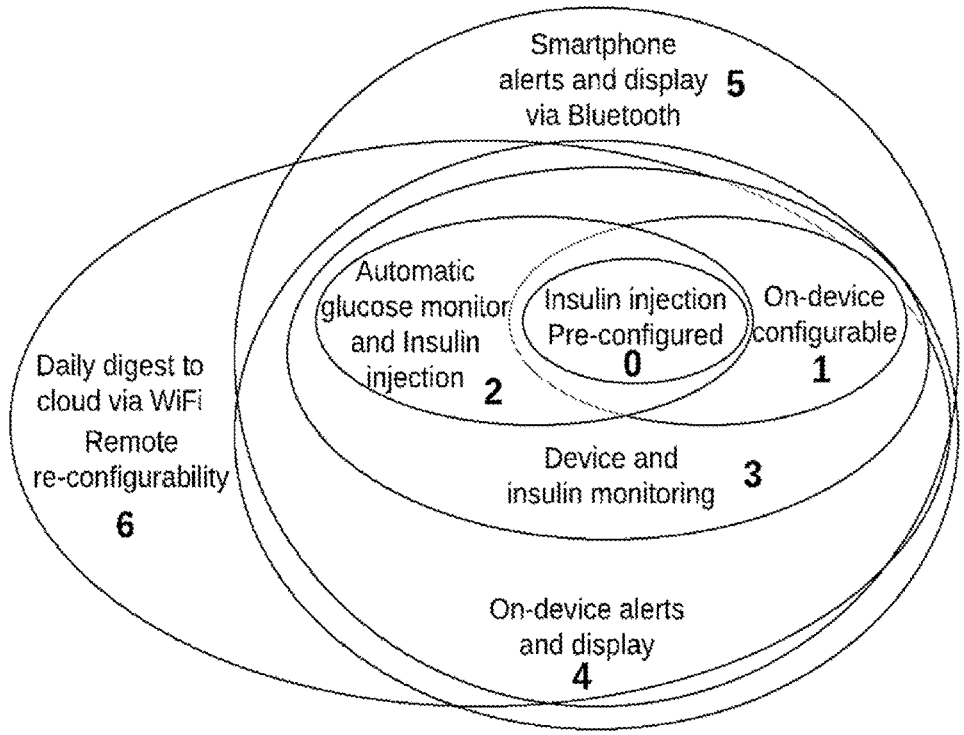
FIG. 23 shows a multi-modal design of a smart-connected insulin in an embodiment of the invention.

The FIRE methodology was evaluated on a smart-connected insulin pump case study. An insulin pump is a life-critical embedded system that monitors the glucose level of a patient and injects a suitable amount of insulin into the bloody stream when needed. The smart-connected insulin pump was modelled based on Medtronic Inc. ("MiniMed 670G Insulin Pump," Available: www.medtronicdiabetes.com/products/minimed-670 g-insulin-pump-system, accessed: Sep. 5, 2019). The insulin pump is initially configured by the physician during implantation based on the patient's history and insulin requirements. If necessary, the patient can manually inject a required dose of insulin using the on-device buttons. The glucose level of the blood stream can either be measured using a manual glucose meter or a continuous glucose monitor (CGM). The device and insulin temperature are monitored via sensors in the pump in order to maintain proper functioning of the pump. The smart-connected features include: (i) connection of the insulin pump to a smartphone via Bluetooth to keep track of the functioning of the pump, sending alerts, and check dosage/glucose levels, and (ii) wireless information transfer via WiFi to the healthcare cloud for remote monitoring and reconfiguring by a physician. With its wireless links and sensitive data, the smart-connected insulin pump provides a wide attack surface that can be exploited for potential life threatening security attacks as demonstrated by Chunxiao et al., (IEEE 13th International Conference on e-Health Networking, Applications and Services, pp. 150-156, 2011). Hence, the multi-modal framework was used to design the insulin pump in order to ensure security. An illustration of such a design paradigm is shown in FIG. 23. The insulin pump has 7 modes {M0, ..., M3, ..., M6}, where M0 represents the essential functionality mode that injects insulin into the patient based on the preconfigured settings set by the physician and M6 represents the full blown functionality enabling all the features. There are a total of 12 tasks {T1, ..., T6, ..., T12} (example: Calculation Thread, Warning Thread, etc.) and 54 operations {o1, ..., o7, ... o15, ..., o54} (example: Read Glucose Sensor, Write Actuator, etc.) in the insulin pump model. FIRE methodology and sensitivity analysis is implemented in Python.

FIRE Methodology for the Insulin Pump

Figure 24:
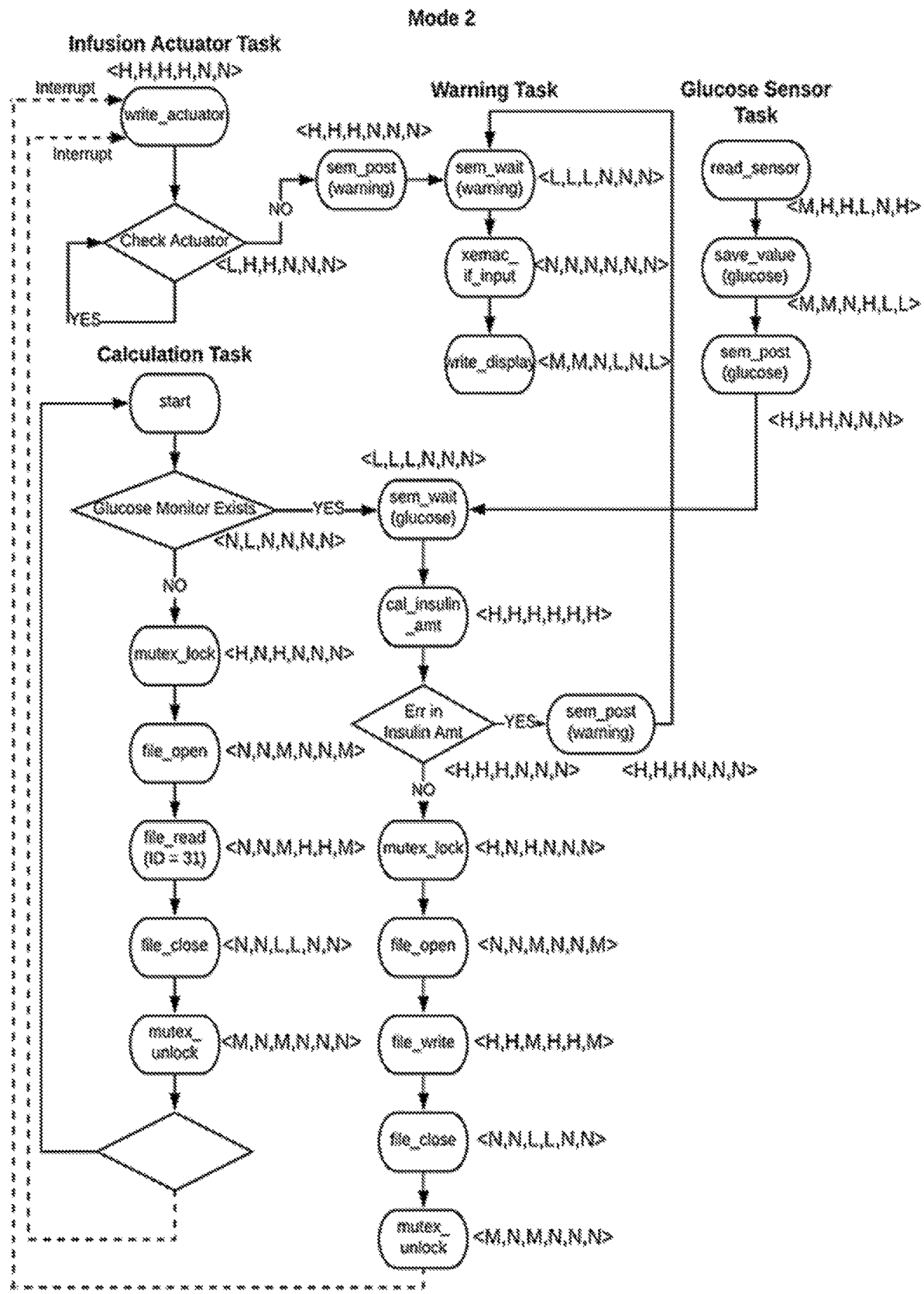
FIG. 24 illustrates a FIRE graph for Mode 2 of the smart-connected insulin pump of FIG. 23.

The FIRE methodology is utilized to calculate the static risk threat thresholds for all the modes of the insulin pump during design time. A sample FIRE graph of Mode 2 of the multi-modal insulin pump is illustrated in FIG. 24. The example of the Glucose Sensor Task in Mode 2 demonstrates the assignment of the CIA values and calculation of the effective task risk. The Glucose Sensor Task has 3 operations—read_glucose_sensor, save_glucose_value and semaphore_post. Each of these operations are assigned CIA values based on their impacts on health and data-sensitivity. read_glucose_sensor is assigned <M,H,H,L,N,H>, save_glucose_value is assigned <M,M,N,H,L,L> and semaphore_post is assigned <H,H,H,N,N,N>. The CIA health values for read_glucose_sensor is <M,H,H> representing a loss of confidentiality of the operation has a reasonable impact on the health of the patient (M), however loss of integrity and availability results in a critical impact on patient health (H). The CIA data-sensitivity values for the same operation are <L,N,H> representing a loss of confidentiality of the glucose sensor data has a low impact (L), but a loss of integrity of the sensor data has no effect (N). The probability threat thresholds of these operations are provided by the threat detector. The CIA values are assigned scores as in Table 6, and the Glucose Sensor Task risk is calculated using (7) and (8) as:

$$T_{Glucose\ Sensor\ Task} = \ <0.31, 0.56, 0.56, 0.22, 0.0, 0.56> \times 0.0 \oplus$$
$$<0.31, 0.31, 0.0, 0.56, 0.22, 0.22> \times 0.0 \oplus$$
$$<0.56, 0.56, 0.56, 0.0, 0.0, 0.0> \times 0.1$$
$$= \ <0.056, 0.056, 0.056, 0, 0, 0>$$

$$T_{Glucose\ Sensor\ Task(si)} = (0.056 + 0.056 + 0.056)$$
$$= 0.168$$

$$R_{TGlucose\ Sensor\ Task} = 0.168 \times 1.6667\ (sf)$$
$$= 0.28$$

The risks of the other tasks in Mode 2 and all the other modes are calculated. Using (10), (11) and (12), the static mode risk threat threshold of Mode 2 is calculated as:

$$R_{thM2} = 5.81 \times \left(\frac{6.466}{16.014}\right) = 2.34$$

Similarly, the risk threat thresholds for all the modes of the insulin pump are determined and range from $R_{thM1}$=1.35 to $R_{thM7}$=5.81. $R_{thM7}$ (upper bound) is calculated with a value of 8.3 and utilized in (13) as the normalization factor for runtime dynamic mode risk calculations.

Sensitivity Analysis of FIRE Methodology

Sensitivity analysis is important for the evaluation of FIRE. Experiments are conducted on the smart-connected insulin pump model to analyze the impact of the number of operations in a mode and the threat probability of each operation on how these factors contribute to the effective mode risk. Thus, this analysis informs us about circumstances under which risk mitigation is needed. The analysis enables us to consider how the proposed system reacts to potential security threats without restricting the analysis to one specific threat. It establishes the points at which a particular mode will classify the behavior of the system as under a security threat that will require a mode switch to safely operate again. The measurable impact of the security threat is quantified by the number of operations and estimated threat probability of the operations.

Simulation Setup: the simulation is performed by varying the number of operations in a given mode from one to the maximum number of operations contained in that mode. For each operation, the threat probability is varied from 0 to 1.0 with a granularity of 0.05. The dynamic risk is then calculated for these set of combinations using (13) with RthMn=RthM7. A random selection of operations is made in the simulations and assume that the considered security threats affect only these set of randomly chosen operations.

Figure 25:
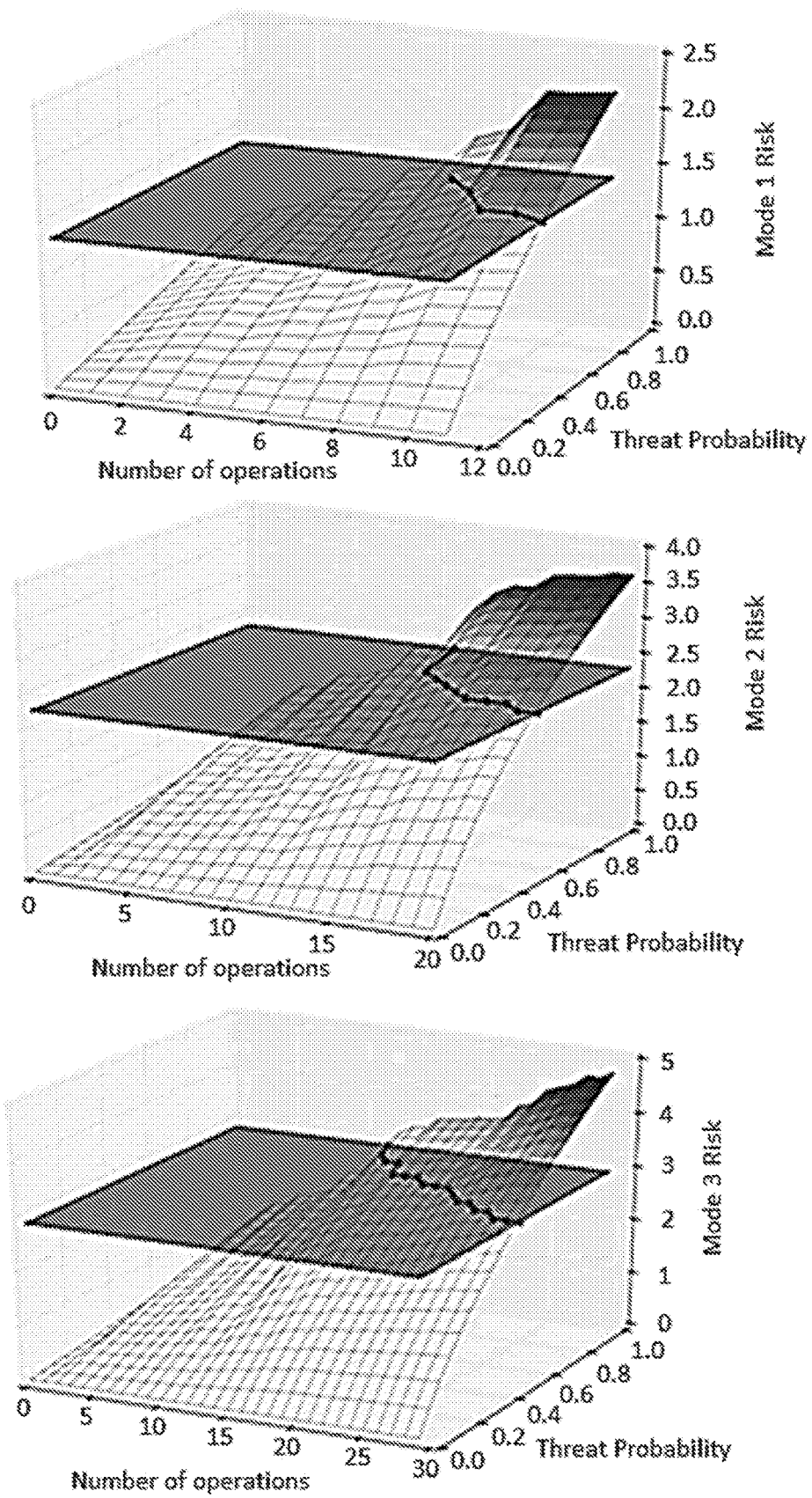
FIG. 25 shows a surface plot of the sensitivity analysis of number of operations v/s threat probability v/s Mode risk—Mode 1, Mode 2 and Mode 3 of the smart connected insulin pump. The heat map surface shows the security threat zone that requires risk mitigation by mode switching.

Sensitivity Analysis: The surface plot of the sensitivity analysis for Mode 1, Mode 2 and Mode 3 of the insulin pump are illustrated in FIG. 25. The highlighted heat map surface area represents the number of operations and the corresponding threat probabilities at which the risk of the mode is beyond its static threat threshold and would require risk management by mode switching. The extreme red region of the heat map shows the worst-case scenario where in all the operations of the mode have been affected by a security threat with the maximum threat probability.

The analysis is discussed in detail for Mode 3. Mode 3 has a total of 30 operations. The number of operations are increased incrementally and the threat probability is varied from 0 to 1.0 for each increment. The heat map surface of Mode 3 in FIG. 25 represents the sensitivity of the mode to security threats by providing a set of points where the dynamic mode risk intersects the static mode risk threshold, beyond which a mode switch decision is needed. Mode 3 is observed to be safe and secure to operate up to 12 operations irrespective of a security threat affecting these operations. The minimum number of operations required to be affected to deem a mode switch decision from Mode 3 is 13, with a threat probability 1.0. On the other hand, the minimum threat probability required to deem a mode switch from Mode 3 is 0.5, where the security threat would need to affect at least 28 operations. The intermediate points (shown in FIG. 26) represents a tradeoff between these extreme conditions.

Figure 26:
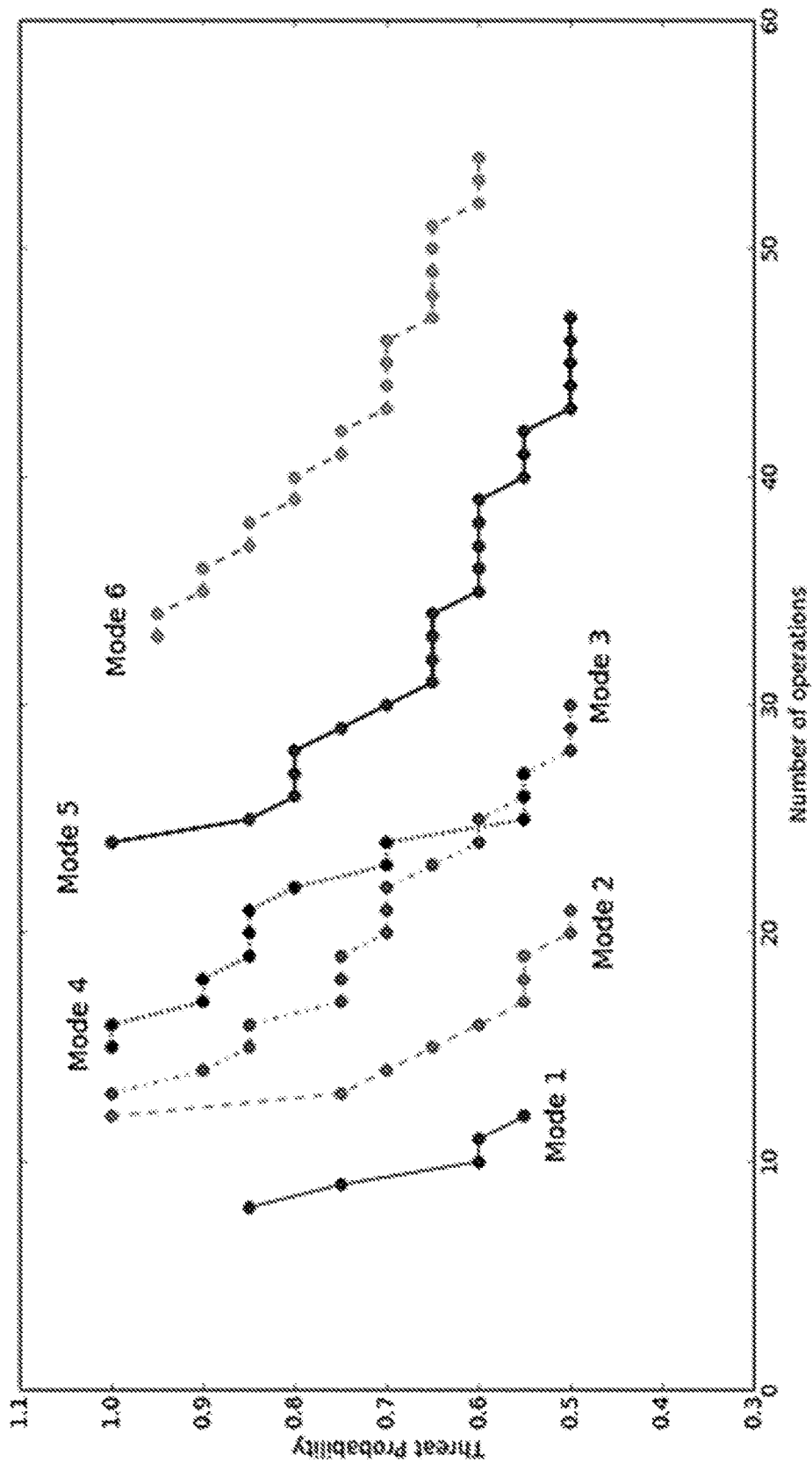
FIG. 26 shows boundary conditions of all the modes of the number of operations v/s threat probability beyond which the insulin pump has been compromised by a security threat.

FIG. 26 showcases the intersection line of the dynamic mode risk with the static mode risk threat threshold for all the modes of the insulin pump. This intersection line represents the lower bound line beyond which there exists a combination of number of operations and corresponding threat probability that would require mitigation by mode switching. It's important to note that this analysis generally shows how the risk assessment and mode switching would react to different types of security threats, but does not evaluate all possible security threat scenarios, as operations to be affected were randomly selected.

Conclusions

Security risk assessment and its continual management is essential in the ever-growing world of connected embedded systems. In particular, this is crucial in life-critical embedded systems where a security threat directly translates to a compromise of patient safety and privacy. Risk evaluation in such systems presents several unique challenges that have to be addressed by all the healthcare stakeholders.

Presented in this example is FIRE—a finely integrated risk evaluation methodology for life-critical embedded systems. FIRE assigns standardized security impact scores to the fundamental operations of the life-critical embedded system by carefully considering health and data-sensitivity. Utilizing the developed FIRE graph, these values are propagated from the ground up to the task and operating mode level. Static risk evaluation methods are finely integrated from the very design with dynamic risk evaluation at runtime for a robust, comprehensive and adaptive risk assessment. This aids in automatic risk mitigation when a security threat is detected. FIRE was demonstrated in a smart-connected insulin pump case study and performed experimental sensitivity analysis that helps establish the circumstances and bounds for risk mitigation by mode switching.

Example 8—Probabilistic Estimation of Threat Intrusion in Embedded Systems for Runtime Detection Due to the increased complexity of embedded systems, designing a system with zero vulnerabilities is infeasible. And, while patches for newly discovered vulnerabilities are being developed and deployed, system remains unprotected in the meantime. Although proactive approaches (e.g., secure communication protocols, static application security testing) are essential, runtime intrusion and malware detection are also needed to detect when attackers can circumvent a system's defenses and gain access to the system. Malware detection can be broadly categorized into signature-based detection and anomaly-based detection. Signature-based detection detects malware by matching execution behaviors, code patterns, etc. to a library of known malware. This requires storing a large library for the growing number of malware and their variants, and is dependent on the update speed of the malware database, limiting their ability to detect zero-day exploits. In contrast, anomaly-based detection creates a model of the normal system behavior and detects malware by looking at deviations from the normal model at runtime. Since any deviation is flagged as malware, anomaly-based detection does not depend on a library of known malware and can provide protection against zero-day attacks. Anomaly-based detection commonly focuses on monitoring the internal sequence of operations within the system, where any deviation from the expected sequence would be considered anomalous. However, sequence-based anomaly detection does not protect against mimicry attacks. Wagner et al. and Kruegel et al. evaluated several sequence-based anomaly detection methods and demonstrated that malware can hide their presence by mimicking the correct execution sequence of the target application/device. This sophisticated type of malware is known as mimicry malware.

Timing-based anomaly detection improves the detection accuracy and resilience to mimicry malware by adding timing information to the normal system model. Time is a critical component in embedded systems and strict timing constraints are often required to ensure system correctness and safety, which could be used to model the system's normal behavior accurately. The resulting time sensitivity means that small changes in the timing of some operations can adversely affect the system execution, in the worst case leading to system failures. By monitoring both the internal timing of operations and the execution sequence, timing-based anomaly detection can detect mimicry attacks by observing the resulting changes in system timing. Several approaches (Zimmer et al.; Yoon et al.; and Lu et al.) use timing of individual operations to detect malware at runtime, but these approaches often suffer from high false positive rates, which is a well-known problem in existing anomaly detectors.

In this example, a statistical approach is presented for modeling the normal system behavior of embedded applications using cumulative distribution functions (CDF) (Katherine L. Monti, "Folded Empirical Distribution Function Curves-Mountain Plots," *The American Statistician*, Vol. 49, No. 4 (November, 1995), pp. 342-345) of timing data within sliding execution windows. Instead of focusing on independent single operations, the normal timing model enables the monitoring of each execution path within a software application. For each path, a probabilistic formulation is used to estimate the presence of malware for individual operations and sequences of operations. To ensure rapid detection, a hardware-based runtime detector is used to analyzes timing samples within a fixed-size sliding window. The detector compares the CDFs of the sliding window against the normal system model and calculates an estimated probability of malware by measuring the percentage of the CDF that falls outside the normal boundaries for each operation and aggregating the results of the operations inside the entire path. The hardware-based malware detector interfaces to the trace port of a processor, without impacting the software execution for runtime detection. To assist system designers in determining which operations to monitor at runtime, a genetic algorithm based optimization method is presented that enable designers to specify optimization goals and constraints to explore tradeoffs between various evaluation metrics. The performance of this optimization approach was evaluated using detection rate, false positive rate, detection latency, area, and energy consumption considering two system prototypes for a smart connected pacemaker and an unmanned aerial vehicle system and considering seven sophisticated mimicry malware.

Assumptions and Threat Model

The goal of CDF-based anomaly detection is to detect sophisticated mimicry malware with minimum false positives given the following assumptions and threat model.

1. The attacker either has access to system software or can simulate the system execution to determine the system's execution sequence, which is needed to create mimicry malware. The attacker can remotely insert the malware into the system utilizing software that exploits a vulnerability, which may be unknown or known but unpatched at the time of insertion. The anomaly-based malware detection presented in this example focuses on detecting malware that has already been inserted in the system and not on detecting the software or system vulnerabilities that lead to the intrusion, both of which are beyond the scope of this example.

2. The target embedded application consists of multiple software tasks (or threads) executing on a single processor core, although it is noted that the detection method presented herein can be applied to other application scenarios including multicore systems.

3. The granularity of detection in this example is at the level of system and function calls, generically called operations. The proposed approach can be applied at coarser or finer granularities following the same design principles.

4. The detection method considers individual execution paths, where a path is defined as a specific sequence of operations within the control flow of each software task.

5. The target malware is mimicry malware, which attempts to evade anomaly detection by mimicking normal execution behavior. Mimicry malware interleaves malicious and normal execution and are sophisticated enough to escape detection from simple sequence-based anomaly detection.

CDF-Anomaly Detection

FIG. 6 presents the design flow of the CDF-based anomaly detection method. The software application is first statically analyzed to determine the operations, oi, and execution paths, pi, within all software tasks. For each operation, the system is executed to collect training data by executing the system under various normal execution scenarios, each for at least 1000 execution of all executions paths. The processors trace interface (Stollon, N, *On-Chip Instrumentation: Design and Debug for Systems on Chip*, Springer US, 2011) was utilized to observe the timing of operations without affecting the execution or timing thereof. The training data is split into two different data sets, training data set 1 is used to create the normal model of the system, and training data set 2 is used to calculate the per-operation threshold.

To construct the per-operation normal system model, the training data set 1 is split into small overlapping segments, called execution windows, and the CDF for each execution window in the training data set 1 is calculated. Instead of storing all the resulting CDFs, which would require prohibitively larger memory requirements, only the most extreme points of the CDFs across all windows are stored, the resulting points are called CDF boundaries.

After determining the CDF boundaries, the training data set 2 is also split into overlapping execution windows, their CDFs are calculated, and compared against the CDF boundaries. Next, the minimum overlap between these CDFs and the CDF boundaries across all execution windows is computed and its complement is set as the threshold for the operation. In the presently described approach, the threshold defines the maximum deviation the CDFs can have from the normal execution while still being considered normal.

The thresholds for all operations within an execution path (e.g., a sequence of operations inside a software task) are analyzed to determine a per-path threshold, which defines a per-path probability beyond which the approach is confident about the presence of malware.

At runtime, timing samples are collected using the same window size and stride utilized to build the normal system model. The CDFs for each operation are calculated, and the percentage of CDF values outside the statically determined CDF boundaries are used to estimate the probability of malware for each operation. For each execution path, the detection method calculates the probability of malware affecting the timing of the path's operations. This estimated probability is compared against the per-path threshold to determine if malware is present in the system.

Per-Event CDF Analysis and Window-Based Boundary Construction

The CDF represents the distribution of timing samples within an execution window. Creating a model of the normal system behavior using CDFs allows one to estimate the percentage of overlap between runtime CDFs and the normal system model's CDFs. Additionally, it reduces the storage requirements compared to other approaches (e.g., KDE estimation, see Emmanuel Parzen, *Ann. Math. Statist.* 33(3), 1962). This approach is based on the Kolmogorov-Smirnov test (K-S test) and seeks to detect anomalies by statistically comparing the distribution of timing data between a normal system execution model and the runtime execution. Without assuming a specific distribution, the K-S test is used to test samples from a referenced distribution for equality, where the referenced distribution is the normal system model. To test if the sample and normal distribution belong to the same population, the K-S test computes the CDF for both distributions, and measures the maximum difference between the two.

While the K-S test can be directly applied to detect anomalous executions, one would need to collect 1000s of timing samples for each operation before testing the distributions. Storing and analyzing the entire execution history for an operation is infeasible and would lead to prohibitively long detection delays. Therefore, the CDF-based anomaly detection collects and analyzes an operation's timing within a fixed execution window that maintains multiple execution timing samples. The window size, defined as the number of timing samples maintained, should be large enough for statistical analysis but small enough to reduce the detection delay. For each window, the stride defines how many new timing samples are collected before executing the CDF analysis again. A smaller stride produces smaller changes in the CDF but requires executing the CDF analysis more frequently, which includes calculating the CDFs of the runtime windows more frequently to detect malware. However, a larger stride would allow malware to execute longer before being detected, which could be fatal for some systems.

FIG. 7 presents a conceptual overview of the window-based CDF calculations showing the resulting CDFs for four different execution windows and the resulting boundaries. In this example, the window size is 20 and the stride is 5. Thus, each CDF involves 20 samples, in which 25% are new timing samples and 75% are prior samples. After the CDFs for all windows of an operation are obtained during the training stage, the boundaries that define the normal system's model can be determined. The bolded lines in FIG. 7 illustrates the CDF bounds for the sample windows. The lower boundary is constructed by points in the CDFs that have the lowest cumulative probability at each timing value, and the upper boundary is constructed by the points that have the highest cumulative probability at each timing sample. These boundaries are configured into the anomaly detector and used at runtime. Instead of fitting the boundary curve to be a high dimensional representation, because a fixed window size is used, the CDF's cumulative probability will be discretized with a step size equal to the inverse of the window size. Thus, the CDF boundaries are stored as two scalar arrays, Boundupper(oi)[ ] and Boundlower(oi)[ ], that contain the timing values corresponding to each discrete cumulative probability step.

Per-Path CDF Analysis and Malware Probability Estimation

For an operation, oi, the estimated probability of malware, Pestoi(M), depends on the percentage of CDF values outside the CDF boundaries defined in the normal system model. FIG. 8 presents an example demonstrating how the probability of malware is calculated. The solid lines are the normal boundaries, and the dashed lines are the CDFs obtained from three different windows of runtime timing data. The crosses CDF is completely outside the CDF boundary, and thus is estimated to have 100% malicious execution. In contrast, the dotted CDF is completely within the CDF boundaries and thus is estimated to have 0% malicious execution. For a CDF that partially overlaps with the CDF boundary, the probability of malware is estimated as the percentage of points within the CDF that fall outside the boundaries. For example, the triangles CDF has a probability of malware Pestoi(M)=1−(0.65−0.20)=0.55, which indicates there is estimated to be a 55% probability the execution is malicious. In practice, with the Boundupper (oi)[ ] and Boundlower(oi)[ ] arrays, the Pestoi(M) is calculated by determining the number of samples that fall outside these bounds. For example, if 19 of 20 timing values in a window are outside the CDF boundary, the estimated probability of malware Pestoi(M)=0.95.

Individual operations are considered malicious if the estimated probability of malware, Pestoi(M) is greater than a predefined threshold. Instead of deciding based on a single operation, which may yield high false positive rates, a more robust decision is made by considering the Pestoi(M) for multiple operations in an execution path. An execution path is a sequence of operations within a software task. The probability of malware execution in a path would be higher if the probability of more operations within the path are estimated to be malicious. Assuming independence of execution time between two operations, the probability of malware for a path pj is:

$$P_{estPj}(M)=1-\Pi_{i=0}^{n}(1-P_{est}o_i(M)) \quad (1).$$

FIG. 9 presents two different example execution paths for the smart connected pacemaker application considered in this example. For execution scenario a), four operations are monitored and the estimated probability of malware for path is calculated as: Pestpi(M)=1−(1−0.07)(1−0.08)(1−0.10)(1−

0.08)=0.2915. This indicates this execution path for the current execution window has 29.15% probability of being malicious. Execution path b) represents a different execution path in the same task, in which nine operations are monitored. The estimated probability of malware for this alternative path is: Pestpj(M)=1−(1−0.00)(1−0.01)(1−0.00)(1−0.01) (1−0.03)(1−0.00)(1−0.02)(1−0.00)(1−0.00)=0.0683, which indicates this execution path has 6.83% probability of being malicious.

Whether malware is affecting the system execution is decided per execution path, by comparing the path's estimated probability of malware to a path specific threshold. Due to potential limitations of design-time training, some normal system executions may deviate from the CDF boundaries. Without accounting for these deviations, a high false positive rate would be expected. The threshold is defined by the maximum probability of malware execution $P_{maxoi(M)}$ per operation, and is calculated by processing the training data set 2 utilizing the same approach as above. The threshold for path pj is $$Tp_j = 1 - \Pi_{i=0}^n (1 - P_{max}o_i(M)) \quad (2).$$

The path-based threshold is utilized to minimize that false positive rate. Equation 2 utilizes the minimum overlap found in the training data set 2 (normal data only), while Equation 1 is utilized at runtime to obtain the estimated probability of malware for the entire path. For example, assume the minimum overlap throughout all windows of operation of for the second testing dataset is 0.90. This means that the highest estimated probability of malware for normal system execution is 0.10, which in turns means that a runtime estimated probability of malware greater than 0.10 will be reported as malware. If five operations within that path are monitored, and each has the same minimum probability, the path threshold Tpj=1−(1−0.10)5=0.40951. This approach strives to ensure the CDF-based anomaly detection is accurate with minimal false positives. It can also be observed that as the number of monitored operations increases, the threshold decreases, but the strictness of the approach remains.

Runtime Detection

At runtime, the threshold of each path and normal CDF boundaries are configured within the hardware-based malware detector. The malware detector collects timing samples of each operation by analyzing the signals from the processor trace port. Whenever the stride is reached for an operation's window, the detector calculates the CDF and Pestoi (M) for the operation. When the CDFs of all monitored operations within a path j are calculated, the anomaly detector calculates Pestpj(M) and compares that estimated probability with the threshold Tpj. If Pest pj(M)>Tpj, the detector asserts a non-maskable interrupt indicating the presence of malware.

Detection latency is a critical indicator of the detection performance and is defined as the time between the moment when malware begins to execute and the moment the detector detects the anomalous execution and asserts the alert. For the CDF-based anomaly detection, the detection latency is primarily due to the window size and stride. FIG. 10 presents a demonstration of how the sliding window approach affects detection latency. As the malware begins to execute, the estimated probability of malware increases. With each stride, the sliding window contains more timing samples from the malware, increasing the estimated probability of malware. Once the estimated probability of malware exceeds the threshold, the detector asserts the presence of malware.

CDF-Based Anomaly Detection Hardware

Figure 27:
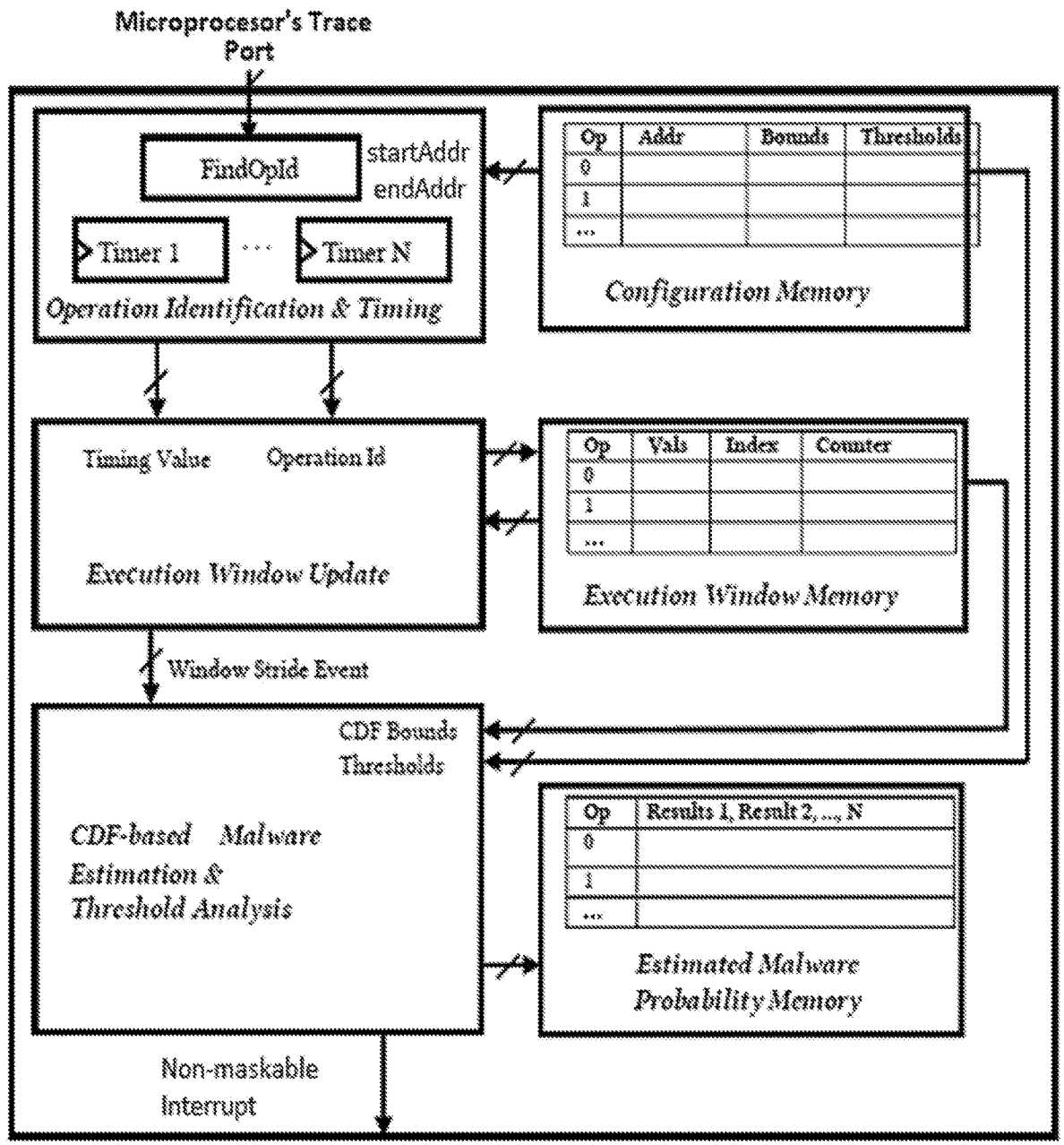
FIG. 27 illustrates a CDF-based anomaly detection hardware architecture in an embodiment of the present invention.

FIG. 27 presents an overview of the CDF-based anomaly detection (CDFAD) hardware. The CDFAD consists of three main components, the Operation Identification & Timing, Execution Window Update, and Malware Estimation & Threshold Analysis components. Additionally, the CDFAD uses three local memories to store operations' configuration, execution windows, and estimated malware probabilities, respectively. The Configuration Memory stores the monitored operations' start and end addresses, CDF boundaries, and thresholds. The Execution Window Memory stores the measured timing samples for the current execution window for all operations, as well as the number of new timing samples measured in the current stride. The Malware Estimation & Threshold Analysis Memory stores the current estimate of the probability of malware for all operations.

The Operation Identification & Timing component directly interfaces with the microprocessors' trace port to detect the execution of the monitored operations, using the operation's Program Counter (PC) addresses. When the start address of an operation is detected, an internal timer is started to measure the execution for the current operation execution. That timer is stopped when the operation's end address is detected. The Execution Window Update component receives the current measured timing value and operation ID from the Operation Identification & Timing and updates the corresponding entry within the Execution Window Memory. If the stride is reached, a window stride event signal is asserted to signal the Malware Estimation & Threshold Analysis component to perform the CDF-based analysis for this operation. The Malware Estimation & Threshold Analysis component reads the current execution window from the Execution Window Memory, and reads the CDF boundaries and threshold from the Configuration Memory, then calculates the Pestoi(M) of the current execution window and store the results in the Estimated Malware Probability Memory component. If Pestoi(M) is greater than the threshold, the CDFAD asserts the non-maskable interrupt.

The CDFAD hardware was fabricated for an Artix-7 XC7A200T FPGA with Vivado 2016.4. The synthetized hardware support 32 operations, using 32-bit registers for both the operation's addresses and timers, and using block RAMs (BRAMs) to implement the local memories. The CDFAD hardware requires 6,481 lookup tables (LUTs), 7,666 flip-flops (FF), and three BRAMs (2×32 Kb, 1×64 Kb). No additional external memory or storage is needed. The CDFAD hardware has a maximum operating frequency of 128 MHz, which is sufficient for the target integration with a 100 MHz MicroBlaze based system. The CDFAD hardware has a peak power consumption of 66 mW and average power consumption of 41.9 mW, which corresponds to a power overhead of only 3.56%. Only the event detection and timing components need to operate at the processor frequency, and using a dual clock configuration could enable lower energy consumption.

Automatic Optimization of Operation Selection

For highly complex systems, monitoring every operation inside the target system is infeasible, due to either hardware limitations or energy/area constraints. Randomly selecting the operations to be monitored cannot secure all software tasks inside the system or meet all system constraints (i.e. remain below a 5% energy overhead). Therefore, an optimization methodology and tool was developed to assist designers in selecting which operations to monitor in order to achieve the best results under various constraints.

Candidate underlying optimization algorithms include hill climbing, simulated annealing, genetic algorithm, etc., all of which have been proved to be able to reach near optimal configurations. Of these optimization algorithms, a genetic algorithm (GA) was utilized for the optimization tool as it lends itself well to representing the selection of which operations to monitor. Genetic algorithm utilize a selection method analogous to natural selection, in which "survival of the fittest" takes place (Friedberg, R. M., A learning machine: Part I, *IBM Journal of Research and Development*, 2, 2-13, 1958; and Friedberg, R. M., A learning machine: Part II, *IBM Journal of Research and Development*, 3(3), 282-287, 1959). GAs are known for performing well when solving big combinatorial problems.

Genetic algorithms start by initializing a set of k randomly generated states, called the initial population. Each individual in the population is represented as a string, usually called chromosome, over a finite alphabet, in which each digit is called a gene. For the problem of optimizing the selection of which events to monitoring at runtime, each individual is encoded as:

$$\langle O1,S1,W1 \rangle, \langle O2,S2,W2 \rangle, \ldots, \langle On,Sn,Wn \rangle \quad (14)$$

where $O_i$ is a binary value indicating if operation i is monitored, and $W_i$ and $S_i$ are the window size and stride, respectively, for monitoring that operation.

During each GA iteration (commonly called a generation), new offspring configurations will be produced using genetic crossovers and mutations. For each generation, the total population size should remain the same. To ensure the best configurations seen so far survive, the m best individuals in the current generation will be copied to the next generation, an approach know as elitism (S. Baluja and R. Caruana, "Removing the Genetics from the Standard Genetic Algorithm," Technical Report. Carnegie Mellon Univ., Pittsburgh, PA, USA, 1995). The remaining individuals will be created by performing a crossover between two parent, in which a single split between the chromosomes is made. The selection of the parents that will produce a new child is based on their individual fitness. Each individual is rated by a fitness function that returns higher values for more promising individuals, where a higher fitness value results in a higher chance of being selected for reproduction. Each offspring generated is validated after being created to verify that the offspring represents a feasible solution to the problem. Finally, each gene has a small independent probability of mutating when the crossover is happening. After several generations, the population tend to converge toward the optimal solution.

For the optimization of choosing which operations to be monitored by the CDF-based anomaly detection, the GA was configured to use a population size of 100, 300 generations, and a mutation rate of 0.05. Both the constraints and fitness functions are configurable by the system designers, thereby enabling the tuning of the optimization to meet each system's unique requirements. Table 7 presents an overview of the various metrics that can either be used to define constraints or be used within the fitness function for evaluating configurations. The validation function discards individuals that does not comply with the constraints for the CDF-based anomaly detector in the present scenarios.

TABLE 7

Description of the metrics and constraints.

| | | |
|---|---|---|
| Area Overhead | A | Area increase by the CDFAD component compared to the base system. |
| Energy Overhead | E | Energy increase by the CDFAD component compared to the base system. |
| Average System False Positive Rate | $FPR_{System}$ | Average false positive rate across all operations in the system. |
| Average Path False Positive Rate | $FPR_{Path}$ | Average false positive rate of operations in a specific path. |
| System-level Operation Coverage | $Coverage_{System}$ | Percentage of operations monitored across all paths. |
| Average Path-based Operation Coverage | $Coverage_{Path}$ | Average coverage in percentage across all paths inside the target system. Path coverage is defined as percentage of events monitored in each path. |
| Monitored operations | M | Number of currently monitored operations. |
| Monitored operations per path | $M_{Path\ i}$ | Amount of operations currently being monitored in path i. |
| Maximum number of operations supported in hardware | $M_{Max}$ | Maximum number of operations that can be monitored (user defined). |
| Window Size | W | Number of timing samples stored at any given time. |
| Stride Size | S | Number of new timing samples needed before running the CDF analysis again. |

Experimental Setup

Benchmarks

Two benchmarks were developed for the purpose of validating the proposed threat detection system. These benchmarks are prototypes of a smart connected pacemaker and an unmanned aerial vehicle (UAV), which are representative of complex embedded systems that monitor, analyze, store, and transmit data. Both benchmarks were completely implemented using the Artix-7-XC7A200T FPGA. For both systems, the CDFAD hardware is integrated with the system using the MicroBlaze processor's trace interface (Xilinx, Inc., MicroBlaze Processor Reference Guide, UG9854, 2016), thereby non-intrusively observe and analyze the system execution at runtime to detect anomalies.

Unmanned Aerial Vehicle

Figure 28:
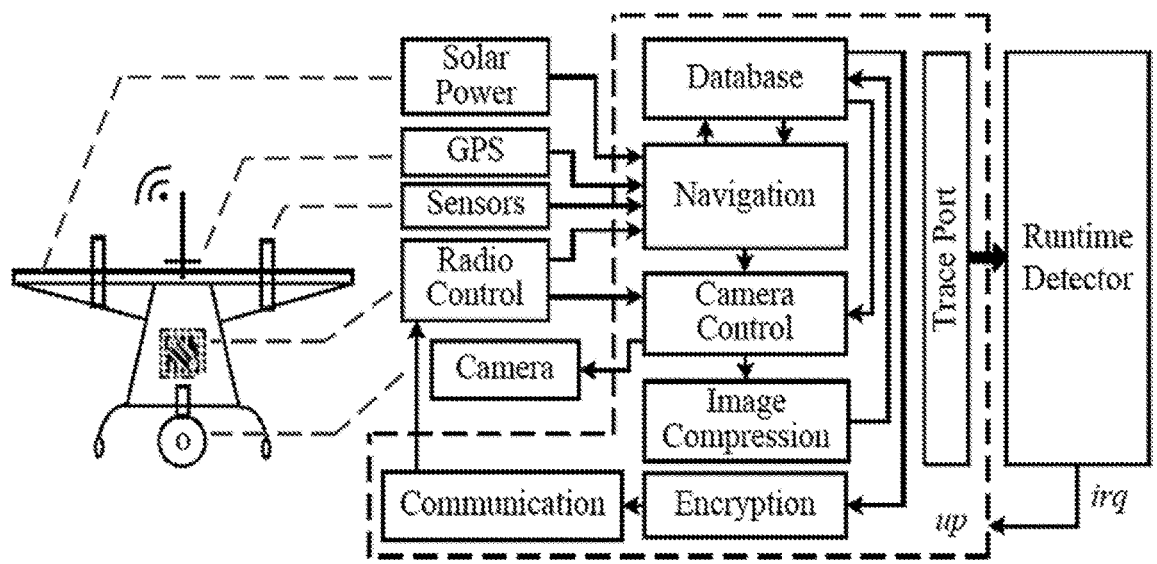
FIG. 28 shows an overview of an embedded system hardware architecture for a benchmark for an unmanned aerial vehicle (UAV) (panel a), and a high-level overview of the software tasks (panel b) in an embodiment of the present invention.
Figure 28:
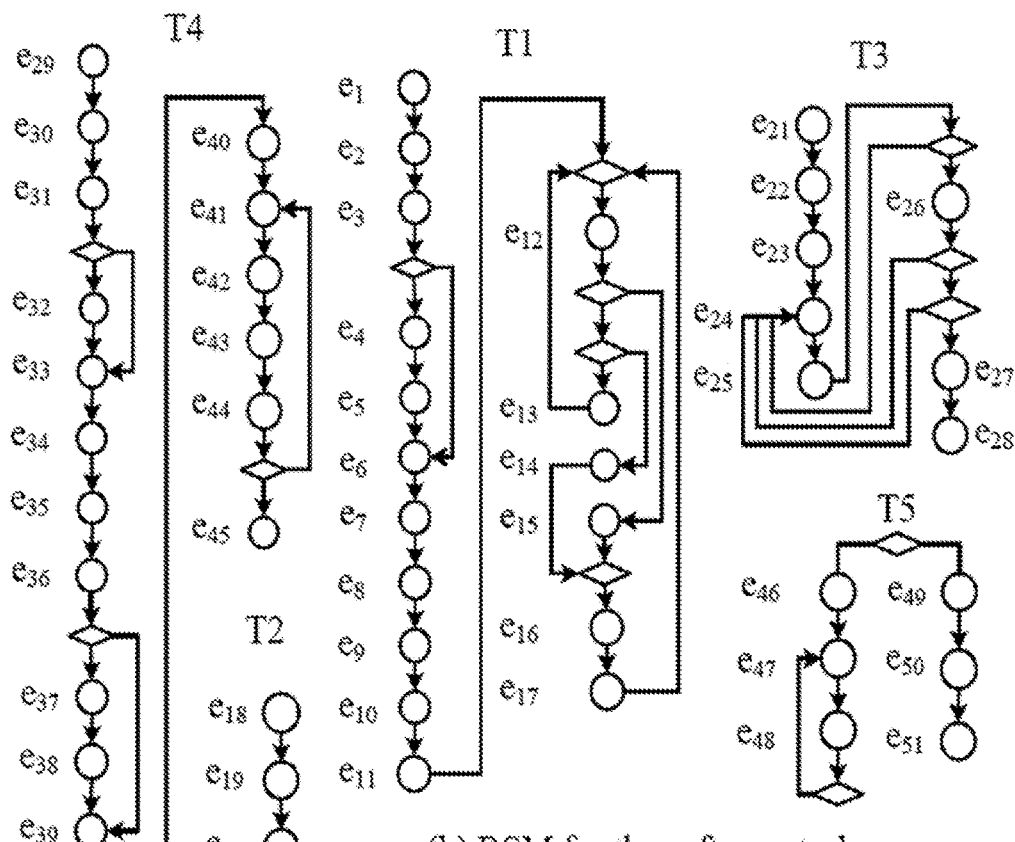

The UAV is a representative example of a widely-used network-connected embedded system utilized in a wide variety of applications (e.g., border security, geographical monitoring, photography). FIG. 28, panel a, shows a high-level overview of the UAV benchmark (Cai et al., *Unmanned Systems*, 2, 2014). The hardware includes a solar power module, GPS, radio control module, camera, and several sensors including magnetometers, air speed meter, altimeter, etc. The benchmark is comprised of five software tasks used for navigation, camera control, image compression, database access, and communications. FIG. 28, panel b, presents an overview of the control flow graph of the UAV benchmark. The navigation module (T1) receives signals from the GPS and sensors and navigates the UAV along a preset route using the PID algorithm (Monti, 1995). The images taken (T2) by the UAV are compressed with JPEG compression (T3), stored in the database, and transmitted to a ground station with AES256 encryption (T4) using a TCP communication protocol (T5). A pilot can take control of the UAV's navigation at any time and control the onboard camera using the communication link.

Smart Connected Pacemaker

Figure 29:
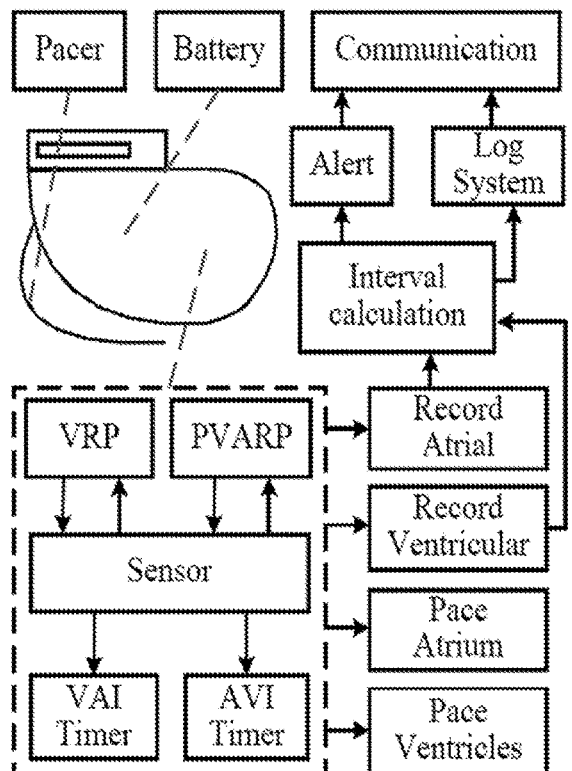
FIG. 29 shows an overview of an embedded system hardware architecture for a benchmark for a smart connected pacemaker (panel a), and a high-level overview of the software tasks (panel b) in an embodiment of the present invention.
Figure 29:
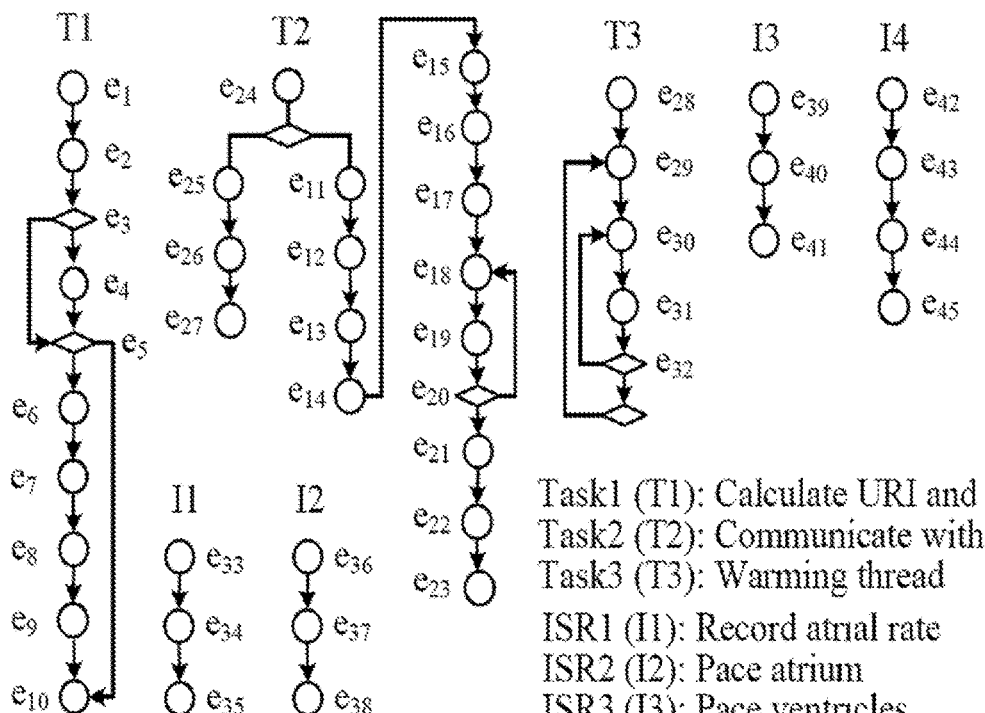

The pacemaker, shown in FIG. 29, includes a simulated patient heart, a tremor sensor, an impulse pacer, and four timers. The simulated patient heart generates irregular beats and reacts to the impulse pacer signal controlled by the pacemaker's software executing on the processor. The cardiac activity sensor interfaces to the simulated heart model and sends the measured heart activity to the microprocessor using interrupts. The output from the cardiac activity sensor also controls the Atrio-Ventricular Interval (AVI) timer and Ventriculo-Atrial Interval (VAI) timer. These timers are used to maintain the appropriate delay between the atrial/ventricular activation and the ventricular/atrial activation, and will generate an interrupt if the AVI/VAI exceeds a specific interval configured by the physician. The PVARP/VRP timers filter noise in the ventricular and atrial channels, respectively (Jiang, et al., *Conf. on Tools and Algorithms for the Construction and Analysis of Systems*, pp. 188-203, 2012; and Singh, et al., "The Cardiac Pacemaker Case Study and its Implementation in Safety-Critical Java and Ravenscar Ada," *Workshop on Java Technologies for Real-time and Embedded Systems*, 2012).

The pacemaker's software, which executes on a MicroBlaze processor, consists of three software tasks and four interrupt service routines (ISRs). The ISRs interact with the pacemaker's cardiac activity sensor and timers, and have the highest priority. ISR operations include performing the atrial and ventricular pacing and recording ventricular and atrial activity. The first software task calculates the Upper Rate Interval (URI) and records cardiac activity to a daily log file. A second software task analyzes the cardiac activity and detects a high URI, which indicates the pacemaker cannot pace the heart correctly or that pacemaker's cardiac activity sensor has malfunctioned. In the operation of a high URI, the pacemaker immediate transmits a warning message to alert the physician. The third software task is responsible for communication, by which the physician can configure the pacemaker's settings, or a home monitoring device can access daily logs of the cardiac activity.

Optimization Scenarios

Four optimization scenarios were analyzed with the purpose of illustrating different optimization tradeoffs that a system designer may encounter at design time. Each scenario results in a different set of constraints and fitness function utilized by the genetic algorithm. When not specifically part of the optimization goal, a set of default constraints were assumed: A<5%, E<5%, $FPR_{System}$<5%, and $M_{Path\ i}$≥2. These values were selected based on the tolerance believed to be acceptable, combined with the requirement for the CDF path-based analysis of having a minimum of two monitored operations per path. The area and energy of the base system were measured from the hardware implementation of the system on the FPGA. The general formulation for fitness function, shown in Equation 4, returns the fitness of a chromosome (C) and is calculated as the sum of the products between the metrics (Metrici) currently being optimized in the scenario and their assigned weights (wi).

$$\text{Fitness } C = w_i ric_i C \tag{15}$$

Subject to constraints {c}
  A≤5%
  E≤5%
  FPRSystem≤5%
  M≤MMax, where MMax is set by the user, and is set to the total number of operations for the Pacemaker and UAV scenarios respectively.
  MPath i≥2, where 2 is the minimum required operations to carry out the analysis.
  W and S are set per path, all operations must have the same values, and the range is set by the user. For the present scenario, the range was between 20 and 200 for the window size, and between 5 and 200 for the stride.

In the scenarios where a fitness function is being maximized, Metrici is equal to the variable (mi) (i.e., maximize coverage):

$$\text{Maximize Metric}_i : m \tag{16}$$

e.g., Metric: $\text{Coverage}_{Path}$.

In the scenarios where a fitness function is being minimized, Metric, is equal to $(1-m_i)$ (i.e., minimize area overhead):

$$\text{Minimize Metric}:(1-m) \tag{17}$$

e.g., Metric: (1-A)

Scenario 1: Minimize the system false positive rate and area overhead. Scenario 1's goal is to select the optimal operations to monitor, while minimizing both the area overhead and overall system false positive rate. The result of this scenario is a small amount of operations monitored, for which both the false positive rate, and the detection rate is reported. The fitness function and constraints for Scenario 1 are defined as:

$$\text{Fitness } C = w_{FPR}(1-FPR_{System}) + w_A(1-A) \tag{18}$$

where the weights $w_{FPR}$ and $w_A$ can be controlled by the system designers to explore tradeoffs between minimizing the two often competing metrics.

Scenario 2: Minimize the energy overhead, maximize the average path coverage percentage. The goal of Scenario 2 is to minimize the energy overhead of the CDF analysis, while maximizing the average path coverage percentage. This scenario effectively searches for the Pareto-optimal points between increasing the coverage and diminishing the energy overhead of monitoring operations. This results in a varying number of operations monitored, which depends on the weights of the fitness function.

$$\text{Fitness } C = w_E(1-E) + w_{Path}(\text{CoveragePath}) \tag{19}$$

Scenario 3: Minimize the system false positive rate, maximize the average system coverage percentage. Scenario 3 represents the situations where a system designer wants to find the Pareto-optimal point between minimizing the average system-level false positive rate and maximizing the average system-level coverage percentage. Similar to Scenario 2, this produces a varying number of monitored probes that depends on the weights assigned in the fitness function. However, the clear distinction would be that the operations selected are not distributed evenly across the different paths, and because of this, an extra degree of freedom is permitted in this scenario.

$$\text{Fitness}(C) = w_{FPR}(1-FPR_{System}) + w_{System}(\text{Coverage}_{System}). \quad (20)$$

Scenario 4: Minimize the area overhead, maximize the average path coverage percentage. Finally, Scenario 4 seeks to minimize the area overhead of the CDF analysis, while maximizing the average path coverage. This scenario produces a similar result to Scenario 2, due to the inherent relationship that exist between area overhead and energy overhead.

$$\text{Fitness } (C) = w_A(1-A) + w_{Path}(\text{Coverage}_{Path}) \quad (21)$$

Malware

To evaluate the CDF-based anomaly detection method, seven mimicry malware were considered based on known malware for specific applications (Sametinger et al., *Communication of ACM*, 58(4), pp. 74-82, 2015; Wasicek et al., *Design Automation Conference*, pp. 2014; Hartmann et al., *Conference on Cyber Conflict (cycon)*, 2013; Kim et al., The American Institute of Aeronautics and Astronautics: Reston, VA, USA, 2012; and Sun et al., 8th *Pacific Rim Conference on Multimedia*, Hong Kong, China, Proceedings, pp: 367-375, 2007). These malware were implemented by interleaving malicious operations with mimicked normal operations that follow the normal execution sequences and execution paths. The primary threat is malWare affecting legitimate executables, specifically mimicry malware, which assume an attacker knows which operations are monitored. As the approach detects deviations in execution sequences and timing, it can also indirectly detect other types of malware, although that is not considered in this example.

1. Information Leakage: The Information Leakage malware reads the patient's cardiac activity log and transmits the data to a third-party server, breaking the confidentiality the data should have. This malware has an impact in the Warning software task from the pacemaker benchmark.

2. Data Manipulation: The Data Manipulation malware manipulates the encryption process to fail the decryption on the receiving side. This malware has an impact in the AES Encryption software task from the UAV benchmark.

3. Fuzz Malware: The Fuzz malware is used to interfere with the system's predefined functionality by slightly changing (i.e., fuzzing) data. Fuzz malware can be implemented in various levels, which enables the evaluation of the effectiveness of malware detection for different fuzzification levels. This malware has an impact in the Calculation and Communication software tasks from the pacemaker benchmark.

4. Gain Scheduling: The Gain Scheduling malware manipulates the gains of control logic and varies scheduling variables to cause system instability. This malware has an impact in the Navigation software task from the UAV benchmark.

5. Camera Obfuscation: The Camera Obfuscation malware manipulates the camera's configuration to increase or disable the flash, such that the image take is unusable due to under/over exposure. This malware has an impact in the Camera Control software task from the UAV benchmark.

6. Key Leakage: The Key Leakage malware steals encryption keys and transmits the keys to an unauthorized third-party server using the communication link. This malware has an impact in the Navigation and Communication software tasks from the UAV benchmark.

7. Image Fuzz: The Image Fuzz malware adds random noise into image pixels during the compression process to make the image unreadable on the user side. This malware has an impact in the Image Compression software task from the UAV benchmark.

Experimental Results

Detection Rate and False Positive Rate

The detection and the false positive rates of the CDF-based anomaly detection are evaluated by seven malware. The true positive rate (TPR) is calculated as the number of malware executions classified as malware, divided by the total number of malware executions.

$$TPR = \frac{\text{Malware executions classified as malware}}{\text{Total malware executions}} \quad (3)$$

Using a separate set of data, the false positive rate (FPR) is calculated as the number of normal executions classified as malware divided by the total number of normal executions.

$$FPR = \frac{\text{Normal executions classified as malware}}{\text{Total normal executions}} \quad (4)$$

In the analysis, the impact of each of the optimization criteria in the fitness function was analyzed by varying the weights from 0 to 100 for each of the two metrics, in small steps, such that the sum of the two weights always equals 100. This allows for the analysis of the tradeoffs involved between the different metrics used in each scenario. Although all four scenarios were analyzed with different weights for both benchmarks, only Scenario 1 is discussed in detail and provide the overall results for the other three scenarios.

Design Analysis and Tradeoffs

For the analysis, 100 trials of the GA were executed for each configuration of metric weights, selected the configuration with the best fitness, and then tested that configuration using one dataset containing both malware execution data to determine the TPR and a set of normal execution data not included in the training data set to evaluate the FPR.

Figure 30:
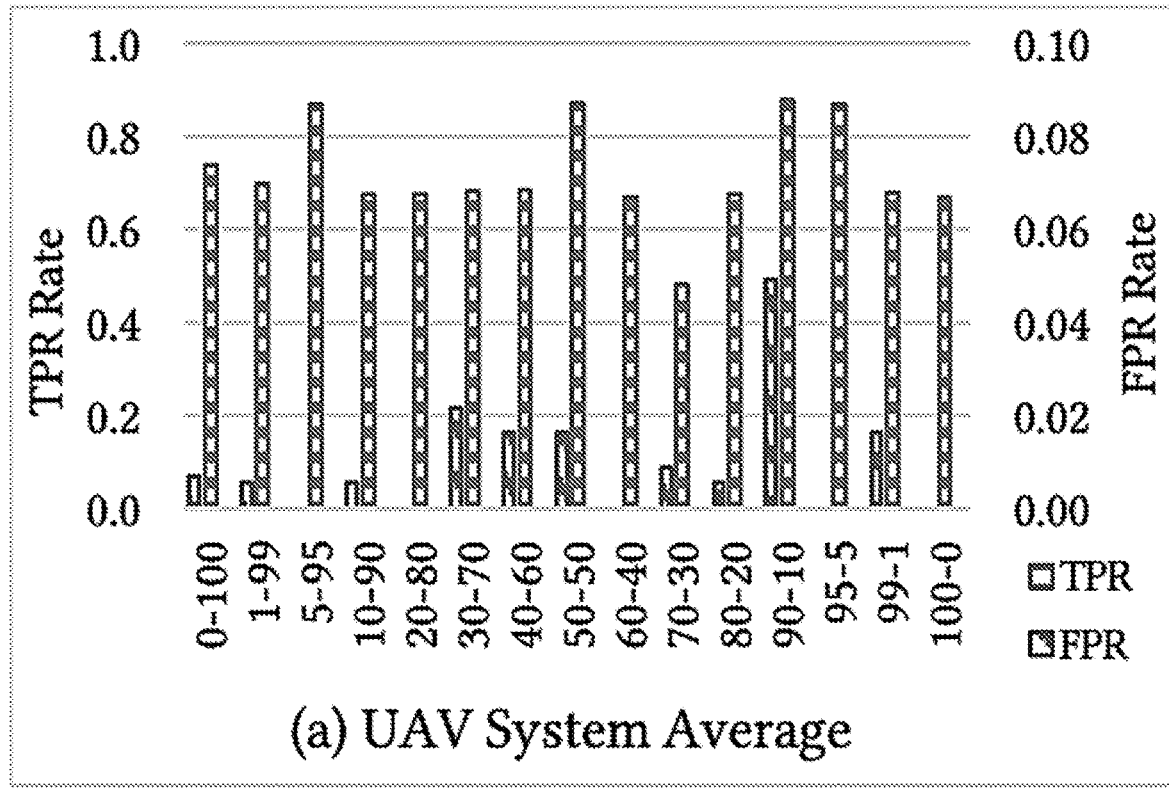
FIG. 30 shows the average FPR and TPR for the UAV benchmark (panel a), while panel b shows the average FPR and TPR for the pacemaker benchmark. The X-axis represent the rate, and the Y-axis represent the results for the different weights of the fitness function. The weights represent the area overhead area overhead $w_A$ and the system false positive rate $w_{FPR}$, and are annotated as $w_A$-$w_{FPR}$.
Figure 30:
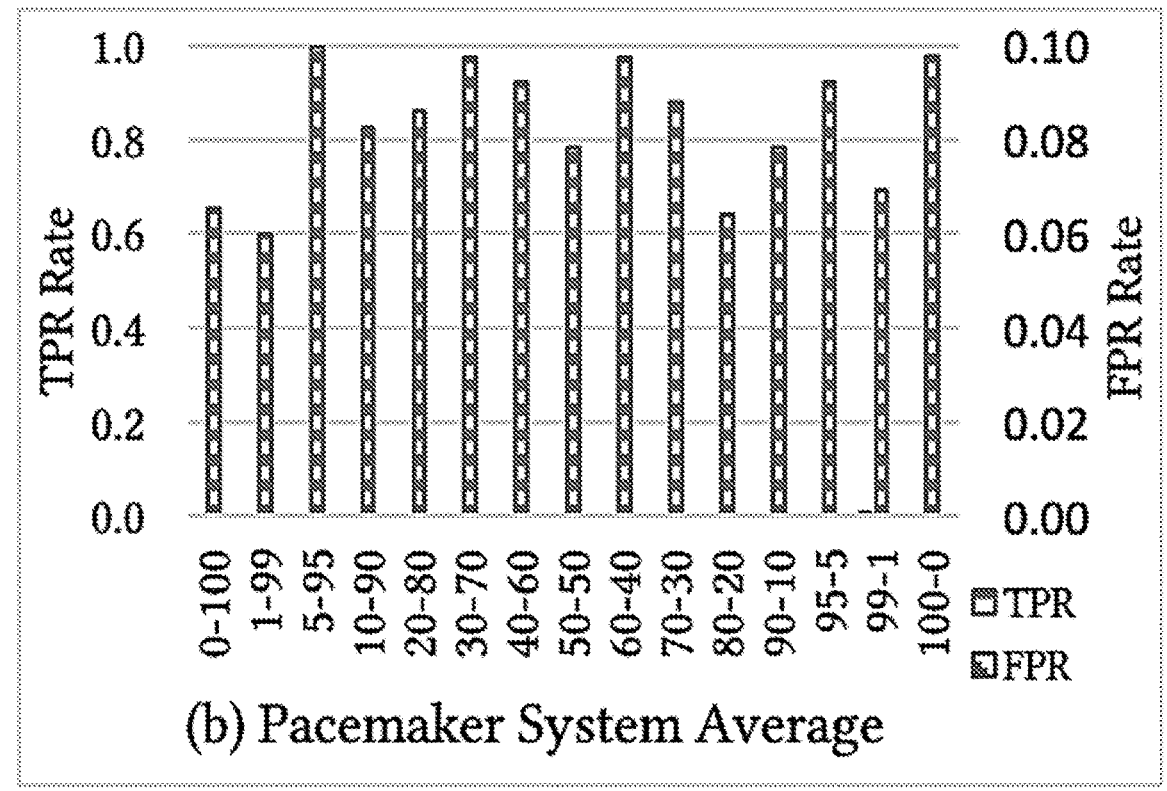

Scenario 1 minimizes both the area overhead and system false positive rate. The analysis is carried out by executing 100 trials of the GA per different weight combination for the area overhead $w_A$ and the system false positive rate $w_{FPR}$, in which the sum of both weights is always equal to 100. The weights increased/decreased in small steps, with $w_A$ starting at 0, and $w_{FPR}$ starting at 100. FIG. 30 shows the average FPR and TPR for scenario 1 for both benchmarks, in which the X-axis represent the weights for $w_A$ and $w_{FPR}$, and the Y-axis represent the FPR and TPR rate.

For the UAV benchmark, FIG. 30, panel a, the scenario has an overall average detection rate of 0.72, with an average 0.01 false positive rate across all weights. The best tradeoff between the different weights is that of $w_A=5$ and $w_{FPR}=95$, which yields a 0.87 TPR and 0.00 FPR. The highest detection rate achieved had weights of $w_A=90$ and $w_{FPR}=10$. While this configuration yields an average detection rate of 0.88 with an average false positive rate of 0.049, which is a small increase in the TPR at the cost of a large increase in the FPR. On the other hand, the lowest detection rate achieved had weight of $w_A=70$, and $w_{FPR}=30$, which yields an average detection rate of just 0.482, with an average false positive rate of 0.009.

The Pacemaker benchmark, FIG. 30, panel b, has an overall average detection rate of 0.83, and a false positive rate of 0.00005 across all weights. The best tradeoff between the different weights is that of $w_A=5$, and $w_{FPR}=95$, which yields a 0.996 TPR and 0.00 FPR, which is also the highest TPR achieved across all weights. On the other hand, the lowest detection rate achieved had weight of $w_A=1$, and $w_{FPR}=99$, which yields an average detection rate of 0.598, with a false positive rate of 0.00.

Figure 31:
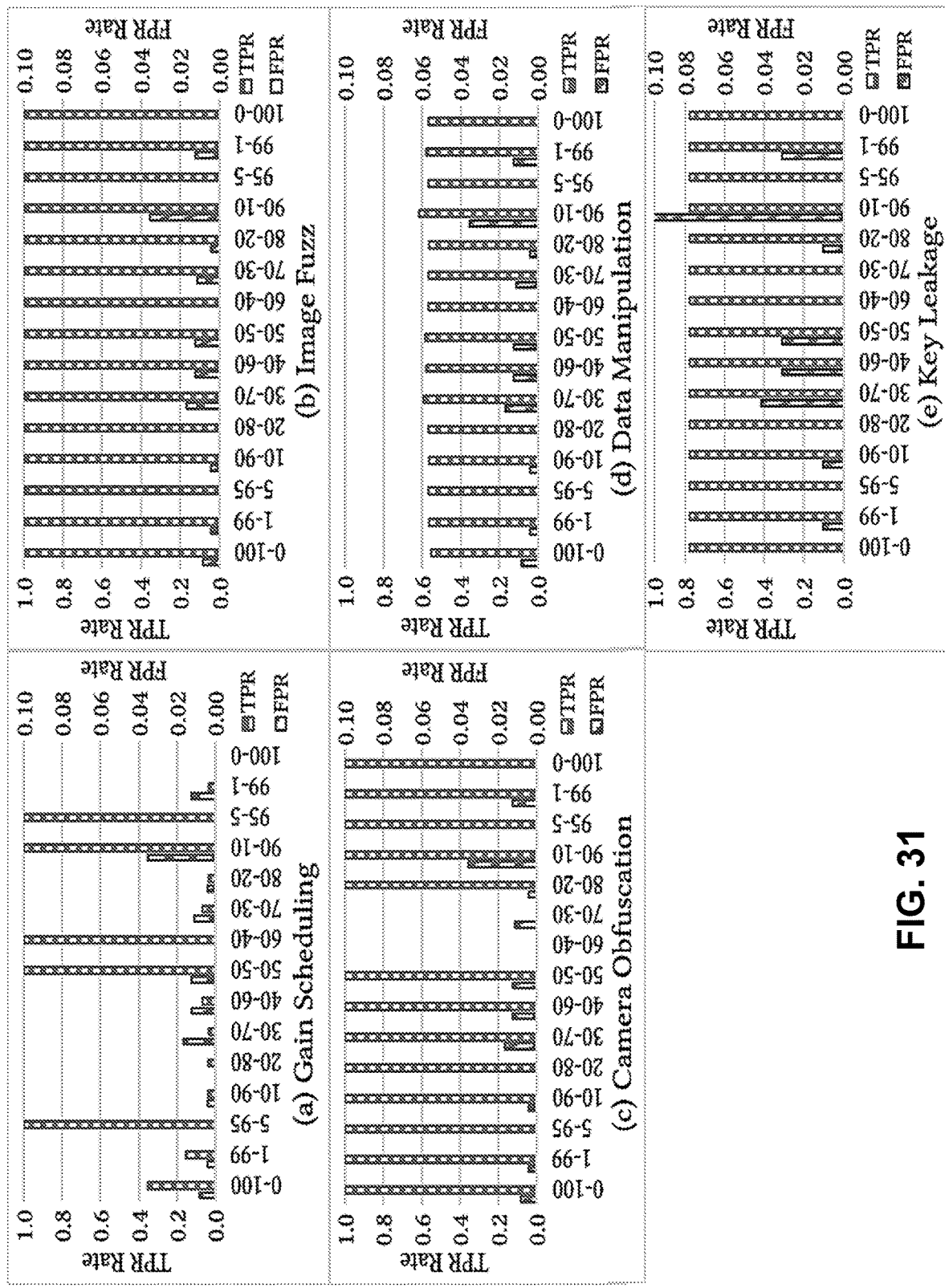
FIG. 31 shows results for individual malware. The X-axis represent the rate, and the Y-axis the results for the different weights of the fitness function. The weights represent the area overhead area overhead $w_A$ and the system false positive rate $w_{FPR}$.

FIG. 31 shows the independent results of Scenario 1 for all malware targeting the UAV benchmark. Analyzing every result independently allows us to analyze the detection rate for each of the five different malware affecting this benchmark independently, and their contribution to the overall detection rate. The X-axis represents the weights for $w_A$ and $w_{FPR}$, and the Y-axis represents the FPR and TPR.

It can be observed in FIG. 31, panel a, that the detection rate of the Gain Scheduling malware varies largely with the different weights assigned to the fitness function. For Scenario 1, the operations are being selected based only on their individual false positive rate and the area overhead. This results in a configuration that monitors as few operations as possible, and it may or may not result in the operations affected by the malware being monitored. This malware is especially undetectable when it has a noticeable effect on just a few operations or doesn't introduce a large variability in the execution timing. For the Image Fuzz, FIG. 31, panel b, and Camera Obfuscation, FIG. 31, panel c, malware, the CDFAD detection can detect the malware with 100% accuracy for most weight configurations, except for when $w_A=60$ and $w_{FPR}=40$, or $w_A=70$ and $w_{FPR}=30$ for Camera Obfuscation. For the Data Manipulation, FIG. 31, panel d, and Key Leakage, FIG. 31, panel e, malware, constantly detect the malware with 0.573 and 0.779 accuracy. In this benchmark, the Data Manipulation malware is the hardest to detect, and therefore yields the lowest detection rate across all malware analyzed.

Figure 32:
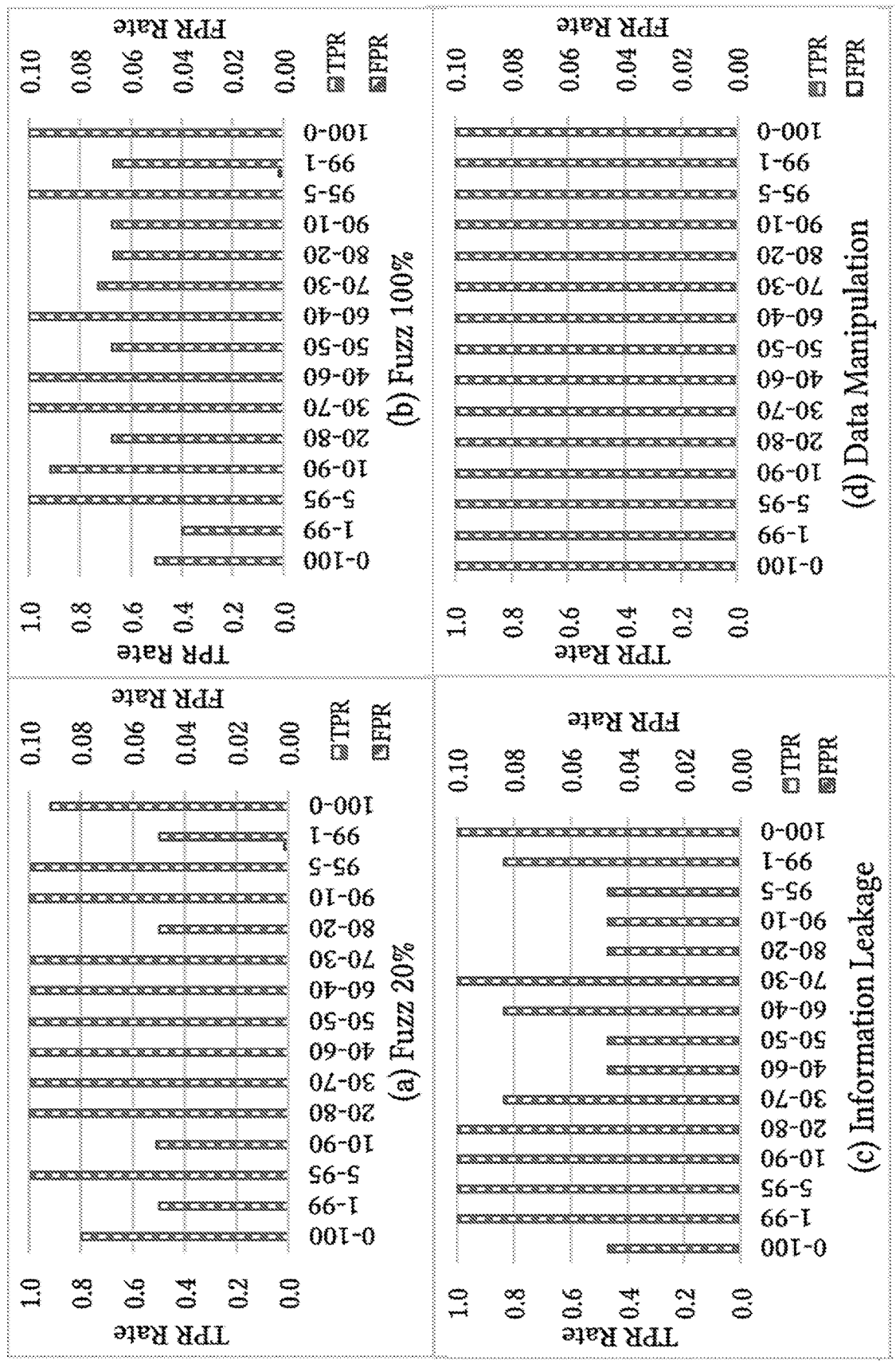
FIG. 32, panels (a) through (d), show the results for individual malware. The X-axis represent the rate, and the Y axis the results for the different weights of the fitness function. The weights represent the area overhead area overhead $w_A$ and the system false positive rate $w_{FPR}$.

Similarly, FIG. 32 shows the independent results of scenario 1 for all different malwares targeting the Pacemaker benchmark. It can be observed that Fuzz 20% malware FIG. 32, panel a, and Fuzz 100% malware FIG. 32, panel b, have similar TPR, with averages of 0.844 and 0.792 respectively. The Information Leakage malware FIG. 32, panel c, has a high detection rate, close to 100% for several weights. Again, the difference in the detection rate between the different weights is due to the selection algorithm, which may or may not select the operations capable of detecting the malware, therefore causing a large variation between them. Finally, the data manipulation malware FIG. 32, panel d, shows that this malware is detected with 100% accuracy across all different weight configurations.

Figure 33:
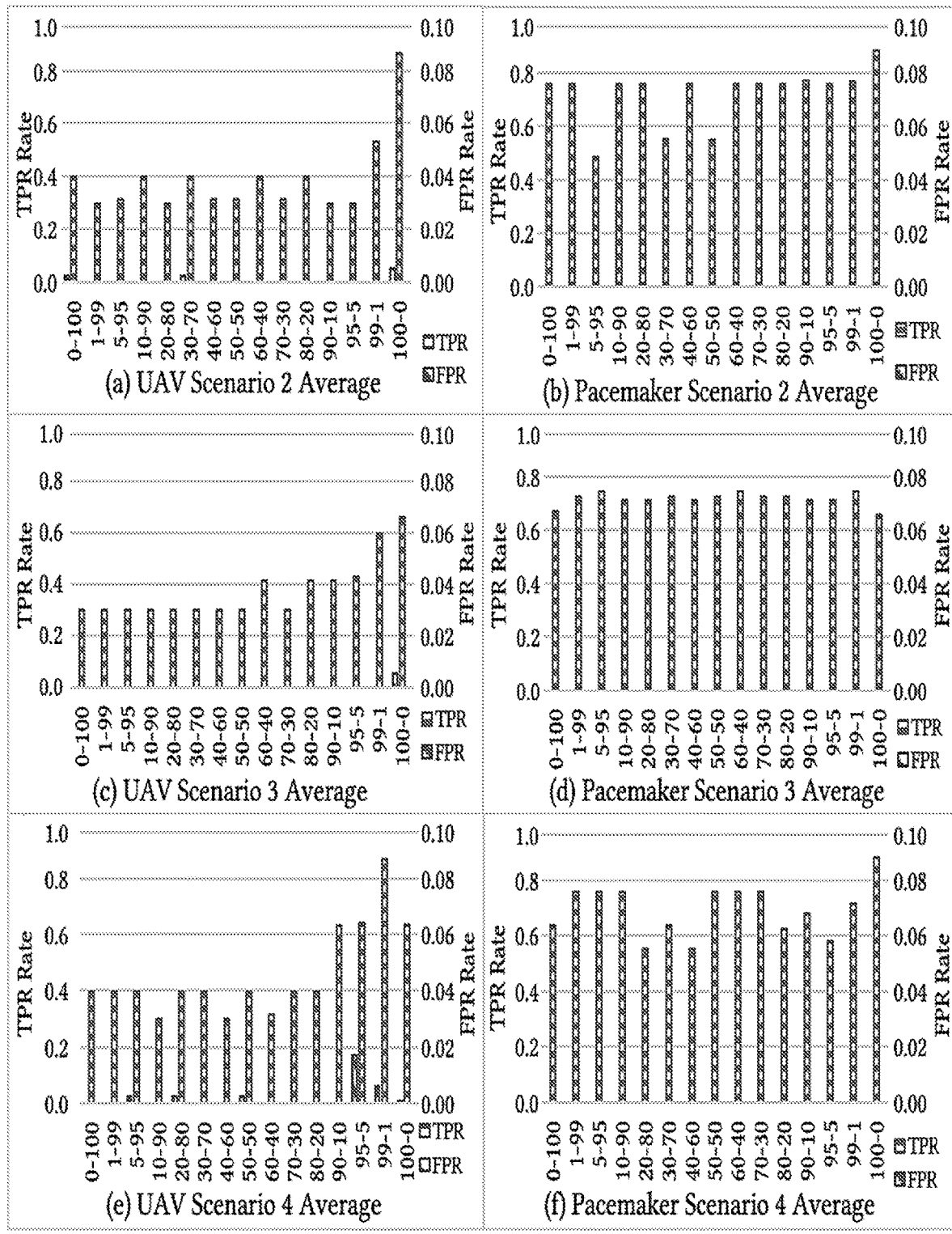
FIG. 33, panels (a) through (f), show average results of each scenario, for both the Pacemaker and the UAV benchmarks. The X-axis represent the rate, and the Y-axis represent the results for the different weights of the fitness function

FIG. 33 shows the average FPR and TPR of Scenarios 2 through 4 for both benchmarks. Scenario 2 has overall average detection rates of 0.389 and 0.722, with average false positive rates of 0.0006 and 0.00 for the UAV and Pacemaker benchmarks, respectively. The best results were achieved with weights of $w_E=100$, and $w_{Path}=0$ for both the UAV and Pacemaker benchmarks, which yields detection rates of 0.867 and 0.884, and false positive rates of 0.0054 and 0.00, respectively.

Scenario 3 has overall average detection rates of 0.375 and 0.717, with average false positive rates of 0.0003 and 0.00 for the UAV and Pacemaker benchmarks respectively. One of the objectives of this scenario is to reduce the false positive rate, and this scenario yields the lowest average false positive rates, but also the lowest average detection rates across all scenarios. The two best results were achieved with weights of $w_{FPR}=100$, and $w_{System}=0$ for the UAV, and $w_{FPR}=60$, and $w_{System}=40$ for the Pacemaker, which yields detection rates of 0.66 and 0.746, with false positive rates of 0.0054 and 0.00 respectively.

Finally, scenario 4 has overall average detection rates of 0.458 and 0.694, with average false positive rates of 0.0021 and 0.00 for the UAV and Pacemaker benchmarks respectively. In contrast with Scenario 3, this scenario doesn't prioritize minimizing the false positive rate, due to this it might have higher false positives for some weight configurations (e.g., $w_A=95$, and $w_{Path}=5$, which yield a false positive rate of 0.017 for the UAV). However, on average the system yield low false positive rates across all weights. The best results were achieved with weights of $w_A=99$, and $w_{Path}=1$ for the UAV, and $w_A=100$, and $w_{Path}=0$ for the Pacemaker, which achieved detection rates of 0.869 and 0.884, with false positive rates of 0.0021 and 0.00 respectively.

Conclusions

The CDF-based timing anomaly detection detects small deviations in a system's timing distribution with high accuracy, for the malware considered. By optimizing a per operation and per path threshold, the presented approach is able to minimize false positives. The proposed design tool will allow system designers to automate the optimization of the monitored operations, window sizes, and strides, given constrains on the energy, area, and false positive rates. The CDF-based anomaly detection further provides an estimate of the probability of malware that quantifies the possibility of deviation caused by malware execution, and potentially enables runtime mitigation methods.

Example 9—Window-Based Statistical Analysis of Timing Subcomponents for Efficient Detection of Malware in Life-Critical Systems This example presents an additional anomaly-based malware detection method for life-critical embedded systems that uses a window-based statistical model of the normal system behavior using timing subcomponents of monitored operation. Instead of independently focusing on the aggregated timing of operations, the proposed timing model enables the monitoring of each timing subcomponent for each operation within the software application. For each operation, a probabilistic formulation based on cumulative distribution functions (CDFs), is used to estimate the presence of malware for individual timing subcomponents. The malware detection calculates an estimated probability of malware by measuring the percentage of the CDF that falls outside the normal boundaries for each operation and each timing subcomponent. Experiments with a smart connected pacemaker prototype and three mimicry malware scenarios were conducted to evaluate the detection rate, false positive rate, detection latency, area, and power consumption of the presented approach. The method was further compared to a state-of-the-art timing-based malware detection.

Assumptions and Threat Model

The goal of CDF-based anomaly detection is to detect sophisticated mimicry malware with minimum or no false positives given the following assumptions and threat model.

1. The target malware is mimicry malware, which attempts to evade anomaly detection by mimicking normal execution behavior. Mimicry malware interleaves malicious and normal execution and are sophisticated enough to escape detection from simple sequence-based anomaly detection. Sequence-based anomaly detection is also used in the present approach, which can detect non-mimicry malware and necessitates an attacker's need to use mimicry malware.

2. The attacker either has access to the system's software or can simulate the system execution to determine the system's execution sequence, which is needed to can create mimicry malware. The attacker is able to remotely insert the malware into the system utilizing software that exploits a vulnerability, which may be unknown or known but unpatched at the time of insertion. The anomaly-based malware detection presented in this paper focuses on detecting malware that has already been inserted in the system and not on detecting the software or system vulnerabilities that lead to the intrusion, both which are beyond the scope of this paper.

3. The target embedded application consists of multiple software tasks (or threads) executing on a single processor core, although it is noted that the detection method presented herein can be applied to other application scenarios including multicore systems.

4. The granularity of detection in this paper is at the level of system and function calls, generically called operations. The proposed approach can be applied at coarser or finer granularities following the same design principles.

5. The malware detection is implemented in hardware and interfaces to the main processor core using the microprocessor trace port. The trace port interface allow non-intrusive (i.e., zero performance impact) observation of monitored operations and subcomponent timing measurements. While the detailed hardware implementation is beyond the scope of this paper, previous malware detection hardware requires approximately 3% power overhead compared to the base system.

To evaluate the CDF-based anomaly detection method, three mimicry malware were considered based on known malware (albeit from different applications) (Sametinger 2015; and Wasicek 2014). The Fuzz malware that is commonly used to interfere with the system's pre-defined functionality by fuzzing (i.e., slightly changing) data. Fuzz malware can be implemented in various levels, which enables the evaluation of the effectiveness of malware detection for different fuzzification levels. The Information Leakage malware reads the patient's cardiac activity log and transmits the data to a third-party server. These three malware were implemented by interleaving malicious operations with mimicked normal operations that overall follow the normal execution sequences of the software tasks. The primary threat is malware affecting legitimate executables, specifically mimicry malware, which assume an attacker knows which operations are monitored. As the approach detects deviations in execution sequences and timing, it can also indirectly detect other malware types.

Time Analysis Models

Lumped Timing Model

Previous time based malware detection methods utilize lumped time measurements. The resulting lumped timing model utilizes a single value that combines all elements that have an effect on the time of the operation (i.e., cache misses, interrupts). This value represent the complete time a specific operation (i.e., readSensor, openFile) takes to execute. This value is obtained by monitoring the processor's trace port for the start and end addresses of known function calls. When the instruction address from the trace port matches the start address of a monitored operation, a timer is enabled. Once the instruction address from the trace port matches the end address of an operation, the timer is disabled. The value obtained from the timer (measured in clock cycles), can be translated to a time value, which is defined as the lumped time for the specific operation. The advantage of this model is its simple implementation. However, the disadvantage is the inherent longer time measured by the operation, which increases the risk of an overlap between the malware time, and the normal time at runtime. This would allow the malware to execute without being detected by the proposed CDF malware detection.

Subcomponent Timing Model

The timing of specific operations is affected by the underlying system architecture, operating system, and execution environment, which can lead to unpredictable timing behaviors (e.g., cache behaviors). For example, the execution time of a function call is influenced by the instructions generated during compilation, pipeline structure, cache/memory access delays, interrupts, context switches, etc. Therefore, the timing of events can vary widely, such that detecting malicious execution may be difficult. Fortunately, the information available from the processor's trace port can be utilized to analyze the execution behavior to separate the timing into several subcomponents.

Two classes of timing subcomponents are defined, namely intrinsic timing and incidental timing. Intrinsic timing is the timing intrinsic to the software execution of operations in the absence of delays or interference from the system architecture, OS, or other tasks. In other words, the intrinsic timing is the ideal software execution time, which is relatively stable. Incidental timing is the timing due to the execution environment in which the software is executed, and incorporates several subcomponents. Within the current approach, incidental timing subcomponents include I$ misses and D$ misses. These subcomponents were chosen due to their inherent ability to detect deviations in the temporal and spatial characteristics of instruction and data addresses caused by malware. By isolating each timing subcomponent, the resulting subcomponent model effectively has tighter bounds on the execution timing, which can be used to increase the detection rate of the CDF based anomaly detector.

As shown in FIG. 1, the execution time of some previously unknown malware overlapped with the lumped timing model of the system. After splitting this lumped model into the subcomponent model it allows us to detect these malware by looking at the intrinsic timing, and dCache timing.

CDF-Based Anomaly Detection

FIG. 2 presents the design flow of the CDF-based anomaly detection method. The software application is first statically analyzed (Stollon 2011) to determine the operations, oi, within all software tasks. For each operation, the system is executed to collect training data by executing the system under various normal execution scenarios, each for a sufficient duration. For a specific window size and stride, the CDF analysis determines the CDFs per window within the training data. These CDFs are used to calculate the upper bound, Boundupper(oi), and lower bound, Boundlower(oi), of the CDF per operation, which can be used to detect deviations at runtime.

This approach is based on the Kolmogorov-Smirnov test (K-S test) and seeks to detect anomalies by statistically comparing the distribution of timing data between a normal system execution model and the runtime execution. Without assuming a specific distribution, the K-S test can be used to test a sample with a reference distribution for equality, where the reference distribution is the normal system model and the sample is the runtime execution. To test if the sample and normal distribution are equal, the K-S test computes the CDF for both, and measures the maximum difference between the two. While the K-S test can be directly applied to detect anomalous executions, one would need to collect 1000s of timing samples for each operation before testing the distribution for equality, thus leading to unacceptably long detection latencies. Based on the K-S test, the present approach measures the execution timing with a small execution window. To construct the normal system model, the CDF for each execution window in the training data is determined. However, instead of storing all CDFs, which would require prohibitively larger memory requirements, only the minimum and maximum boundaries of the CDFs across all windows are stored.

After determining the CDF boundaries, additional normal training data is used to calculate the maximum deviation the CDFs can have from the normal execution while still being considered normal, defined as the threshold. For each operation, the percentage of CDF values for each execution window outside the operation's CDF boundaries is used to determine an estimate of the probability of malware. False positives can be quantified by analyzing the estimated probability of malware for normal execution timing.

At runtime, the detector utilizes the CDF boundaries to estimate the probability of malware for each operation. Timing samples are collected using the same window size and stride. The CDFs for each operation are calculated, and the percentage of CDF values outside the statically determined CDF bounds are used to estimate the probability of malware for each operation. This estimated probability is compared against the predefined threshold to determine if malware is present in the system.

Window-Based CDF Boundary Construction

The CDF represents the distribution of timing samples within an execution window. Creating a model of the normal system behavior using CDFs allows one to estimate the percentage of overlap between runtime CDFs and the normal system model's CDFs. Storing and analyzing the entire execution history for an operation is infeasible and would lead to prohibitively long detection delays. Therefore, the CDF-based anomaly detection collects and analyzes an operation's timing within a fixed execution window that maintains multiple execution timing samples. The window size, defined as the number of timing samples maintained, should be large enough for statistical analysis but small enough to reduce the detection delay. For each window, the stride defines how many new timing samples are collected before re-calculating the CDF. A smaller stride produces smaller changes in the CDF, but requires re-calculating the CDFs more frequently to detect malware. However, a larger stride would allow malware to execute longer before being detected, which could be fatal for some systems. FIG. 3 presents a conceptual overview of the window-based CDF calculations showing the resulting CDFs for four different execution windows and the resulting boundaries. In this example, the window size is 20 and the stride is 5. Thus, each CDF involves 20 samples, in which 25% are new timing samples and 75% are prior samples.

After the CDFs for all windows of an operation are obtained during the training stage, the boundaries that define the normal system's model can be determined. The red bolded lines in FIG. 3 illustrates the CDF bounds for the sample windows. The lower boundary is constructed by points in the CDFs that have the lowest cumulative probability at each timing value, and the upper boundary is constructed by the points in the CDFs that have the highest cumulative probability at each timing value. These boundaries are configured into the anomaly detector and used at runtime. Instead of fitting the boundary curve to be a high dimensional representation, because a fixed window size is used, the CDF's cumulative probability will be discretized with a step size equal to the inverse of the window size. Thus, the CDF boundaries are stored as two scalar arrays, Boundupper(oi)[ ] and Boundlower(oi)[ ], that contain the timing values corresponding to each discrete cumulative probability step.

Estimating probability of malware and threshold-based malware classification For an operation oi, the estimated probability of malware, Pestoi(M), depends on the percentage of CDF values outside the CDF boundaries defined in the normal system model. FIG. 4 presents an example demonstrating how the probability of malware is calculated. The solid lines are the normal boundaries, and the dashed lines are the CDFs obtained from three different windows of runtime timing data. The crossed line CDF is completely outside the CDF boundary, and thus is estimated to have 100% malicious execution. In contrast, the line of circles CDF is completely within the CDF boundaries and thus is estimated to have 0% malicious execution. For a CDF that partially overlaps with the CDF boundary, the probability of malware is estimated as the percentage of points within the CDF that fall outside the boundaries. For example, the line of triangles CDF has a probability of malware Pestoi(M)=1−(0.65−0.20)=0.55, which indicates there is estimated to be a 55% probability the execution is malicious. In practice, with the Boundupper(oi)[ ] and Boundlower (oi)[ ] arrays, the Pestoi(M) is calculated by determining the number of samples that fall outside these bounds. For example, if 19 of 20 timing values in a window are outside the CDF boundary, the estimated probability of malware Pestoi(M)=0.95. An operation is considered malicious if the estimated probability of malware, Pestoi(M) is greater than a predefined threshold.

Due to limitations of design-time training, some normal system executions may deviate from the CDF boundaries. Without accounting for these deviations, a high false positive rate would be expected. The threshold is utilized to minimize that false positive rate. For each operation, the threshold is equal to the minimum overlap found in the second training data set (normal data only). For example, assume the minimum overlap throughout all windows of operation of for the second set of normal timing data is 0.90. This means that the highest estimated probability of malware for normal system execution is 0.10, which in turns means that a runtime estimated probability of malware greater than 0.10 will be reported as malware. This approach strives to ensure the CDF-based anomaly detection is accurate with minimal false positives.

Runtime Detection

At runtime, the threshold of each operation and normal CDF boundaries are configured within the hardware-based malware detector. The malware detector collects timing samples of each operation by analyzing the signals from the processor trace port. Whenever the stride is reached for an operation's window, the detector calculates the CDF and Pestoi(M) for the operation, and compares that estimated probability with the threshold Toj. If Pest oj(M)>Toj, the detector asserts a non-maskable interrupt indicating the presence of malware.

Experimental Results

Smart Connected Pacemaker

A smart connected pacemaker was developed and implemented a complete system prototype using the Artix-7 XC7A200T FPGA. The pacemaker prototype is representative of a complex embedded system that monitors, analyzes, stores, and transmits data, while providing life and safety critical operations. The pacemaker, shown in FIG. 5, includes a simulated heart, a tremor sensor, an impulse pacer, and four timers. The simulated heart beats irregularly and reacts to the impulse pacer controlled by the pacemaker's software. The cardiac activity sensor interfaces to the simulated heart and sends the measured activity to the microprocessor via interrupts. The output from the cardiac activity sensor also controls the Atrio-Ventricular Interval (AVI) and the Ventricular-Atrial Interval (VAI) timers. These timers are used to maintain the appropriate delay between the atrial/ventricular and ventricular/atrial activation and will generate an interrupt if the AVI/VAI exceeds a specific interval configured by a physician. The PVARP/VRP timers filter noise in the ventricular and atrial channels, respectively.

The pacemaker's software consists of three tasks, named Calculation Task, Analysis Task, and Communication Task, and four interrupt service routines (ISRs). The ISRs interact with the pacemaker's cardiac activity sensor and timers. ISR operations include performing the atrial and ventricular pacing and recording ventricular and atrial activity. The first software task calculates the Upper Rate Interval (URI) and records cardiac activity to a daily log file. A second software task analyzes the cardiac activity and detects a high URI, which indicates the pacemaker cannot pace the heart correctly or that pacemaker's cardiac activity sensor has malfunctioned. In the operation of a high URI, the pacemaker immediate transmits a warning message to alert the physician. The third software task is responsible for communication, by which the physician can configure the pacemaker's settings, or a home monitoring device can access daily logs of the cardiac activity.

Detection Rate and False Positive Rate

Using the four mimicry malware, the detection and the false positive rates of the CDF-based anomaly detection are evaluated. The true positive rate (TPR) (i.e., detection rate) is calculated as the number of malware executions classified as malware, divided by the total number of malware executions.

$$TPR = \frac{\text{Malware executions classified as malware}}{\text{Total malware executions}}. \quad (3)$$

Using a separate set of data, the false positive rate (FPR) is calculated as the number of normal executions classified as malware divided by the total number of normal executions.

$$FPR = \frac{\text{Normal executions classified as malware}}{\text{Total normal executions}} \quad (4)$$

Malware Detection Performance

Figure 34:
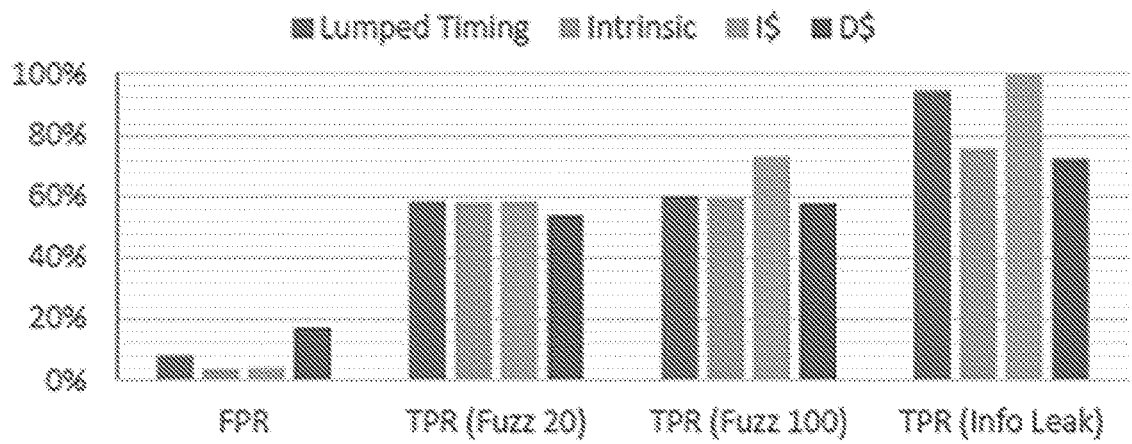
FIG. 34 shows average FPR and TPR for Fuzz 20%, Fuzz 100%, and Information Leakage malware (averaged across all monitored operation and software tasks) in an embodiment of the present invention.

FIG. 34 presents the average FPR and TPR for all monitored operation across all software tasks and malware. For the FPR, both the intrinsic and I$ subcomponents have FPRs less than 3.88%, which is lower than the lumped timing model's FPR of 8.19%. In contrast, the average FPR for the D$ subcomponent is the highest, with an average FPR of 16.98%. The D$ subcomponent has the highest timing variability. In order to reduce the FPR for this subcomponent, additional training data could be collected to improve the CDF bounds (although such analysis is left as future work). Additionally, the results help to isolate which subcomponents contribute to the overall higher FPR for the lumped timing model.

Considering only a single timing subcomponent, the I$ subcomponents yields the highest TPR of 58.21%, 73.05%, and 100% for the Fuzz 20, Fuzz 100, and Information Leakage malware, respectively. For a single subcomponent the D$ subcomponent's alone has the lowest TPR of 53.91%, 57.78%, and 72.42%, respectively. Compared to the lumped timing approach, using the I$ subcomponent yields a 13.05%, and 5.33% increase in the TPR for the Fuzz 100 and Information Leakage respectively malware, and a 0.01% reduction in the Fuzz 20.

Figure 35:
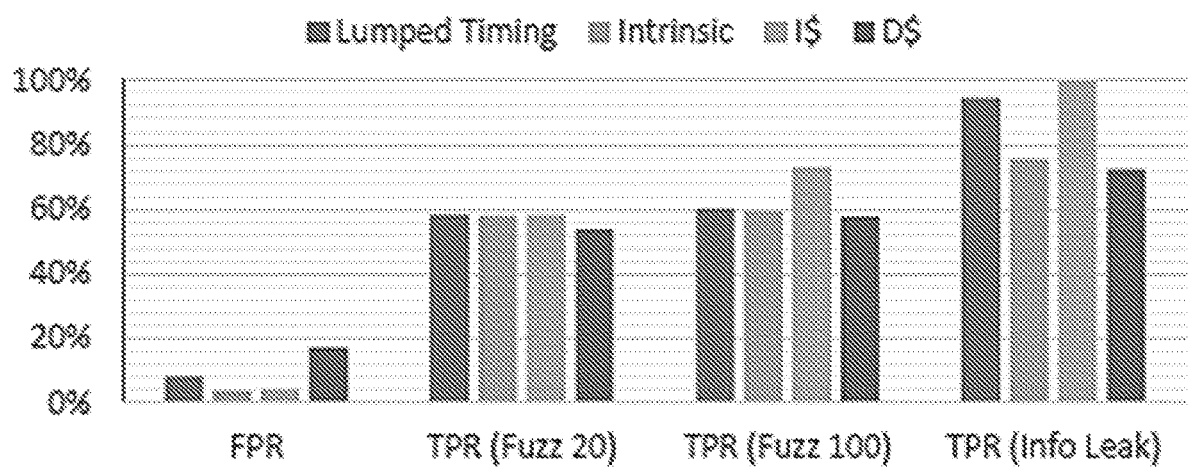
FIG. 35 similarly shows average FPR and TPR for the Calculation Task for the Fuzz 20 and Fuzz 100 malware.

The FPR and TPR were further analyzed for specific tasks within the smart connected pacemaker, specifically focusing on tasks affected by each malware. FIG. 35 presents the average FPR and TPR for the monitored operations within the Calculation Task for the Fuzz 20 and Fuzz 100 malware. The lumped timing models' FPR is 9.58%, while the FPRs for intrinsic and I$ are 4.82% and 4.85%. For the Fuzz 20 malware, the lumped timing model achieves a higher TPR than any individual timing subcomponent (66.55% versus 51.68%), but for the Fuzz 100 malware the I$ subcomponent yields the highest TPR (68.2% versus 64.4%).

Figure 36:
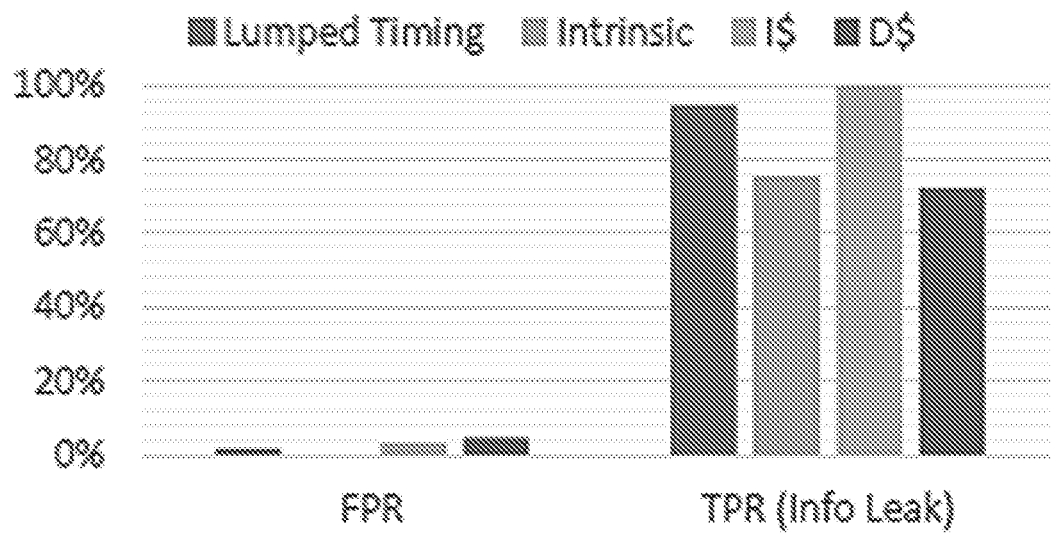
FIG. 36 similarly shows average FPR and TPR for the Information Task for the Information Leakage malware.

FIG. 36 presents the average FPR and TPR for the monitored operations in the Information Task considering the Information Leakage malware. Across all timing models, the FPR remains low, with FPRs of 1.59%, 0%, 3.17%, and 4.76% for the lumped timing, intrinsic, I$ timing, and D$ timing, respectively. The lumped and intrinsic subcomponents have the lowest FPR. The I$ subcomponent again has the highest TPR of 100%, which is a 5% increase over the lumped timing model.

Figure 37:
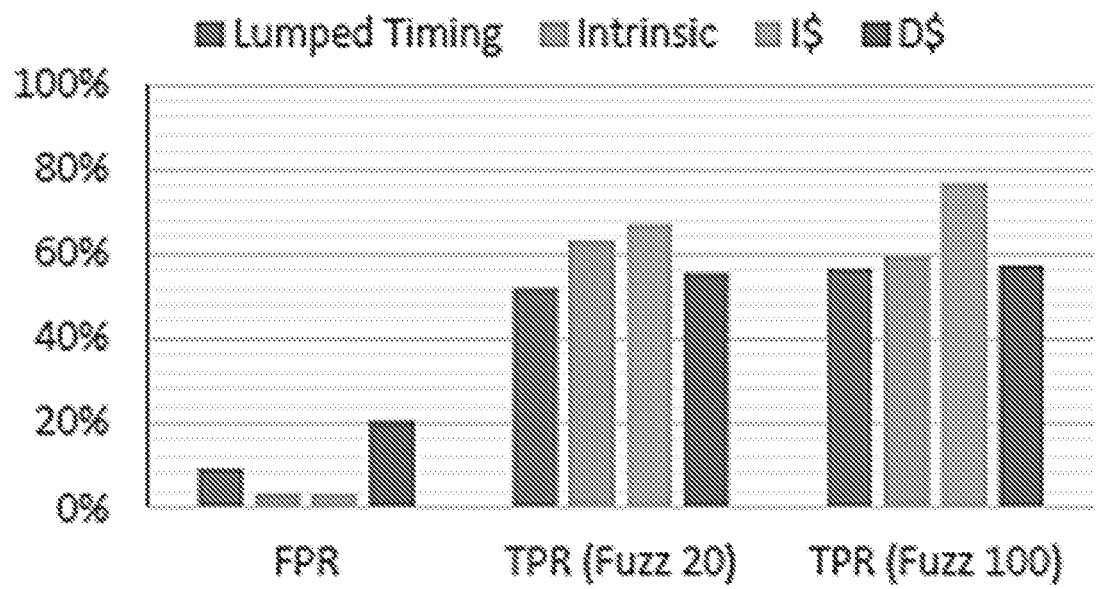
FIG. 37 similarly shows average FPR and TPR results for the Communication Task for the Fuzz 20 and Fuzz 100 malware.

Finally, FIG. 37 presents the average FPR and TPR for monitored operations in the Communication Task considering the Fuzz 20 and Fuzz 100 malware. The intrinsic and I$ subcomponents have the lowest FPR and highest TPR. Compared the lumped timing model, the I$ subcomponent achieves a 6% lower FPR and a 15% higher TPR for the Fuzz 20 malware, and yields a 20% increase in TPR for the Fuzz 100 malware.

Instead of utilizing a single operation for the malware classification, the classification results for each operation can be combined, such that the system execution is considered malicious if at least one operation in the sequence of operations for a software task (or across all software tasks) is malicious. However, without careful selection of the monitored events, this approach could result in a higher FPR. Thus, to evaluate this approach, operations were only considered whose individual FPR is less than 5%. Using this approach, the lumped timing, intrinsic timing, I$ timing, and D$ timing yield TPRs of 99.8%, 92.0%, 99.29%, and 99.90%, respectively, and FPRs of 6.32%, 1.83%, 11.88% and 6.88%, respectively. In this approach, the intrinsic timing subcomponent yields the lowest FPR (1.83%), at the expense of a reduction in the detection rate of −7.07% in average compared to the subcomponents and lumped.

CONCLUSIONS

An anomaly-based malware detection method was presented that combines windows-based statistical analysis with a subcomponent timing model. For malware classification at the operation level, the I$ timing subcomponent yields the highest TPR and second lowest FP, with an average decrease in FPR of 4.31% and an increase in TPR of 6.12% compared to the previous lumped timing model.

For task or level system malware classification, the intrinsic timing subcomponent yields the best tradeoff of FPR and TPR, achieving an FPR of 1.83% and TPR of 92.0%.

Having now fully described the present invention in some detail by way of illustration and examples for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

When a group of materials, compositions, components or compounds is disclosed herein, it is understood that all individual members of those groups and all subgroups thereof are disclosed separately. Every formulation or combination of components described or exemplified herein can be used to practice the invention, unless otherwise stated. Whenever a range is given in the specification, for example, a temperature range, a time range, or a composition range, all intermediate ranges and subranges, as well as all individual values included in the ranges given are intended to be included in the disclosure. Additionally, the end points in a given range are to be included within the range. In the disclosure and the claims, "and/or" means additionally or alternatively. Moreover, any use of a term in the singular also encompasses plural forms.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. Any recitation herein of the term "comprising", particularly in a description of components of a composition or in a description of elements of a device, is understood to encompass those compositions and methods consisting essentially of and consisting of the recited components or elements.

One of ordinary skill in the art will appreciate that starting materials, device elements, analytical methods, mixtures and combinations of components other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. The invention illustratively described herein suitably may be practiced in the absence of any element or elements, limitation or limitations which is not specifically disclosed herein. Headings are used herein for convenience only.

All publications referred to herein are incorporated herein to the extent not inconsistent herewith. Some references provided herein are incorporated by reference to provide details of additional uses of the invention. All patents and publications mentioned in the specification are indicative of the levels of skill of those skilled in the art to which the invention pertains. References cited herein are incorporated by reference herein in their entirety to indicate the state of the art as of their filing date and it is intended that this information can be employed herein, if needed, to exclude specific embodiments that are in the prior art.

The invention claimed is:

1. A system for detecting malware in a device, said system comprising:
    said device having a computer processor, wherein the device is able to be connected to a network or external computer system; and
    a module implemented on the computer processor able to model normal system behavior of the device, compare current system operation to the modeled normal system behavior, and estimate a probability of the current system operation being affected by malware based on performance deviation between the current system operation and the modeled normal system behavior,
    wherein the compared current system operation comprises execution times of one or more operations performed by the device, and wherein estimating the probability of the current system operation being affected by malware comprises determining a number of execution times that fall outside predefined upper and lower timing boundaries in the modeled normal system behavior for the performed operations.

2. The system of claim 1, wherein the module is able to analyze timing samples of execution times of operations performed by the device within an execution window, compare cumulative distribution functions (CDFs) calculated from the timing samples of the execution window against predefined upper and lower CDF boundaries of the modeled normal system behavior, and estimate the probability of the current system operation being affected by malware.

3. The system of claim 2, wherein the execution window is a sliding execution window having a defined number of timing samples, wherein after the module compares the CDFs of the execution widow against the modeled system behavior, a fraction of the timing samples of the sliding execution window are replaced by one or more new timing samples.

4. The system of claim 1, wherein an execution time of an operation performed by the device comprises timing subcomponents, and wherein the module is able to monitor the timing subcomponents for the one or more operations performed by the device, and calculate an estimated probability of malware by measuring a percentage of CDFs for each operation and timing subcomponent that fall outside normal boundaries.

5. The system of claim 1, wherein the module is a software or hardware module.

6. A system for detecting and mitigating malware in a device, said system comprising:
    a) said device having one or more sensors or actuators, and a computer processor able to operate said sensors or actuators, wherein the device is able to be connected to a network or external computer system;
    b) a first module implemented on the computer processor able to operate said one or more sensors or actuators in a base operational mode and operate said one or more sensors or actuators in one or more higher operational modes;
    c) a second module implemented on the computer processor able to estimate a probability that a malware risk will effect a function performed by said one or more sensors or actuators in said one or more higher operational modes, wherein the second module is able to perform a static risk evaluation and, during operation of the device, a dynamic risk evaluation, wherein the risk evaluations are used to determine the calculated risk threshold, estimated probabilities, or both, and wherein performing a static risk evaluation, dynamic risk evaluation, or both, comprises assigning calculated security-health and security-data-sensitivity scores to each operation mode of the device;

d) a third module implemented on the computer processor able to model normal system behavior of the base operational mode and one or more higher operational modes of the device, compare current system operation to the modeled normal system behavior, and estimate a probability of the current system operation being affected by malware based on performance deviation between the current system operation and the modeled normal system behavior; and e) a fourth module implemented on the computer processor able to analyze the estimated probabilities from the second and third modules and cause the first module to switch from the one or more higher operational modes to a higher operational mode having less functionality to the base operational mode when the estimated probabilities exceed a calculated risk threshold.

7. The system of claim 6, wherein the base operational mode performs only essential functions of the device.

8. The system of claim 6, wherein the first, second, third and fourth modules are each a software module.

9. The system of claim 6, wherein software able to operate said one or more sensors or actuators in the base operational mode is implemented on a different region of the computer processor than software able to operate said one or more sensors or actuators in the one or more higher operational modes.

10. The system of claim 9 further comprising middleware software implemented on the computer processor able to transfer data from the software able to operate the base operational mode and other software implemented on the computer processor.

11. The system of claim 6, wherein during operation of the device the second module is able to continuously update the estimated probability that the malware risk will effect functions performed by said one or more sensors or actuators.

12. The system of claim 6, wherein the third module is able to analyze timing samples within a fixed-size execution window, compare cumulative distribution functions (CDFs) of the execution window against the modeled normal system behavior, and estimate the probability of the current system operation being affected by malware.

13. The system of claim 6, wherein said device is a device implanted in a patient and the one or more sensors or actuators are able to monitor a biological function in a patient, administer a drug to the patient, administer an electric pulse to the patient, or combinations thereof.

14. The system of claim 6, wherein the calculated security-health and security-data-sensitivity scores are an estimation of a likelihood that safety of a user is impacted if a specified task is compromised.

15. A method for detecting malware in a device able to be connected to a network or external computer system, said method comprising the steps of:

modeling normal system behavior of the device;

comparing current system operation of the device to the modeled normal system behavior;

estimating a probability of the current system operation of the device being affected by malware based on performance deviation between the current system operation and the modeled normal system behavior; and performing a static risk evaluation and, during operation of the device, a dynamic risk evaluation, and determining a calculated risk threshold, estimated probabilities, or both, based on said evaluations, wherein performing a static risk evaluation comprises assigning calculated security-health and security-data-sensitivity scores to tasks performed by each operational mode of the device, calculating a task risk score for each of said tasks, and establishing static risk thresholds for each operation mode based on accumulated task risk scores.

16. The method of claim 15 comprising the steps of:

operating one or more sensors or actuators of said device in a base operational mode and one or more higher operational modes; and modeling normal system behavior of the operational modes of the device, comparing current system operation to the modeled normal system behavior, and estimating a probability of the current system operation being affected by malware based on performance deviation between the current system operation and the modeled normal system behavior.

17. The method of claim 16 further comprising estimating a probability that a malware risk will effect a function performed by said one or more sensors or actuators in said operational modes; and switching from one or more higher operational modes to a higher operational mode having less functionality or to the base operational mode when the estimated probabilities exceed a calculated risk threshold.

18. The method of claim 16 wherein software able to operate said one or more sensors or actuators in the base operational mode is implemented on a different region of a computer processor in the device than software able to operate said one or more sensors or actuators in the one or more higher operational modes.

19. The method of claim 18 further comprising the step of transferring data from software operating the base operational mode to other software implemented on a computer processor of the device through secured middleware software implemented on the computer processor.

20. The method of claim 16 further comprising the step of, during operation of the device, continuously updating the estimated probability that the malware risk will effect functions performed by said one or more sensors or actuators.

21. The method of claim 15 comprising analyzing timing samples of operations performed by the system within an execution window, comparing cumulative distribution functions (CDFs) of the execution window against the modeled normal system behavior, and estimating the probability of the current system operation being affected by malware.

22. The method of claim 15 comprising monitoring timing subcomponents for operations performed by the device, and calculating an estimated probability of malware by measuring a percentage of CDFs for each operation and timing subcomponent that fall outside normal boundaries.

23. The method of claim 15 wherein the device is a device implanted in a patient able to monitor a biological function in a patient, administer a drug to the patient, administer an electric pulse to the patient, or combinations thereof.

24. The method of claim 15, wherein the calculated security-health and security-data-sensitivity scores are an estimation of a likelihood that safety of a user is impacted if a specified task is compromised.

* * * * *